US009340530B2

(12) United States Patent
Mandal et al.

(10) Patent No.: US 9,340,530 B2
(45) Date of Patent: May 17, 2016

(54) PREPARATION AND USE OF BICYCLIC HIMBACINE DERIVATIVES AS PAR-1 RECEPTOR ANTAGONISTS

(71) Applicant: Merck, Sharp & Dohme Corp.

(72) Inventors: Mihir Mandal, Westfield, NJ (US); Timothy A. Blizzard, Princeton, NJ (US); Helen Chen, Marlboro, NJ (US); Harry Chobanian, Aberdeen, NJ (US); Yan Guo, Westfield, NJ (US); Barbara Pio, West Orange, NJ (US); Zhicai Wu, Montvale, NJ (US); Tesfaye Biftu, Freehold, NJ (US); William J. Greenlee, Teaneck, NJ (US); Johnny Zhaoning Zhu, Slough (GB)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/383,176

(22) PCT Filed: Feb. 27, 2013

(86) PCT No.: PCT/US2013/027838

§ 371 (c)(1),
(2) Date: Sep. 5, 2014

(87) PCT Pub. No.: WO2013/134012

PCT Pub. Date: Sep. 12, 2013

(65) Prior Publication Data

US 2015/0025046 A1 Jan. 22, 2015

Related U.S. Application Data

(60) Provisional application No. 61/607,062, filed on Mar. 6, 2012.

(51) Int. Cl.

| | |
|---|---|
| ***A61K 31/44*** | (2006.01) |
| ***C07D 401/06*** | (2006.01) |
| ***C07D 417/14*** | (2006.01) |
| ***C07D 405/06*** | (2006.01) |
| ***A61K 45/06*** | (2006.01) |
| ***A61K 31/365*** | (2006.01) |
| ***A61K 31/4365*** | (2006.01) |
| ***A61K 31/443*** | (2006.01) |
| ***A61K 31/4439*** | (2006.01) |
| ***A61K 31/616*** | (2006.01) |
| ***C07D 401/14*** | (2006.01) |
| ***C07D 405/14*** | (2006.01) |
| ***C07D 413/14*** | (2006.01) |
| ***A61K 31/444*** | (2006.01) |

(52) U.S. Cl.

CPC ............ *C07D 405/06* (2013.01); *A61K 31/365* (2013.01); *A61K 31/4365* (2013.01); *A61K 31/443* (2013.01); *A61K 31/444* (2013.01); *A61K 31/4439* (2013.01); *A61K 31/616* (2013.01); *A61K 45/06* (2013.01); *C07D 401/06* (2013.01); *C07D 401/14* (2013.01); *C07D 405/14* (2013.01); *C07D 413/14* (2013.01); *C07D 417/14* (2013.01)

(58) Field of Classification Search

CPC . A61K 31/4439; A61K 31/444; A61K 45/06; A61K 31/443; C07D 405/06; C07D 413/14; C07D 405/14; C07D 417/14; C07D 401/06

USPC .......... 546/271.4, 269.1, 268.4, 284.1, 269.7, 546/277.1, 256; 514/161, 339, 255.05, 514/210.2, 338, 256, 333, 210.18, 337, 514/301; 544/333, 405

See application file for complete search history.

(56) References Cited

U.S. PATENT DOCUMENTS

| | | | | |
|---|---|---|---|---|
| 6,063,847 | A * | 5/2000 | Chackalamannil et al. | .. 524/297 |
| 7,488,752 | B2 * | 2/2009 | Chackalamannil et al. | .. 514/469 |
| 2004/0006105 | A1 | 1/2004 | Chackalamannil et al. | |

(Continued)

OTHER PUBLICATIONS

Patani; Chem. Rev. 1996, 96, 3147-3176.*

(Continued)

*Primary Examiner* — Janet L Andres
*Assistant Examiner* — Daniel Carcanague
(74) *Attorney, Agent, or Firm* — Nicole M. Beeler; Catherine D. Fitch

(57) ABSTRACT

The present invention relates to bicyclic himbacine derivatives of the formula or a pharmaceutically acceptable salt thereof, wherein: X is —O—, —N(R), —C($R^8$)($R^9$) or —C(O)—; and Y is —O—, —N(R), —C($R^8$)($R^9$) or —C(O)— and the remaining variables are described herein. The compounds of the invention are effective inhibitors of the PAR-1 receptor. The inventive compounds may be used for the treatment or prophylaxis of disease states such as ACS, secondary prevention of myocardial infarction or stroke, or PAD.

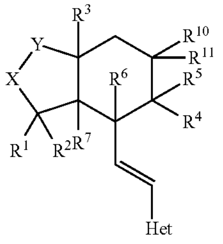

14 Claims, No Drawings

(56) References Cited

U.S. PATENT DOCUMENTS

| | | | |
|---|---|---|---|
| 2007/0149518 | A1 | 6/2007 | Chackalamannil et al. |
| 2008/0090830 | A1 | 4/2008 | Chackalamannil et al. |
| 2011/0065676 | A1 | 3/2011 | Perelman et al. |

OTHER PUBLICATIONS

Gordon; PNAS, 1999, 96, 12257-12262.*
Clasby; J. Med. Chem. 2007, 50, 129-138.*
Gordon, et. al., "Design, synthesis and biological characterization of a peptide-mimetic antagonist for a tethered-ligand receptor", PNAS, Oct. 26, 1999, vol. 96, No. 22, pp. 12257-12262.
International Search Report for PCT/US13/27838 mailed on May 20, 2013; 2 pages.
Extended European Search Report for 13757283.0 mailed Jul. 28, 2015. 7 pages.

* cited by examiner

PREPARATION AND USE OF BICYCLIC HIMBACINE DERIVATIVES AS PAR-1 RECEPTOR ANTAGONISTS

RELATED APPLICATIONS

This application is a §371 National Stage Application of PCT/US2013/027838, filed on Feb. 27, 2013, which claims benefit to provisional application U.S. Ser. No. 61/607,062, filed on 6 Mar. 2012, herein incorporated by reference.

FIELD OF THE INVENTION

The present invention relates to bicyclic himbacine derivatives, which are useful as protease activated receptor-1 (PAR-1) antagonists and might be expected to be cannabinoid ($CB_2$) receptor inhibitors. PAR-1 receptors are also known in the art as thrombin receptor antagonists (TRA). The inventive compounds have utility in treating disease states such as acute coronary syndrome (ACS) ((unstable angina, non-ST-segment elevation [NSTE] myocardial infarction [MI], and ST segment-elevation myocardial infarction [STEMI]), secondary prevention of myocardial infarction or thrombotic stroke (secondary prevention) or peripheral artery disease (PAD), which is also know in the art as peripheral vascular disease. The present invention also relates to pharmaceutical compositions comprising the inventive compounds as well as processes for their preparation.

BACKGROUND OF THE INVENTION

Thrombin is known to have a variety of activities in different cell types. PAR-1 receptors are known to be present in such cell types as human platelets, vascular smooth muscle cells, endothelial cells and fibroblasts. The art indicates that PAR-1 receptor antagonists would be expected to be useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al., *J. Med. Chem.*, 39 (1996), p. 4879-4887, tetra- and pentapeptides are disclosed as being potent thrombin receptor antagonists, for example N-trans-cinnamoyl-p-fluoroPhe-p-guanidinoPhe-Leu-Arg-$NH_2$ and N-trans-cinnamoyl-p-fluoroPhe-p-guanidinoPhe-Leu-Arg-Arg-$NH_2$. Peptide thrombin receptor antagonists are also disclosed in WO 94/03479.

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation. As such, the art suggests that a selective $CB_2$ receptor binding agent might be expected to have therapeutic utility in the control of diseases associated with rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (R. G. Pertwee, *Curr. Med. Chem.* 6(8), (1999), 635; M. Bensaid, *Molecular Pharmacology,* 63 (4), (2003), 908).

Himbacine, a piperidine alkaloid of the formula

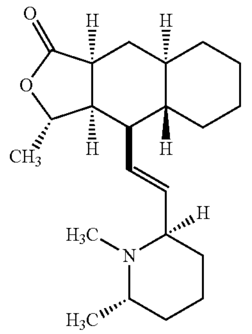 [SMILES: C[C@@H]1OC(=O)[C@H]2C[C@H]3CCCC[C@@H]3[C@@H](/C=C/[C@H]3CCC[C@H](C)N3C)[C@@H]12]

has been identified as a muscarinic receptor antagonist. The total synthesis of (+)-himbacine is disclosed in Chackalamanil et al., *J. Am. Chem. Soc.,* 118 (1996), p. 9812-9813.

Substituted bi- and tricyclic thrombin receptors antagonists are known in the art to treat thrombin receptor mediated disorders such as thrombosis, atherosclerosis, restenosis, hypertension, angina pectoris, angiogenesis related disorders, arrhythmia, a cardiovascular or circulatory disease or condition, heart failure, ACS, myocardial infarction, glomerulonephritis, thrombotic stroke, thromboembolytic stroke, PAD, deep vein thrombosis, venous thromboembolism, a cardiovascular disease associated with hormone replacement therapy, disseminated intravascular coagulation syndrome and cerebral infarction, as well as $CB_2$ receptor mediated disorders. U.S. Pat. No. 6,645,987 and U.S. Pat. No. 6,894,065 disclose PAR-1 receptor antagonists of the structure:

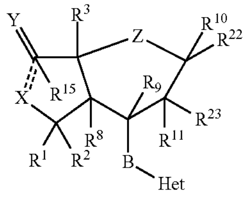

where $R^{10}$ may be groups such as H, alkyl, haloalkyl, hydroxyl, etc. and $R^{22}$ may be groups such as H, optionally substituted alkyl, hydroxyl, etc. Other known substituted thrombin receptor antagonists are disclosed in U.S. Pat. No. 6,063,847, U.S. Pat. No. 6,326,380, U.S. Pat. No. 7,037,920, U.S. Pat. No. 7,488,742, U.S. Pat. No. 7,713,999, U.S. Pat. No. 7,442,712, U.S. Pat. No. 7,488,752, U.S. Pat. Nos. 7,776,889, 7,888,369, U.S. Pat. No. 8,003,803 and U.S. Pat. No. 8,022,088. US 2008/0090830 and Chackalamannil et al., *J. Med. Chem.,* 49 (2006), p. 5389. A PAR-1 receptor antagonist that exhibits good thrombin receptor antagonist activity (potency) and selectivity is vorapaxar (Merck & Co., Inc.), which has the following structure:

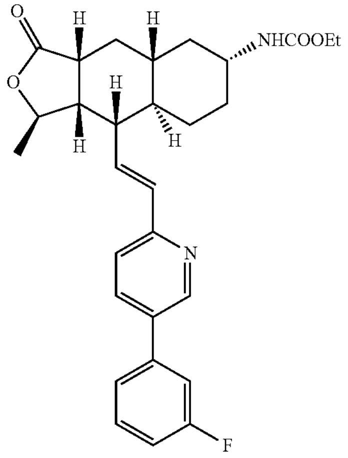

This compound is presently undergoing clinical trials and is disclosed in U.S. Pat. No. 7,304,048. A crystalline form of the bisulfate salt of vorapaxar is disclosed in U.S. Pat. No. 7,235, 567.

WO2011/162,562 to LG Life Sciences LTD. describes a series of [6+5] fused bicycle derivatives of the general structure:

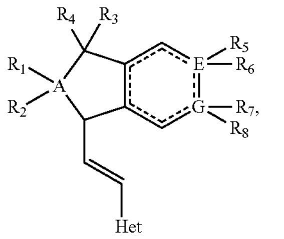

where $R_5$ and $R_6$ are inter alia both fluoro groups, as inhibitors of the PAR-1 receptor. The compounds are taught to be useful in the treatment and prevention of thrombus, platelet aggregation, atherosclerosis, restenosis, blood coagulation, hypertension, arrhythmia, angina pectoris, heart failure, inflammation and cancer when used alone or with other cardiovascular agents.

WO2011/28420 and WO2011/28421, both to Sanofi-Aventis, disclose compounds that are reported to be PAR-1 receptor antagonists. The compounds disclosed in WO2011/28420 are pyridyl-vinyl pyrazoloquinolines derivatives and have the following general structure:

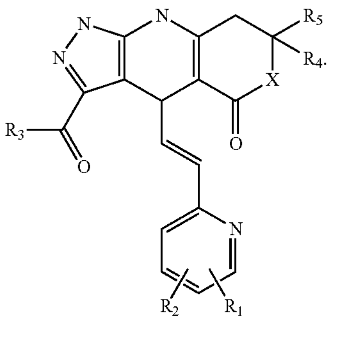

WO2011/28421 discloses tricyclic pyridyl-vinyl-pyrrole derivatives of the following general structure:

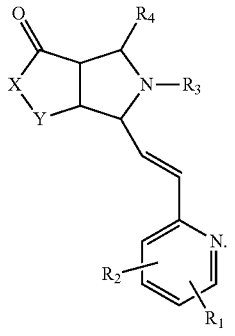

Applicants discovered in accordance with the present invention that the inventive compounds act as inhibitors of PAR-1 receptor and, based upon their structure, might also act as inhibitors of the $CB_2$ receptor. Therefore, the inventive compounds might be expected to be useful in treating disease states associated with the inhibition of these receptors.

There is a need for new compounds, formulations, treatment and therapies to treat diseases associated with the PAR-1 and $CB_2$ receptors. Moreover, there is a need to develop therapeutics that exhibit improved therapeutic profiles, such as desirable half-life and reduced unintended effects. It is, therefore, an object of this invention to provide compounds useful in the treatment, prevention or amelioration of such diseases or disorders. These and other objectives will become evident from the following description.

SUMMARY OF THE INVENTION

In its many embodiments, the present invention provides for a novel class of bicyclic himbacine derivatives, which are PAR-1 receptor antagonists, or metabolites, stereoisomers, salts, solvates or polymorphs thereof, processes of preparing such compounds, pharmaceutical compositions comprising one or more such compounds, processes of preparing pharmaceutical compositions comprising one or more such compounds and methods of treatment, inhibition or amelioration of one or more disease states associated with the PAR-1 receptor by administering an effective amount at least one of the inventive bicyclic himbacine derivatives to a patient in need thereof.

In one aspect, the present application discloses a compound or a pharmaceutically acceptable salt, metabolite, solvate, prodrug or polymorph of said compound, said compound or pharmaceutically acceptable salt thereof having the general structure shown in Formula I Formula I

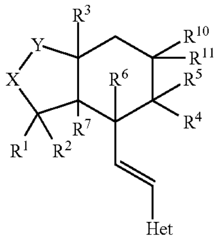

wherein:

X is —O—, —N(R), —C($R^8$)($R^9$) or —C(O)—;

Y is —O—, —N(R), —C($R^8$)($R^9$) or —C(O)—;

R is H, alkyl or —$S(O)_2$—$R^9$ $R^1$ is H, alkyl or haloalkyl;

$R^2$ is H, alkyl or haloalkyl;

$R^3$ is H, —$N_3$, —CN; halogen, —$OR^{12}$, —N($R^{25}$)($R^{26}$), —C(O)$OR^{12}$, —C(O)N($R^{25}$)($R^{26}$), —$SO_2$($R^{12}$), $R^{17}$-alkyl, $R^{17}$-cycloalkyl, $R^{17}$-aryl, $R^{17}$-heterocycloalkyl, $R^{17}$-aryl, or $R^{17}$-heteroaryl;

$R^4$ is H, alkyl, or haloalkyl;

$R^5$ is H, alkyl or haloalkyl;

$R^6$ is H or alkyl;

$R^7$ is H or alkyl;

$R^8$ independently is H or alkyl;

$R^9$ independently is H or alkyl;

$R^{10}$ is halogen or —CN;

$R^{11}$ is H, halogen or alkyl;

$R^{12}$ independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{13}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{14}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, —C(O)$R^{12}$, —$S(O)_2$—$R^{12}$, $R^{17}$-heteroaryl, $R^{17}$-heteroarylalkyl or $R^{17}$-heteroarylalkenyl;

or $R^{13}$ and $R^{14}$ taken together with the nitrogen atom to which they are attached are —$(CH_2)_4$—, —$(CH_2)_5$— or —$(CH_2)_2$—N($R^8$)—$(CH_2)_2$—;

Het is a 5- or 6-membered heterocycloalkyl, heterocyclenyl or a heteroaryl ring containing 3 to 5 carbon atoms and 1 or 2 heteroatoms selected from the group consisting of N, O or S, with the proviso that there are no adjacent oxygen or sulfur atoms present in said groups, and when Het is a N-containing heteroaromatic group with one heteroatom present, then the ring nitrogen can form an N-oxide or a quaternary group with an alkyl group; wherein: 1) Het is attached to the double bond by a carbon atom ring member of Het; and 2) Het is substituted by 1 to 4 moieties, W, where each W is independently hydrogen, alkyl, haloalkyl, (e.g. fluoroalkyl, difluoroalkyl, trifluoroalkyl), $R^{17}$-cycloalkyl, $R^{17}$-heterocycloalkyl, $R^{16}$-alkenyl, $R^{17}$-aryl, $R^{17}$-heteroaryl, $R^{17}$-arylalkyl, $R^{17}$-arylalkenyl, $R^{17}$-heteroarylalkyl, $R^{17}$-heteroarylalkenyl, hydroxyalkyl; dihydroxyalkyl; aminoalkyl, alkylaminoalkyl, di-(alkyl)-aminoalkyl, alkoxy, -alkyl-SH, —S-alkyl, alkenyloxy, halogen, —$NR^{13}R^{14}$, —CN, —OH, —C(O)$OR^{12}$, —$COR^{12}$, —$OS(O_2)CF_3$, —$CH_2OCH_2CF_3$, —C(O)$NR^{13}NR^{14}$, —$OCHR^{15}$-phenyl, phenoxyalkyl, —$NR^8COR^{12}$, —$NR^8SO_2R^{12}$, —C(O)$NR^{13}R^{14}$, —OC$(R^{15})_2COOR^{12}$, —OC$(R^{15})_2$C(O)$NR^{13}R^{14}$ alkoxy optionally substituted by alkyl, amino or —$NR^8$C(O)$OR^{12}$, or alkyl optionally substituted with —$NR^{13}R^{14}$, —$NR^{13}COR^{12}$, —$NR^8CONR^{13}R^{14}$, —$NR^8$C(O)$OR^{12}$, —$NR^8S(O)_2R^{12}$, —$NR^8S(O)_2NR^{13}R^{14}$—C(O)$OR^{12}$, —$CONR^{13}R^{14}$ or —OH;

$R^{15}$ independently is H, alkyl, cycloalkyl, alkoxyalkyl, hydroxyalkyl, aminoalkyl or phenyl;

$R^{16}$ is 1 to 3 moieties and each $R^{16}$ is independently hydrogen, halogen, —OH, alkoxy, -alkyl-SH, —S-alkyl, $R^{24}$-aryl, $R^{24}$-heteroaryl, $R^{24}$-heterocycloalkyl, $R^{24}$-cycloalkyl, $R^{24}$-cycloalkenyl, $R^{24}$-heterocyclenyl, —OC(O)$R^{20}$, —C(O)$OR^{20}$, —C(O)$R^{20}$, —C(O)$NR^{21}R^{22}$, —$NR^{21}R^{22}$, —$NR^8$C(O)$R^{20}$, —$NR^8$C(O)$NR^{21}R^{22}$, —$NR^8SO_2R^{20}$, —OC(O)$NR^{21}R^{22}$, $R^{23}$-alkenyloxy, $R^{23}$-alkynyloxy, $R^{23}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —$NR^8SO_2NHR^{21}$ or —C(=$NOR^{18}$)$R^{19}$;

$R^{17}$ is 1 to 3 moieties and each $R^{17}$ independently hydrogen, $R^{23}$-alkyl, halogen, —CN, —$NO_2$, —OH, $R^{23}$-alkoxy, —OC(O)$R^{20}$, —C(O)$OR^{20}$, —C(O)$R^{20}$, —C(O)$NR^{21}R^{22}$, —$NR^{21}R^{22}$, —$NR^8$C(O)$R^{20}$, —$NR^8$C(O)$NR^{21}R^{22}$, —$NR^8SO_2R^{20}$, —OC(O)$NR^{21}R^{22}$, —S(O)$R^{20}$, —$S(O)_2R^{20}$, —$SR^{20}$, —$SO_2NR^{21}R^{22}$, —$NHCOR^{20}$, —C(NH)—$NH_2$, —C(O)$NR^{21}R^{22}$, $R^{23}$-alkenyloxy, $R^{23}$-alkynyloxy, $R^{24}$-cycloalkyl, $R^{24}$-cycloalkenyl, $R^{24}$-heterocycloalkyl, $R^{24}$-aryl, $R^{24}$-heteroaryl, $R^{24}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —$NR^8SO_2NHR^{21}$ or —C(=$NOR^{18}$) $R^{19}$;

$R^{18}$ is H, alkyl, phenyl or benzyl;

$R^{19}$ is H, alkyl, phenyl or benzyl;

$R^{20}$, $R^{21}$ and $R^{22}$ are independently hydrogen, alkyl, haloalkyl, alkenyl, alkynyl, aryl, aralkyl, cycloalkyl, halocycloalkyl or alkoxyalkyl;

$R^{23}$ is 1 to 3 moieties and each $R^{23}$ is independently hydrogen, halogen, —OH, alkyl, haloalkyl, alkoxy, —CN, amino, alkylamino, dialkylamino, di(alkyl)amino, haloalkoxy (e.g. —$OCF_3$), hydroxyalkyl, —CHO, —C(O)alkylamino, —C(O)alkylamino, —NHC(O)alkyl or —N(alkyl)C(O) alkyl;

$R^{24}$ is 1 to 3 moieties and each $R^{24}$ is independently hydrogen, halogen, —OH, alkyl, haloalkyl, alkoxy, —CN, amino, alkylamino, dialkylamino, di(alkyl)amino, haloalkoxy (e.g. —$OCF_3$), hydroxyalkyl, —CHO, —C(O)alkylamino, C(O) alkylamino, NHC(O)alkyl or —N(alkyl)C(O)alkyl;

$R^{25}$ is H, $R^{17}$-alkyl, $R^{17}$-cycloalkyl, $R^{17}$-aryl, $R^{17}$-heterocycloalkyl, $R^{17}$-aryl or $R^{17}$-heteroaryl;

$R^{26}$ is H, OH, —C(O)N($R^{21}$)($R^{22}$), —C(S)N($R^{21}$)($R^{22}$), —C(O)$R^{12}$, —$S(O)_2R^{12}$; $R^{17}$-alkyl, $R^{17}$-cycloalkyl, $R^{17}$-aryl, $R^{17}$-heterocycloalkyl, $R^{17}$-aryl or $R^{17}$-heteroaryl.

Another aspect of the present invention is pharmaceutical compositions comprising a therapeutically effective amount of at least one compound of Formula I or a pharmaceutically acceptable salt thereof and a pharmaceutically acceptable carrier.

Another aspect of the present invention is pharmaceutical compositions comprising a therapeutically effective amount of at least one compound of Formula I or a pharmaceutically acceptable salt thereof, at least one additional cardiovascular agent and a pharmaceutically acceptable carrier.

Another aspect of the present invention is the possible prevention of one or more disease state associated with inhibiting the PAR-1 receptor by administering an effective amount of a compound of Formula I or a pharmaceutically acceptable salt thereof to a patient in need thereof.

Another aspect of the present invention is a method of inhibiting platelet aggregation comprising administering to a mammal an effective amount of a compound of Formula I or a pharmaceutically acceptable salt thereof.

It is further contemplated that the combination of the invention could be provided as a kit comprising in a single package at least one compound of Formula I or a pharmaceutically acceptable salt thereof in a pharmaceutical composition, and at least one separate pharmaceutical composition, such as, for example a separate pharmaceutical composition comprising a cardiovascular agent.

The compounds of the present invention can be useful in the treatment, amelioration or prevention of one or more conditions associated with inhibiting the PAR-1 receptor by administering at least one compound of Formula I or a pharmaceutically acceptable salt thereof to a mammal in need of such treatment. Conditions that could be treated or prevented by inhibiting the PAR-1 receptor include thrombosis, atherosclerosis, restenosis, hypertension, angina pectoris, angiogenesis related disorders, arrhythmia, a cardiovascular or circulatory disease or condition, heart failure, ACS, myocardial infarction, glomerulonephritis, thrombotic stroke, thromboembolytic stroke, PAD, deep vein thrombosis, venous thromboembolism, a cardiovascular disease associated with hormone replacement therapy, disseminated intravascular coagulation syndrome and cerebral infarction.

Another embodiment is the possible treatment, amelioration or prevention of ACS, secondary prevention of myocardial infarction or stroke, urgent coronary revascularization, or PAD by administering at least one compound of Formula I or a pharmaceutically acceptable salt thereof to a mammal in need of such treatment.

Another embodiment of this invention is in the possible treatment, amelioration or prevention of one or more conditions associated with cardiopulmonary bypass surgery (CPB) by administering effective amount of at least one compound of Formula I or a pharmaceutically acceptable salt thereof to a subject of said CPB surgery. CPB surgery includes coronary artery bypass surgery (CABG), cardiac valve repair and replacement surgery, pericardial and aortic repair surgeries. The conditions associated with CABG include bleeding, thrombotic vascular events (such as thrombosis or restenosis), vein graft failure, artery graft failure, atherosclerosis, angina pectoris, myocardial ischemia, acute coronary syndrome, myocardial infarction, heart failure, arrhythmia, hypertension, transient ischemic attack, cerebral function impairment, thromboembolic stroke, cerebral ischemia, cerebral infarction, thrombophlebitis, deep vein thrombosis and PAD.

Another embodiment of the present invention is the possible use of a compound of Formula I or a pharmaceutically acceptable salt thereof for the manufacture of a medicament for the treatment, amelioration or prevention of one or more conditions associated with inhibiting the PAR-1 receptor in a patient.

DETAILED DESCRIPTION

In an embodiment, the present invention provides compounds represented by structural Formula I, or pharmaceutically acceptable salt thereof, wherein the various moieties are as described as above.

Another embodiment of the present invention are compounds or their pharmaceutically acceptable salts of Formula I represented by structural Formula II

II

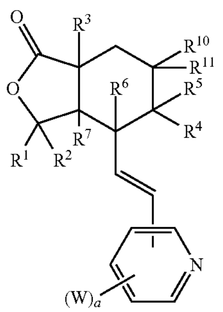

wherein $R^1$, $R^2$, $R^3$, $R^4$, $R^5$, $R^6$, $R^7$, $R^{10}$, $R^{11}$ and W are as defined in Formula I and a is 1 or 2.

Another embodiment of the present invention are compounds or their pharmaceutically acceptable salts of Formula I represented by structural Formula III

III

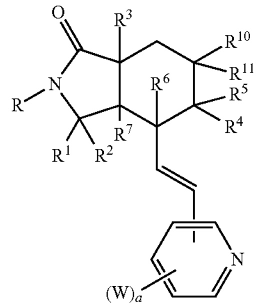

wherein R, $R^1$, $R^2$, $R^3$, $R^4$, $R^5$, $R^6$, $R^7$, $R^{10}$, $R^{11}$ and W are as defined in Formula I and a is 1 or 2.

Another embodiment of the present invention are compounds or their pharmaceutically acceptable salts of Formula I represented by structural Formula IV

IV

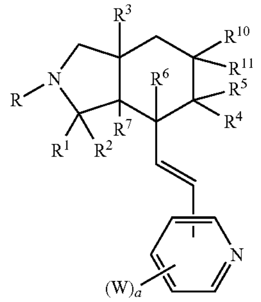

wherein R, $R^1$, $R^2$, $R^3$, $R^4$, $R^5$, $R^6$, $R^7$, $R^{10}$, $R^{11}$ and W are as defined in Formula I and a is 1 or 2.

Another embodiment of the present invention are compounds or their pharmaceutically acceptable salts of Formula I represented by structural Formula V

V

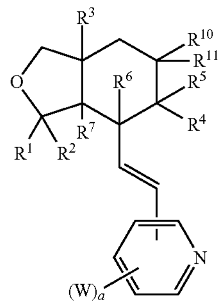

wherein $R^1$, $R^2$, $R^3$, $R^4$, $R^5$, $R^6$, $R^7$, $R^{10}$, $R^{11}$ and W are as defined in Formula I and a is 1 or 2.

Another embodiment of the present invention is a compound of any one of the embodiments of Formulae I-V above or a pharmaceutically acceptable salt thereof wherein $R^1$ is alkyl (e.g., methyl or ethyl), $R^2$ is H, $R^4$ is alkyl (e.g., methyl or ethyl), $R^5$ is H, $R^6$ is H, $R^7$ is H, W is $R^{17}$-heterocycloalkyl, $R^{17}$-aryl or $R^{17}$-heteroaryl and a is 1.

Another embodiment of the present invention is a compound of any one of the embodiments of Formulae I-V above or a pharmaceutically acceptable salt thereof wherein $R^1$ is alkyl (e.g., methyl or ethyl), $R^2$ is H, $R^4$ is alkyl (e.g., methyl or ethyl), $R^5$ is H, $R^6$ is H, $R^7$ is H, W is $R^{17}$-heterocycloalkyl, $R^{17}$-aryl or $R^{17}$-heteroaryl, a is 1, $R^{10}$ is halogen (e.g., F) and $R^{11}$ is halogen (e.g., F).

Another embodiment of the present invention is a compound of any one of the embodiments of Formulae I-V above or a pharmaceutically acceptable salt thereof wherein $R^1$ is alkyl (e.g., methyl or ethyl), $R^2$ is H, $R^4$ is alkyl (e.g., methyl or ethyl), $R^5$ is H, $R^6$ is H, $R^7$ is H, W is $R^{17}$-heterocycloalkyl, $R^{17}$-aryl or $R^{17}$-heteroaryl, a is 1, $R^{10}$ is halogen and $R^{11}$ is H or alkyl (e.g., methyl or ethyl).

Another embodiment of the present invention is a compound of any one of the embodiments Formulae I-V above or a pharmaceutically acceptable salt thereof wherein $R^1$ is alkyl (e.g., methyl or ethyl), $R^2$ is H, $R^4$ is alkyl (e.g., methyl or ethyl), $R^5$ is H, $R^6$ is H, $R^7$ is H, W is $R^{17}$-heterocycloalkyl, $R^{17}$-aryl or $R^{17}$-heteroaryl, a is 1, $R^{10}$ is —CN and $R^{11}$ is H or alkyl (e.g., methyl or ethyl).

Another embodiment of the present invention is a compound of any one of embodiments Formulae I-V above or a pharmaceutically acceptable salt thereof of any of the embodiments above wherein W is $R^{17}$-heterocycloalkyl and $R^{17}$ is 1 to 2 moieties wherein $R^{17}$ is independently hydrogen, alkyl (e.g., methyl, ethyl, propyl, butyl, sec-butyl or t-butyl), —CN, halogen, alkoxy (e.g., methoxy, ethoxy, propoxy, butoxy, sec-butoxy or t-butoxy), haloalkyl (e.g., —$CF_3$) and haloalkoxy (e.g., —$OCF_3$) and the heterocycloalkyl ring is piperidyl, pyrrolidinyl, piperazinyl, morpholinyl, thiomorpholinyl, thiazolidinyl, 1,3-dioxanyl, 1,4-dioxanyl, tetrahydrofuranyl, tetrahydrothiopyranyl or tetrahydrothiophenyl.

Another embodiment of the present invention is a compound of any one of the embodiments of Formulae I-V above or a pharmaceutically acceptable salt thereof of any of the embodiments above wherein W is $R^{17}$-phenyl and $R^{17}$ is 1 to 2 moieties wherein $R^{17}$ is independently hydrogen, alkyl (e.g., methyl, ethyl, propyl, butyl, sec-butyl or t-butyl), —CN, halogen, alkoxy (e.g., methoxy, ethoxy, propoxy, butoxy, sec-butoxy or t-butoxy), haloalkyl (e.g., —$CF_3$), —C(O)$NH_2$, —C(O)N(H)(alkyl), —C(O)N(H)(hydroxyalkyl), —C(O)N(alkyl)(alkyl) or haloalkoxy (e.g., —$OCF_3$).

Another embodiment of the present invention is a compound of any one of the embodiments of Formulae I-V above or a pharmaceutically acceptable salt thereof of any of the embodiments above wherein W is $R^{17}$-heteroaryl and $R^{17}$ is 1 to 2 moieties wherein $R^{17}$ is independently hydrogen, alkyl (e.g., methyl, ethyl, propyl, butyl, sec-butyl or t-butyl), —CN, halogen, alkoxy (e.g., methoxy, ethoxy, propoxy, butoxy, sec-butoxy or t-butoxy), haloalkyl (e.g., —$CF_3$) and haloalkoxy (e.g., —$OCF_3$) and the heteroaryl group is pyridyl, pyrazinyl, furanyl, thienyl, pyrimidinyl, pyridone, isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, quinoxalinyl, phthalazinyl, oxindolyl, naphthyridyl, pyrido[2,3]imidazolyl, imidazo[1,2-a]pyridinyl, imidazo[2,1-b]thiazolyl, benzofuranyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzoxazolyl, benzothiazolyl, pyridopyrimidinyl or 7-azaindolyl.

Another embodiment of the present invention is a compound of the embodiments of Formulae I-V above or a pharmaceutically acceptable salt thereof of any of the embodiments above wherein $R^3$ is H; —$N_3$ halogen; —OH; alkoxy; —C(O)$OR^{12}$; —C(O)N(H)($R^{26}$); —N($R^{25}$)($R^{26}$); —$SO_2R^{12}$, $R^{17}$-alkyl, $R^{17}$-cycloalkyl (e.g. cyclopropyl or cyclobutyl); $R^{17}$-phenyl; $R^{17}$-heterocycloalkyl (e.g., oxetanyl or azetidinyl) and $R^{17}$-heteroaryl (e.g., pyridyl, pyrimidyl, diazolyl, thiazolyl, oxazolyl; oxadiazolyl, triazolyl or tetrazolyl).

Another embodiment of the present invention is any of the embodiments of a compound or a pharmaceutically acceptable salt of Formulae I or II represented by structural Formula VI

VI

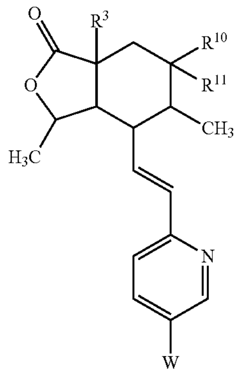

wherein $R^3$, $R^{10}$ and $R^{11}$ are defined in Formula I above and W is optionally substituted phenyl, optional substituted heterocycloalkyl, or optionally substituted heteroaryl, wherein the optionally substitutents are halogen, alkyl, haloalkyl, cyano, —OH, alkoxy, —C(O)$NH_2$, —C(O)N(H)(alkyl), —C(O)N(alkyl)(alkyl), haloalkoxy or heteroaryl optionally substituted by alkyl or halo, and wherein the heterocycloalkyl group is piperidyl, pyrrolidinyl, piperazinyl, morpholinyl, thiomorpholinyl, thiazolidinyl, 1,3-dioxanyl, 1,4-dioxanyl, tetrahydrofuranyl, tetrahydrothiopyranyl or tetrahydrothiophenyl; and the heteroaryl group is independently pyridyl, pyrazinyl, furanyl, thienyl, pyrimidinyl, pyridone, isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, quinoxalinyl, phthalazinyl, oxindolyl or indolyl.

Another embodiment is a compound of Formula VI or a pharmaceutically acceptable salt thereof wherein:

W is an optionally mono- or di substituted phenyl wherein the optional substituents are halogen, —CN, alkyl, haloalkoxy or $R^{17}$-heteroaryl (e.g., tetrazolyl);

$R^{10}$ and $R^{11}$ are both halogens (e.g., —F) and $R^3$ is H; $N_3$ halogen; —OH; alkoxy; —C(O)$OR^{12}$; —C(O)N(H)($R^{26}$); —N($R^{25}$)($R^{26}$); —$SO_2R^{12}$, $R^{17}$-alkyl, $R^{17}$-cycloalkyl (e.g. cyclopropyl or cyclobutyl); $R^{17}$-phenyl; $R^{17}$-heterocycloalkyl (e.g., oxetanyl or azetidinyl); $R^{17}$-heteroaryl (e.g., pyridyl, pyrimidyl, diazolyl, thiazolyl, oxazolyl; oxadiazolyl, triazolyl or tetrazolyl);

$R^{12}$ is H, alkyl cycloalkyl (e.g., cyclopropyl), optionally substituted phenyl or optionally substituted heteroaryl (e.g., pyridyl, pyrimidyl, diazolyl, thiazolyl, oxazolyl; oxadiazolyl, triazolyl or tetrazolyl) and the optional substituents are halogen, alkyl —CN, —$NH_2$, —N(H)(alkyl) or -(alkyl)(alkyl).

$R^{17}$ is 1 to 3 substituents and is independently H; halogen; —CN; —OH, alkoxy; —C(O)$OR^{12}$; —$NH_2$; —N(H)(alkyl); —N(alkyl)(alkyl); optionally substituted phenyl; optionally substituted heteroaryl (e.g., pyridyl, pyrimidyl, diazolyl, thiazolyl, oxazolyl, oxadiazolyl, triazolyl or tetrazolyl), wherein the optionally substituents are halogen, alkyl, —$NH_2$, —N(H)(alkyl), —N(alkyl)(alkyl) or phenyl;

$R^{25}$ is H or alkyl;

$R^{26}$ is H, —OH; alkyl; $R^{17}$-alkyl; cycloalkyl (e.g., cycloalkyl or cyclobutyl); —C(O)$R^{12}$; cycloalkyl (e.g., cyclopropyl or cyclobutyl); phenyl, heterocycloalkyl (e.g., oxetanyl) or heteroaryl (e.g., pyridyl; pyrimidyl, diazole; thiazolyl, oxazolyl and tetrazolyl); —C(S)N(H)(alkyl); —C(S)N(H)(cycloalkyl); —$S(O)_2$alkyl or —C(O)N(H)($R^{22}$); $R^{22}$ is alkyl, hydroxyalkyl or cycloalkyl.

Another embodiment is a compound of Formula VI or a pharmaceutically acceptable salt thereof wherein:

$R^{10}$ and $R^{11}$ are both halogens (e.g., —F); and $R^3$ is —$CH_2$—CN; —$CH_2OH$; —$CHNH_2$; —$CH_2$heteroaryl; —C(OH)(heteroaryl); where the heteroaryl group is pyridyl, thiazolyl, oxazolyl, oxadiazolyl, triazole or tetrazolyl) and may be optionally substituted by alkyl; or is a structure of the formula:

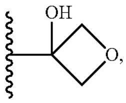,
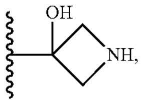, or

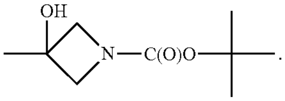.

Another embodiment is a compound of Formula VI or a pharmaceutically acceptable salt thereof wherein:

$R^{10}$ and $R^{11}$ are both halogens (e.g., —F), and $R^3$ is —$NH_2$; —N(H)(OH); —N(H)($CH_2$C(H)(OH)$CH_2$Cl); —N(H)C(O)alkyl; —N(H)C(O)phenyl, wherein the phenyl ring is optionally substituted by alkyl, halogen or —CN; —N(H)C(O)cycloalkyl (e.g., cyclopropyl or cyclobutyl); —N(H)(cycloalkyl) (e.g.; cyclopropyl); —N(H)(heterocycloalkyl) (e.g.; oxetanyl); N(H)C(O)heteroaryl (e.g., pyridyl, pyrimidyl, diazolyl, thiazolyl, oxazolyl, oxadiazolyl, triazolyl or tetrazolyl), wherein said heteroaryl group is optionally substituted with alkyl or halogen; or —N(H)C(S)(cycloalkyl) (e.g., cyclopropyl or cyclobutyl).

Another embodiment is a compound of Formula VI or a pharmaceutically acceptable salt thereof wherein:

$R^{10}$ and $R^{11}$ are both halogens (e.g., —F); and $R^3$ is —N(H)(alkyl); —N(Me)(Me); —N(H)(—$CH_2$-cycloalkyl); —N(H)(—$CH_2$-heteroaryl), where the heteroaryl group is pyridyl, pyrimidyl, diazolyl, thiazolyl, oxazolyl, oxadiazolyl, triazolyl or tetrazolyl).

As used above, and throughout this disclosure, the following terms, unless otherwise indicated, shall be understood to have the following meanings:

"Patient" or "subject" includes both humans and animals.

"Mammal" means humans and other mammalian animals.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Dihydroxyalkyl" refers to an alkyl chain substituted by two hydroxy groups on two different carbon atoms.

"Halo" refers to fluorine, chlorine, bromine or iodine radicals. Preferred are fluoro, chloro or bromo, and more preferred are fluoro and chloro.

"Halogen" means fluorine, chlorine, bromine, or iodine. Preferred are fluorine, chlorine and bromine.

"Haloalkyl" means a halo-alkyl-group in which the alkyl group is as previously described. The bond to the parent moiety is through the alkyl. Non-limiting examples of suitable haloalkyl groups include fluoromethyl, difluoromethyl, —$CH_2CF_3$, —$CH_2CHF_2$ or —$CH_2CH_2F$.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. The alkenyl group can be substituted by one or more substituents independently selected from the group consisting of halo, alkyl, aryl, cycloalkyl, cyano and alkoxy. Non-limiting examples of suitable alkenyl groups include ethenyl, propenyl, n-butenyl, 3-methylbut-enyl and n-pentenyl.

Where an alkyl or alkenyl chain joins two other variables and is therefore bivalent, the terms alkylene and alkenylene, respectively, are used.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more ring system substituents which may be the same or different. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more ring system substituents which may be the same or different. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Aryl" means an aromatic monocyclic or multicyclic ring system comprising about 6 to about 14 carbon atoms, preferably about 6 to about 10 carbon atoms. Non-limiting examples of suitable aryl groups include phenyl, naphthyl, indenyl, tetrahydronaphthyl and indanyl. "Arylene" means a bivalent phenyl group, including ortho, meta and para-substitution.

"Arylalkenyl" means an aryl-alkenyl group in which the aryl and alkenyl portions are as previously described.

"Arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl.

"Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocycloalkyl root name means that at least a nitrogen, oxygen or sulfur atom respectively is present as a ring atom. Any —NH in a heterocycloalkyl ring may exist protected such as, for example, as an —N(Boc), —N(CBz), —N(Tos) group and the like; such protections are also considered part of this invention. The nitrogen or sulfur atom of the heterocycloalkyl ring can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,3-dioxanyl, 1,4-dioxanyl, tetrahydrofuranyl, tetrahydrothiopyranyl, tetrahydrothiophenyl, lactam, lactone, and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, 2-oxazolinyl, 2-thiazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination, provided that the rings do not include adjacent oxygen and/or sulfur atoms. N-oxides of the ring nitrogens are also included, as well as compounds wherein a ring nitrogen is substituted by an alkyl group to form a quaternary amine. Preferred heteroaryls contain about 5 to about 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, quinoxalinyl, phthalazinyl, oxindolyl, naphthyridyl (e.g., 1,5 or 1,7), pyrido[2,3]imidazolyl, imidazo[1,2-a]pyridinyl, imidazo[2,1-b]thiazolyl, benzofuranyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzoxazolyl, benzothiazolyl, pyridopyrimidinyl, 7-azaindolyl and the like. The term "heteroaryl" also refers to partially saturated heteroaryl moieties such as, for example, tetrahydroisoquinolyl, tetrahydroquinolyl and the like. All positional isomers are contemplated, e.g., 2-pyridyl, 3-pyridyl and 4-pyridyl.

It should be noted that in heterocycloalkyl or heterocyclenyl ring systems of this invention, there are no hydroxyl groups on carbon atoms adjacent to a N, O or S, as well as there are no N or S groups on carbon adjacent to another heteroatom. Thus, for example, in the ring:

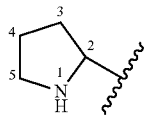

there is no —OH attached directly to carbons marked 2 and 5.

It should also be noted that tautomeric forms such as, for example, the moieties:

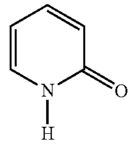

and

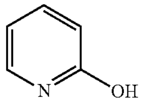

are considered equivalent in certain embodiments of this invention.

"Amino" means a —$NH_2$ group.

"Alkylamino" means an alkyl-amino group in which the alkyl group is as previously described. The bond to the parent moiety is through the amino.

"Alkylaminoalkyl" means an alkyl-amino-alkyl group in which the alkyl groups are as previously described. The bond to the parent moiety is through the alkyl.

"Heteroarylalkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heteroarylalkenyl" means a heteroaryl-alkenyl group in which the heteroaryl and alkenyl are as previously described. Preferred heteroarylalkenyl contain a lower alkenyl group. The bond to the parent moiety is through the alkenyl group.

"Heterocycloalkyloxy" means a heterocycloalkyl-O— group in which the heterocycloalkyl group is as previously described. The bond to the parent moiety is through the ether atom.

"Aminoalkyl" means an amino-alkyl group in which the alkyl group is as previously described. The bond to the parent moiety is through the alkyl.

"Alkenyloxy" means an alkenyl-O— group in which the alkenyl group is as previously described. The bond to the parent moiety is through the ether oxygen.

"Alkynyloxy" means an alkynyl-O— group in which the alkenyl group is as previously described. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Heteroaryloxy" means an heteroaryl-O— group in which the heteroaryl group is as previously described. The bond to the parent moiety is through the ether oxygen.

"Cycloalkenyloxy" means a cycloalkenyl-O— group in which the cycloalkenyl group is as previously described. The bond to the parent moiety is through the ether atom.

"Cycloalkyloxy" or "cycloalkoxy" means a cycloalkyl-O— group in which the cycloalkyl group is as previously described. The bond to the parent moiety is through the ether atom.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

"Effective amount" or "therapeutically effective amount" is meant to describe an amount of compound or a composition of the present invention effective as PAR-1 or thrombin receptor antagonists, thereby producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

In this application, unless otherwise indicated, whenever there is a structural formula provided, such as those of Formulae I to VI, this formula is intended to encompass all forms of a compound such as, for example, any solvates, hydrates, stereoisomers, tautomers, co-crystals, polymorphs etc.

Compounds of Formula I, and salts, solvates, co-crystals and prodrugs thereof, may exist in their tautomeric form (for example, as an amide or imino ether). All such tautomeric forms are contemplated herein as part of the present invention.

Prodrugs, solvates and co-crystals of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

A co-crystal is a crystalline superstructure formed by combining an active pharmaceutical intermediate with an inert molecule and provides crystallinity to the combined form. Co-crystals are often made between a dicarboxylic acid such as fumaric acid, succinic acid etc. and a basic amine such as the one represented by compound I of this invention in different proportions depending on the nature of the co-crystal. (Remenar, J. F. et. al. *J Am. Chem. Soc.* 2003, 125, 8456).

All stereoisomers (for example, geometric isomers, optical isomers and the like) of the present compounds (including those of the salts, solvates, co-crystals and prodrugs of the compounds as well as the salts and solvates, co-crystals of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Typically preferred compounds of the present invention have the following stereochemistry:

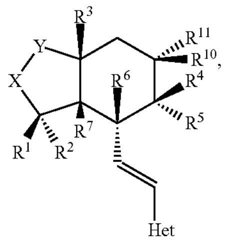

with compounds having that absolute stereochemistry being more preferred.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically-labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

As discussed above, the compounds of Formula I may be used to treat, ameliorate or prevent conditions associated with inhibiting the PAR-1 receptor. In addition to the conditions mentioned above, other conditions could include migraine, erectile dysfunction, rheumatoid arthritis, rheumatism, astrogliosis, a fibrotic disorder of the liver, kidney, lung or intestinal tract, systemic lupus erythematosus, multiple sclerosis, osteoporosis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy, malignant tumors, neurodegenerative and/or neurotoxic diseases, conditions or injuries, Alzheimer's disease, an inflammatory disease or condition, asthma, glaucoma, macular degeneration, psoriasis, endothelial dysfunction disorders of the liver, kidney or lung, inflammatory disorders of the lungs and gastrointestinal tract, respiratory tract disease or condition, radiation fibrosis, endothelial dysfunction, periodontal diseases or wounds, or a spinal cord injury, or a symptom or result thereof, viral infections, including infections from human respiratory syncytial virus (hRSV), human metapneumovirus (hMPV) and influenza virus type A, as well as other disorders in which thrombin and its receptor play a pathological role.

In addition to their PAR-1 receptor antagonist properties, the compounds of Formula I or the pharmaceutically acceptable salts might be expected to be used to treat, ameliorate or prevent one or more conditions associated with inhibiting the $CB_2$ receptor by administering at least one compound of Formula I or a pharmaceutically acceptable salt thereof to a mammal in need of such treatment. Conditions might include, for example, rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis.

In another embodiment, compounds of the present invention might be expected to be useful in a method for treating, ameliorating or preventing radiation- and/or chemical-induced toxicity in non-malignant tissue in a patient comprising administering a therapeutically effective amount of at least one compound of Formula I or a pharmaceutically acceptable salt thereof. In particular, the radiation- and/or chemical-induced toxicity is one or more of intestinal fibrosis, pneumonitis, and mucositis. In one embodiment, the radiation- and/or chemical-induced toxicity is intestinal fibrosis. In another embodiment, the radiation- and/or chemical-induced toxicity is oral mucositis. In yet another embodiment, the radiation- and/or chemical-induced toxicity is intestinal mucositis, intestinal fibrosis, intestinal radiation syndrome, or pathophysiological manifestations of intestinal radiation exposure.

The present invention might also be expected to provides for methods for reducing structural radiation injury in a patient that will be exposed, is concurrently exposed, or was exposed to radiation and/or chemical toxicity, comprising administering a therapeutically effective amount of at least one compound of Formula I or a pharmaceutically acceptable salt thereof. The present invention might also be expected to provide for methods for reducing inflammation in a patient that will be exposed, is concurrently exposed, or was exposed to radiation and/or chemical toxicity, comprising administering a therapeutically effective amount of at least one compound of Formula I or a pharmaceutically acceptable salt thereof. The present invention might also be expected to provide for methods for adverse tissue remodeling in a patient that will be exposed, is concurrently exposed, or was exposed to radiation and/or chemical toxicity, comprising administering a therapeutically effective amount of at least one compound of Formula I or a pharmaceutically acceptable salt thereof. The present invention might also be expected to provide for methods for reducing fibroproliferative tissue effects in a patient that will be exposed, is concurrently exposed, or was exposed to radiation and/or chemical toxicity, comprising administering a therapeutically effective amount of at least one compound of Formula I or a pharmaceutically acceptable salt thereof.

The present invention might also be expected to provides for methods useful for treating a cell proliferative disorder in a patient suffering therefrom comprising administering a therapeutically effective amount of at least one compound of Formula I or a pharmaceutically acceptable salt thereof. In one embodiment, the cell proliferative disorder is pancreatic cancer, glioma, ovarian cancer, colorectal and/or colon cancer, breast cancer, prostate cancer, thyroid cancer, lung cancer, melanoma, or stomach cancer. In one embodiment, the glioma is an anaplastic astrocytoma. In another embodiment, the glioma is a glioblastoma multiforme.

As used above, the term inflammatory disease or condition includes irritable bowel syndrome, Crohn's disease, nephritis or a radiation- or chemotherapy-induced proliferative or inflammatory disorder of the gastrointestinal tract, lung, urinary bladder, gastrointestinal tract or other organ. The term respiratory tract disease or condition includes reversible airway obstruction, asthma, chronic asthma, bronchitis or chronic airways disease. "Cancer" includes renal cell carcinoma or an angiogenesis related disorder. "Neurodegenerative disease" includes Parkinson's disease, amyotropic lateral sclerosis, Alzheimer's disease, Huntington's disease or Wilson's disease.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically acceptable carrier. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The amount and frequency of administration of the compound of this invention and/or their pharmaceutically acceptable salts will be regulated according to the judgment of the attending clinician considering such factors as age, condition and size of the patient as well as the severity of the symptoms being treated.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing" or "prevention" are used herein to refer to administering a compound before the onset of clinical symptoms.

The compounds of this invention may also be useful in combination (administered together or sequentially) with one or more therapeutic agents, such as, for example, another cardiovascular agent. Cardiovascular agents that could be used in combination with the compounds for Formula I or their pharmaceutically acceptable salts include drugs that have anti-thrombotic, anti-platelet aggregation, antiatherosclerotic, antirestenotic and/or anti-coagulant activity. Such drugs are useful in treating thrombosis-related diseases including thrombosis, atherosclerosis, restenosis, hypertension, angina pectoris, arrhythmia, heart failure, myocardial infarction, glomerulonephritis, thrombotic and thromboembolic stroke, peripheral vascular diseases, other cardiovascular diseases, cerebral ischemia, inflammatory disorders and cancer, as well as other disorders in which thrombin and its receptor play a pathological role. Suitable cardiovascular agents are selected from the group consisting of thromboxane A2 biosynthesis inhibitors such as aspirin; thromboxane antagonists such as seratrodast, picotamide and ramatroban; adenosine diphosphate (ADP) inhibitors such as clopidogrel; cyclooxygenase inhibitors such as aspirin, meloxicam, rofecoxib and celecoxib; angiotensin antagonists such as valsartan, telmisartan, candesartran, irbesartran, losartan and eprosartan; endothelin antagonists such as tezosentan; phosphodiesterase inhibitors such as milrinoone and enoximone; angiotensin converting enzyme (ACE) inhibitors such as captopril, enalapril, enaliprilat, spirapril, quinapril, perindopril, ramipril, fosinopril, trandolapril, lisinopril, moexipril and benazapril; neutral endopeptidase inhibitors such as candoxatril and ecadotril; anticoagulants such as ximelagatran, fondaparin and enoxaparin; diuretics such as chlorothiazide, hydrochlorothiazide, ethacrynic acid, furosemide and amiloride; platelet aggregation inhibitors such as abciximab and eptifibatide; and GP IIb/IIIa antagonists.

Other possible combinations might include lipid lowering agents (e.g., simvastatin, lovastatin, pravastatin, atorvastatin rosuvastatin, pitavastatin, ezetimibe); niacin in immediate-release or controlled release forms, and particularly in niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds (e.g., muraglitazar, glipizide, stigliptin, metformin, rosiglitazone statins, e.g., simvastatin, atorvastatin and rosuvastatin), PCSK9 inhibitors, e.g. antibodies—REGN727, AMG-145, RN316, RG7652; and small molecule inhibitors and CETP inhibitors, e.g., anacetrapib, evacetrapib, etc. Other possible combinations include AMPK agonists (e.g., ETC-1002); glucagon receptor antagonists; Lp-PLA2 inhibitors (e.g., darapladib) and anti-IL-1 beta antibodies (canakinumab).

The dosage of the cardiovascular agent can be determined from published material, and may range from 1 to 1000 mg per dose.

A more preferred embodiment is combinations comprising an effective amount of a compound of Formula I or a pharmaceutically acceptable salt thereof and an ADP antagonist and/or cyclooxygenase inhibitor.

A preferred combination are comprises an effective amount of a compound according to Formula I or a pharmaceutically acceptable salt thereof and aspirin, ticagrelor, cangrelor, clopidogrel (either as a free base or as a pharmaceutically acceptable salt, such as its bisulfate salt), prasugrel, ticlopidine or fragmin.

A more preferred embodiment is combinations comprising an effective amount of a compound of Formula I or a pharmaceutically acceptable salt thereof and clopidogrel (either as a free base or as a pharmaceutically acceptable salt, such as its bisulfate salt) and/or aspirin.

Other therapeutic agents could include drugs that are known and used in the treatment of inflammation, rheumatism, asthma, glomerulonephritis, osteoporosis, neuropathy and/or malignant tumors, angiogenesis related disorders, cancer, disorders of the liver, kidney and lung, melanoma, renal cell carcinoma, renal disease, acute renal failure, chronic renal failure, renal vascular homeostasis, glomerulonephritis, chronic airways disease, bladder inflammation, neurodegenerative and/or neurotoxic diseases, conditions, or injuries, radiation fibrosis, endothelial dysfunction, periodontal diseases and wounds. Further examples of therapeutically effective agents which may be administered in combination with a compound of Formula I or a pharmaceutically acceptable salt thereof include resistance factors for tumor cells towards chemotherapy and proliferation inhibitors of smooth muscle cells, endothelial cells, fibroblasts, kidney cells, osteosarcoma cells, muscle cells, cancer cells and/or glial cells.

For treating and/or preventing radiation- and/or chemical-induced toxicity in non-malignant tissue, the present invention includes administering to a patient in need of such treatment an effective amount of a combination of one or more compounds of formula I and one or more radiation-response modifiers selected from the group consisting of Kepivance™ (palifermin), L-glutamine, teduglutide, sucralfate mouth rinses, iseganan, lactoferrin, mesna and trefoil factor.

For treating a cell proliferative disorder the present invention includes administering to a patient in need of such treatment an effective amount of a combination of one or more compounds of Formula I or a pharmaceutically acceptable salt thereof and another antineoplastic agent. In one embodiment, the other antineoplastic agent is temozolomide and the cell proliferative disorder is glioma. In another embodiment, the other antineoplastic agent is interferon and the cell proliferative disorder is melanoma. In one embodiment, the other antineoplastic agent is PEG-Intron (peginterferon alpha-2b) and the cell proliferative disorder is melanoma.

Pharmaceutical compositions comprising a therapeutically effective amount of a combination of at least one compound of Formula I or a pharmaceutically acceptable salt thereof and a radiation-response modifier in a pharmaceutically acceptable carrier are also provided.

Pharmaceutical compositions comprising a therapeutically effective amount of a combination of at least one compound of Formula I or a pharmaceutically acceptable salt thereof and an antineoplastic agent in a pharmaceutically acceptable carrier are also provided.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A.

Gennaro (ed.), *The Science and Practice of Pharmacy,* 20th Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

Moreover, one skilled in the art would have resources such as *Chemical Abstracts* or *Beilstein* at his or her disposal to assist in preparing a specific compound.

One skilled in the art will recognize that one route will be optimized depending on the choice of appendage substituents. Additionally, one skilled in the art will recognize that in some cases the order of steps has to be controlled to avoid functional group incompatibility.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme and in the preparations and examples described below.

Where NMR data are presented, $^1$H spectra were obtained, for example, on either a Varian VXR-200 (200 MHz, $^1$H), Varian Gemini-300 (300 MHz), Varian Mercury VX-400 (400 MHz), or Bruker-Biospin AV-500 (500 MHz), and are reported as ppm with number of protons and multiplicities indicated parenthetically. Where LC/MS data are presented, analyses was performed, for example, using an Applied Biosystems API-100 mass spectrometer and C18 column, 10-95% $CH_3CN$—$H_2O$ (with 0.05% TFA) gradient. The observed parent ion is given.

Throughout the synthetic schemes, abbreviations are used with the following meaning unless otherwise indicated:

Aq.=aqueous; Bn=benzyl; BOC=tert-butyloxycarbonyl; m-CPBA=m-chloroperoxybenzoic acid; CELITE=diatomaceous earth filtering aid; DBU=1,8-Diazabicyclo[5.4.0]undec-7-ene; DCC=N,N'-bicyclohexylcarbodiimide; DCM=dichloromethane; DAST=diethylaminosulfur trifluoride; DMAP=4-dimethylamino pyridine; DMF=dimethylformamide; DMSO=dimethylsulfoxide; DIEA=N,N-Diisopropylethylamine or Hünig's base; EtOH=ethanol; EtOAc=ethyl acetate; HATU=O-(7-Azabenzotriazol-1-yl)-N,N,N',N'-tetramethyluronium hexafluorophosphate; Hex=Hexanes; HOBt=hydroxybenzotriazole; KHMDS=potassium hexamethyldisilazide; LiHMDS=lithium hexamethyldisilazide; MeOH=methanol; MeI=methyl iodide; MPLC=medium pressure liquid chromatography; MsCl=methane sulfonyl chloride; rt=room temperature TEA=triethanolamine; TFA=trifluoroacetic acid; THF=tetrahydrofuran; TLC=thin layer chromatography Bicyclic himbacine derivatives are known in the literature and may be prepared by a variety of methods known by those skilled in the art; see, for example, U.S. Pat. No. 6,063,847; U.S. Pat. No. 6,645,987 and U.S. Pat. No. 7,304,087. Typically, the bicyclic "top" portion of the compound is formed and then the bottom "tail" portion is added by a coupling reaction; the resulting compound is then subsequently modified (if necessary). Schemes I and II summarize two possible methods that could be used to prepare the bicyclic intermediate. Other similar methods are known in the art.

Scheme 1

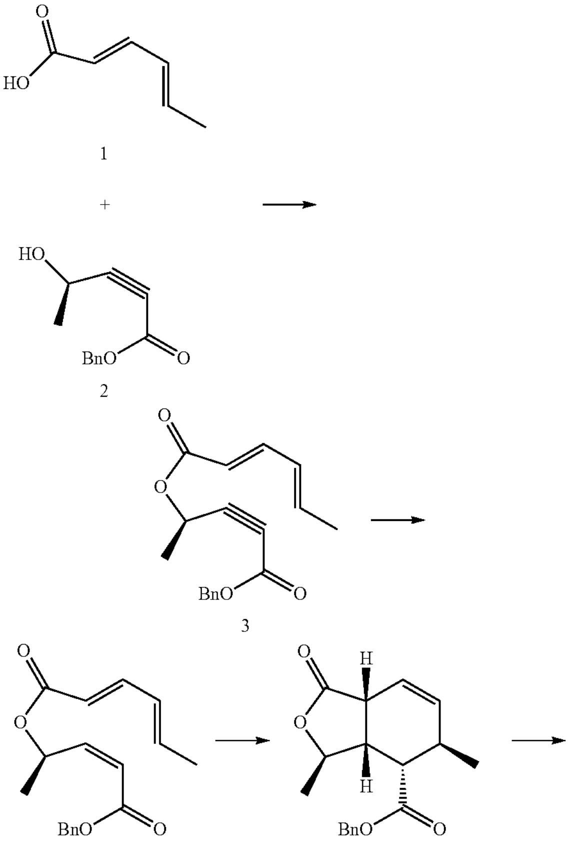

1

+

2

3

4

5

-continued

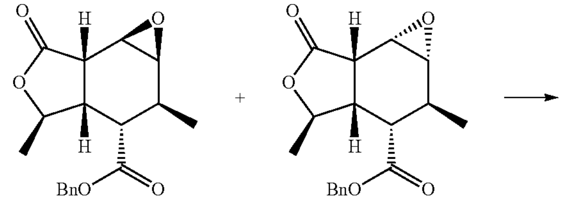

6 7

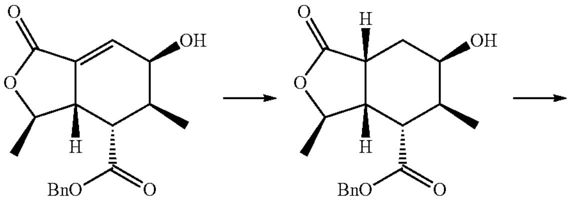

8 9

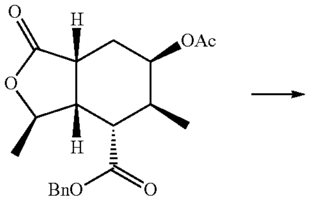

10

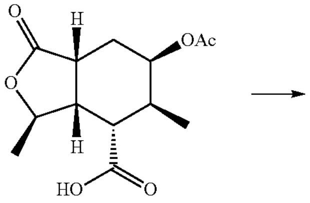

11

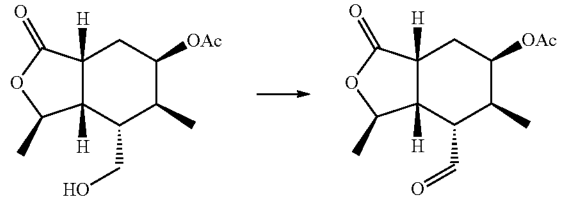

12 Intermediate 1

Scheme 1 describes a method for preparing the lactone Intermediate 1. Coupling the acid 1 with alcohol 2 by using standard condition such as using reagents such as DCC gives ester 3. Reduction of the alkyne 3 using Lindler catalyst provides the olefin 4, which was cyclized to the lactone 5. Epoxidation of 5 using reagents such as m-chloro perbenzoic acid gives the epoxides 6 and 7, which were subsequently converted to the alcohol 8 using bases such as DBU and finally reduced with standard reducing agents such as sodium borohydride in the presence of nickel dichloride to provide 9. Protection of the alcohol 9, hydrolysis of the benzyl ester, reduction of the acid and oxidation of the resulting primary alcohol gave the acetate 10, acid 11, primary alcohol 12 and aldehyde 13, respectively.

Scheme 2

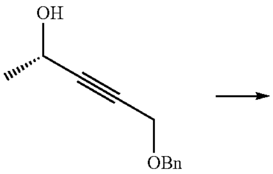

14

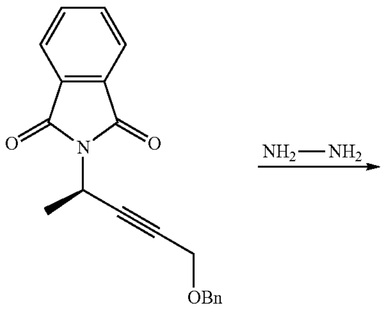

15

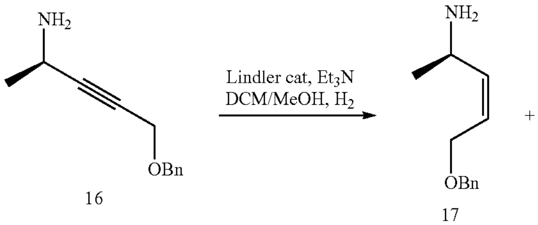

16 17

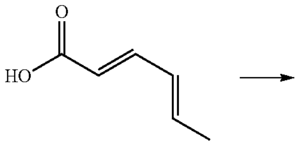

18

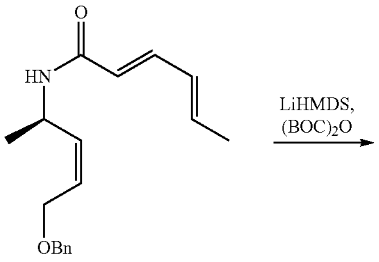

19

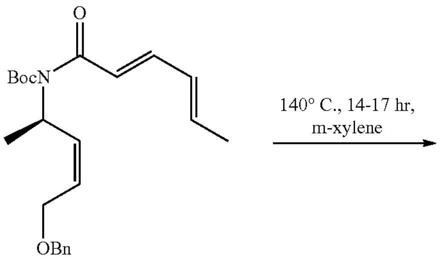

20

-continued

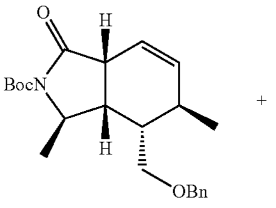

21

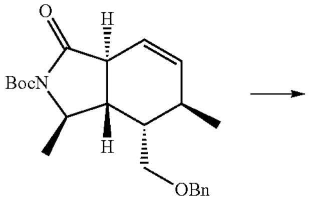

22

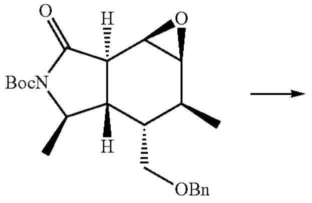

23

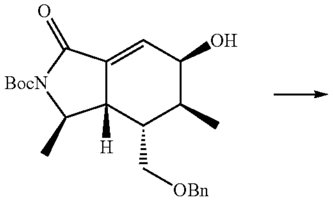

24

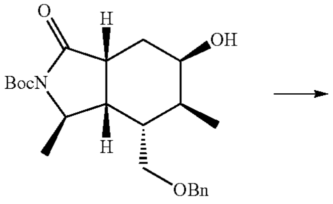

25

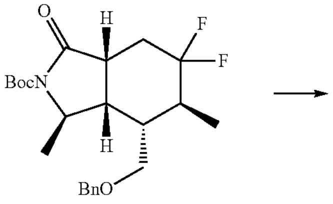

26

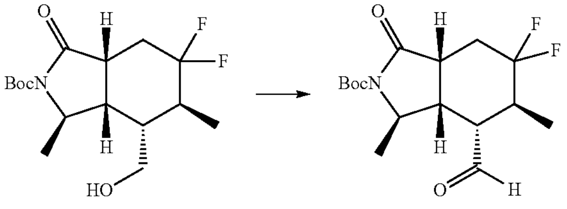

27

Intermediate 2

Scheme 2 describes a method for preparing the lactam Intermediate 2. The secondary alcohol 14 was converted to the amine 16 by using phthalamide followed by hydrazine. Reduction of the alkyne with Lindlar catalyst, coupling with acid 18, protection of the amine and cyclization as shown in Scheme 2 gave 21 and 22. Conversion of the olefins 21 and 22 to the alcohol 25 was done by using the methods shown for the lactone series in Scheme 1. Oxidation of the alcohol 25 by using reagents such as Des Martin periodinate gives ketone 26 with was treated with DAST to form the difluoro analog 28.

Scheme 3

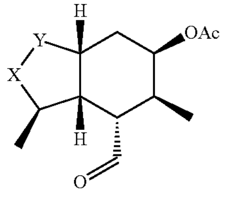

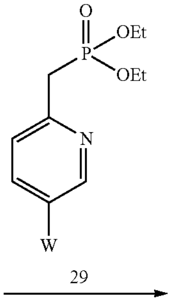

29

13

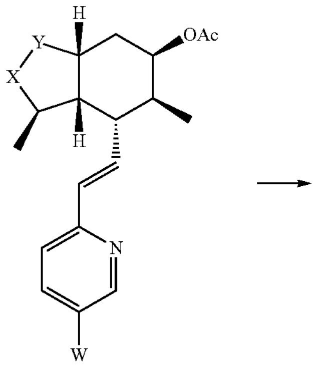

30

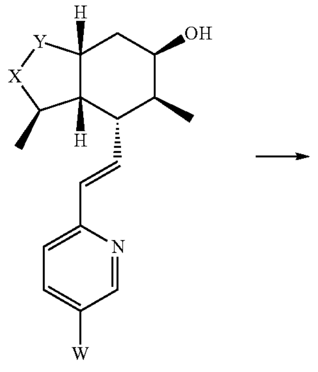

31

-continued

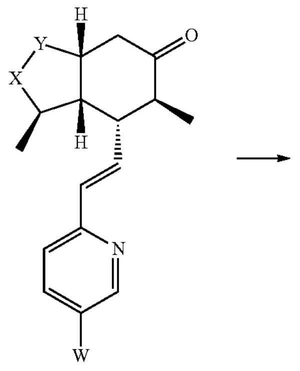

32

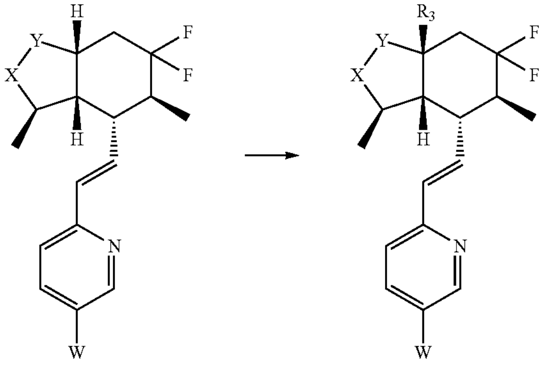

33 34

Scheme 3 described a method for coupling aldehyde intermediates such as Intermediate I or Intermediate 2 with phosphonate esters such as 29. Bicyclic aldehyde 13a could be coupled with dialkyl pyridinyl methyl phosphonate 28 to provide 30. Hydrolysis of the acetate 30 to alcohol 31, oxidation of the resulting alcohol to ketone 32 using standard methods and treatment of the ketone 32 with fluorinating agents such as DAST provides 33. Alternatively, the fluorinated aldehyde 13b could be directly coupled with phosphonate 29 to provide 33.

Further modification of 33 by generating anion of 33 using bases such as LHMDS and treatment of the resulting anion with nucleophilic reagents gives 34.

The following is illustrative of the processes to make the intermediates used in the example below:

Intermediate 1

Intermediate 1

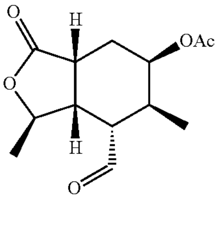

Step A: Preparation of Compound 3

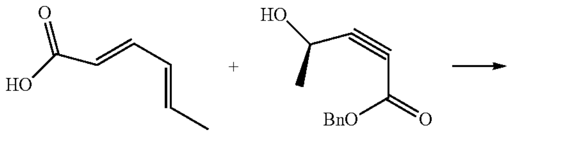

1 2

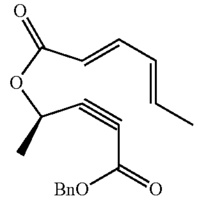

3

To a mixture of 1 (33 g, 0.294 mol, 1.2 equiv.) and 2 (50 g, 0.245 mol) in 500 mL dichloromethane was added DCC (61 g, 0.29 mol., 1.2 equiv.) and the resulting solution was stirred for 10 minutes then was added DMAP (0.1 equiv., 3 g, 0.023 mol). The reaction mixture was stirred for 2 hrs or until the reaction completed. The reaction mixture was diluted with 1 liter ether, filtered and the filtrate was washed with saturated aq. $NaHCO_3$ followed by 1N HCl and brine. The organic layer was dried, evaporated, and purified using 5% ethyl acetate in hexanes to yield 3.

Step B: Preparation of Compound 4

4

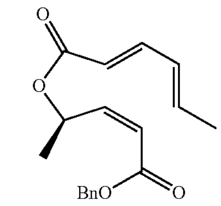

A suspension of compound 3 (28.8 g, 96 mmol), quinoline (0.2 equiv., 2.5 g, 19 mmol) and Lindlar catalyst (2.8 g, 10% by wt) in 300 mL THF was stirred under hydrogen atmosphere. The progress of the reaction was monitored by TLC. Once the reaction completed (~after 3 hr) the reaction mixture was filtered through a pad of CELITE and evaporated to yield 4 as oil.

Step C: Preparation of Compound 5

5

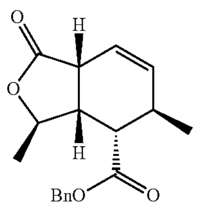

29 g of 4 was dissolved in 500 mL of xylene and the resulting mixture was heated at 185° C. in a sealed tube for 4 hrs or until the reaction completed. The reaction mixture was evaporated to dryness and dissolved in 400 mL dichloromethane and treated with DBU (0.2 equiv.) and the resulting solution was stirred for 1 hr or until the reaction completed. The reaction mixture was evaporated to dryness and purified using 15% ethyl acetate in hexanes to obtain 5. NMR ($CDCl_3$) δ 7.36 (m, 5H), 5.75 (m, 1H), 5.63 (m, 1H), 5.18 (m, 2H), 4.54 (m, 1H), 3.30 (m, 1H), 2.73 (m, 1H), 2.63 (m, 1H), 2.45 (m, 1H), 1.16 (d, J=6.0 Hz, 3H), 1.05 (J=6.6 Hz, 3H).

Step D: Preparation of Compounds 6 and 7

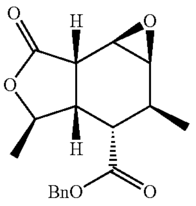

6

+

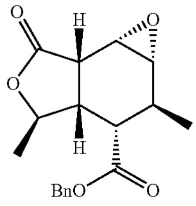

7

To a solution of alkene 5 (5.6 g, 18.7 mmol) in 100 mL dichloromethane was added mCPBA (3 equiv., 54 mmol) portion wise at 0° C., and the resulting solution stirred for 30 minutes at 0° C. Then the ice bath was removed and the resulting solution was stirred at room temperature for 6 hrs or until reaction completed. The reaction mixture was poured slowly into the ice cooled solution of saturated sodium sulfite (~3-5 equiv. $Na_2SO_3$) and stirred for 20 minutes. The resulting biphasic solution was poured carefully into a beaker containing a solution of 20% aq. $Na_2CO_3$ (final pH of the solution needs to be basic). The resulting mixture was extracted with ether (three times), the organic layer was dried, concentrated and purified using 15% ethyl acetate in hexanes to obtain 6 and 7 in 3.3:1 ratio. NMR of the epoxide 6: NMR ($CDCl_3$) δ 7.35 (m, 5H), 5.11 (m, 2H), 4.55 (m, 1H), 3.34 (m, 1H), 3.23 (m, 1H), 3.17 (m, 1H), 2.66 (m, 1H), 2.46 (m, 2H), 1.16 (d, J=6.4 Hz, 3H), 1.11 (J=6.0 Hz, 3H). NMR of the epoxide 7: NMR ($CDCl_3$) δ 7.36 (m, 5H), 5.13 (m, 2H), 4.58 (m, 1H), 3.48 (m, 1H), 3.07 (m, 2H), 2.53 (m, 2H), 2.30 (m, 1H), 1.14 (d, J=6.8 Hz, 3H), 1.078 (J=6.0 Hz, 3H).

Step E: Preparation of Compound 8

8

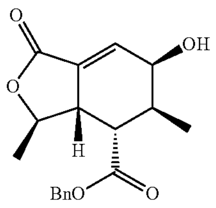

To a solution of the epoxide 6 (20 g, 66 mmol) in 200 mL dichloromethane was added DBU (33 mmol, 0.5 equiv.) and resulting solution was stirred at room temperature for 2 hr or until the reaction completed. The reaction mixture was diluted with ether and washed with 1N HCl and brine. The organic layer was dried, concentrated and evaporated to yield. NMR ($CDCl_3$) δ 7.32 (m, 5H), 6.65 (m, 1H), 5.08 (m, 2H), 4.64 (m, 1H), 4.37 (m, 1H), 3.06 (m, 1H), 2.77 (m, 1H), 2.51 (m, 1H), 1.38 (d, J=6.0 Hz, 3H), 1.08 (J=7.2 Hz, 3H).

Step F: Preparation of Compound 9

9

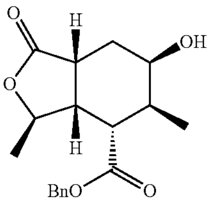

To a solution of 8 (19.9 mmol, 63 mmol) in the mixture of THF-methanol (375 mL THF and 75 mL methanol) was added $NiCl_2.6H_2O$ (95 mmol, 1.5 equiv.) at 0° C. To this reaction mixture was added $NaBH_4$ (4 equiv., 254 mmol, 9.6 g) over the period of 20 minutes. The reaction mixture was stirred at 0° C. for 15 minutes or until the reaction completed. The reaction mixture was filtered through a pad of CELITE, washed the CELITE with methanol and the resulting organic layer was evaporated to dryness and dissolved in 200 mL dichloromethane, washed with aq. $NH_4Cl$, brine, dried and concentrated to yield 9. NMR ($CD_3OD$) δ7.32 (m, 5H), 4.8 (m, 2H, under methanol signals), 4.7 (m, 1H), 3.87 (m, 1H), 2.83 (m, 2H), 2.50 (m, 1H), 1.99 (m, 2H), 1.7 (m, 1H), 1.14 (d, J=5.6 Hz, 3H), 0.948 (J=6.8 Hz, 3H).

Step G: Preparation of Compound 10

10

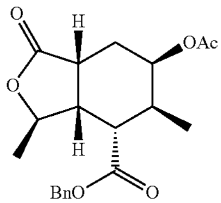

To a solution of 9 (8 g, 25 mmol) in 100 mL dichloromethane was added acetic anhydride (1.5 equiv.) followed by triethyl amine (1.5 equiv.) and catalytic amount of DMAP and the resulting solution was stirred for 2 hrs or until the reaction completed. The reaction mixture was diluted with ether and washed with aq. $NaHCO_3$, brine, dried, concentrated and taken to the next step without purification.

Step H: Preparation of Compound 11

11

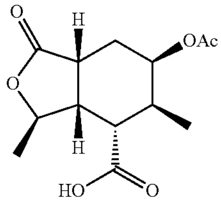

To the solution of 10 (~9 g) in ethyl acetate was added Pd/C (800 mg) and resulting solution was stirred under hydrogen until for 1 hr or until the reaction completed. The reaction mixture was filtered through a pad of CELITE and concentrated to yield 11.

Step I: Preparation of Compound 12

12

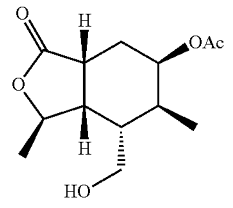

To this acid 11 in 100 mL dichloromethane was added 4.2 mL of $(COCl)_2$ and drop of DMF and the resulting solution was stirred for 2 hr or until the reaction completed. The reaction mixture was evaporated dryness and the crude acid chloride was taken to the next step without any purification. To this acid chloride (~25 mmol) in 150 mL THF was added 15 g of $LiAlH(OtBu)_3$ in several portions at 0° C. The resulting mixture was stirred for 2 hr or until the reaction completed. The reaction mixture was poured into ice cold aqueous of $H_2SO_4$ and extracted with ethyl acetate, the organic layer was dried, evaporated, and purified using 50% ethyl acetate in hexanes to yield 12. NMR δ 5.09 (m, 1H), 4.73 (m, 1H), 3.76 (m, 2H), 2.73 (m, 1H), 2.45 (m, 1H), 2.21 (m, 1H), 2.0 (m, 4H), 1.86 (m, 1H), 1.61 (m, 1H), 1.55 (d, J=6 Hz, 3H), 0.98 (d, J=6.8 Hz, 3H).

Step J: Preparation of Intermediate 1

Intermediate 1

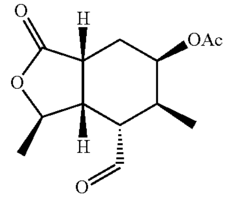

To a solution of $(COCl)_2$ (11.7 mmol, 1.5 equiv., 0.98 mL) in 40 mL dichloromethane was added a solution of DMSO (1.1 mL, 15.6 mmol) in 5 mL dichloromethane at −78° C. The resulting solution was stirred at −78° C. for 5 minutes. Then a solution of alcohol 12 (2 g, 7.8 mmol, 1 equiv.) in 10 mL dichloromethane was added slowly and the resulting mixture was stirred for 30 minutes. At this time triethyl amine (4 equiv., 4.3 mL) was added and resulting solution was stirred was allowed to warm to room temperature over 30 minutes. The reaction mixture then was transferred to sep funnel and 50 mL water was added. The phase was separated and the aqueous layer was extracted three times with diethyl ether (3×100 mL). The combined organic phases were washed successively with 20 mL of aqueous 1% hydrochloric acid, 20 mL of water, 20 mL of aqueous 5% sodium bicarbonate, and 20 mL of saturated aqueous NaCl. The organic layer was dried over $MgSO_4$, and the solvent was removed under reduced pressure, to provide 2 g of the Intermediate 1 in quantitative yield. This crude aldehyde was taken to the next step without any purification.

Intermediate 2

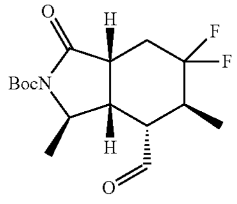

Step A: Preparation of Compound 15

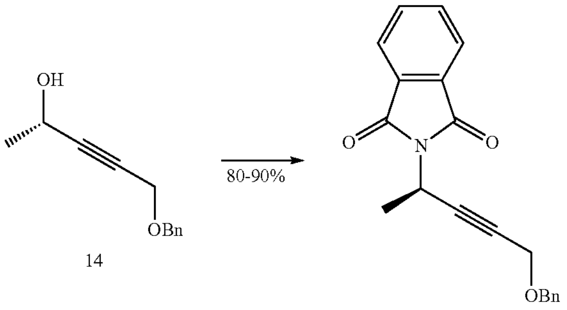

14

15

To a solution of alcohol 14 (5 g, 26 mmol) in 130 mL THF were added phthalimide (1.5 equiv., 39 mmol, 5.8 mg), $PPh_3$ (1.1 equiv., 28.6 mmol, 7.4 g) and the resulting solution was cooled to 0° C. and diisopropyl azodicarboxylate (1.2 equiv., 31 mmol, 6.1 mL) was added slowly. The reaction mixture was slowly warmed to room temperature and stirred for 18 hrs, whereupon TLC indicated the complete consumption of the starting material. The reaction mixture was evaporated to dryness, diluted with ethyl acetate, washed with saturated $NaHCO_3$, then with brine. The organic layer was separated, dried with $MgSO_4$, evaporated and column chromatographed using 0 to 100% ethyl acetate in hexanes to provide 15.

Step B: Preparation of Compound 16

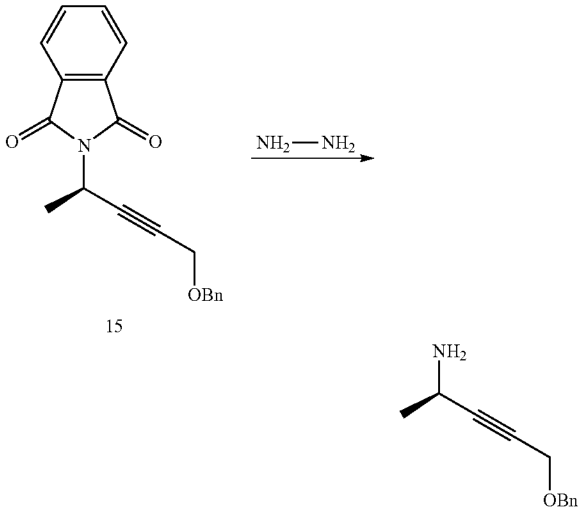

15

16

To a solution of substrate 15 (183 mmol) in the mixture of DCM and methanol (30 mL each) was added hydrazine (5 equiv., 915 mmol, 45 mL) at room temperature and the resulting solution was stirred for 2 hrs, whereupon white ppt. appeared. The precipitate was collected and washed with ethyl acetate and dissolved in DCM and washed repeatedly with brine until no hydrazine was detected. The organic layer was separated, dried with $MgSO_4$ and crude product 15 was taken directly to the next step.

Step C: Preparation of Compound 17

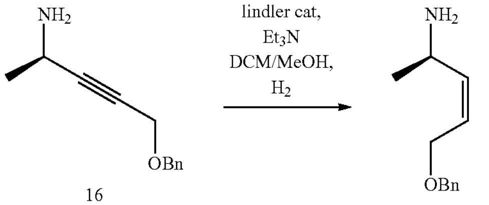

16 17

To a solution of 16 (27 g) in a mixture of DCM and methanol (200 mL each) were added 2.7 mL triethylamine and 2.7 g of Lindlar catalyst, and the resulting solution was stirred under the atmosphere of hydrogen for 3 hrs, whereupon the reaction mixture was filtered and evaporated to dryness and crude product 17 was taken to the next step without any purification.

Step D: Preparation of Compound 19

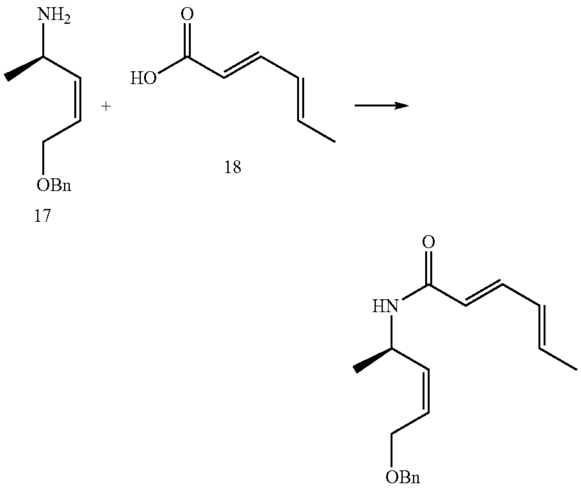

17 18 19

To a solution of amine 17 (13 g, 68 mmol) in 200 mL DMF were added acid 18 (1.02 equiv., 69 mmol), HOBt (1.5 equiv., 102 mmol, 13 g) and DIEA (3 equiv., 204 mmol, 35 mL). The resulting mixture was stirred for 5 minutes and then was added HATU (1.5 equiv., 102 mmol, 38 g). The reaction mixture was stirred for 3 hrs or until the reaction completed. The reaction mixture was diluted with ethyl acetate, washed with saturated $NaHCO_3$, then with brine. The organic layer was separated, dried with $MgSO_4$, evaporated and column chromatographed using 0 to 100% ethyl acetate in hexanes to provide 19.

Step E: Preparation of Compound 20

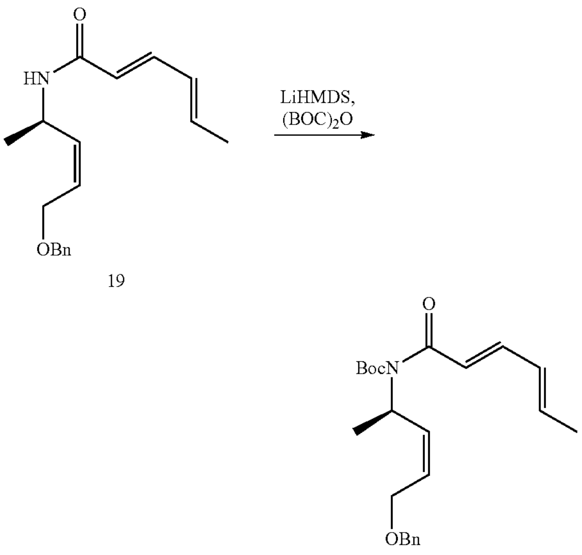

19

20

To solution of amide 19 (14 mg. 49 mmol) and $(Boc)_2O$ (21 g, 98 mmol) in 245 mL THF was added LiHMDS (1.5 equiv., 73.5 mmol) at 0° C. The resulting solution was slowly warmed to room temperature over 30 minutes and stirred for 3 hrs and whereupon the TLC indicated the completion of the reaction. The reaction mixture was quenched with 1N HCl to pH 7 and evaporated to dryness. The resulting slurry was diluted with ethyl acetate, washed with saturated $NaHCO_3$, then with brine. The organic layer was separated, dried with $MgSO_4$, evaporated and column chromatographed using 0 to 100% ethyl acetate in hexanes to provide 20.

Step F: Preparation of Compounds 21 and 22

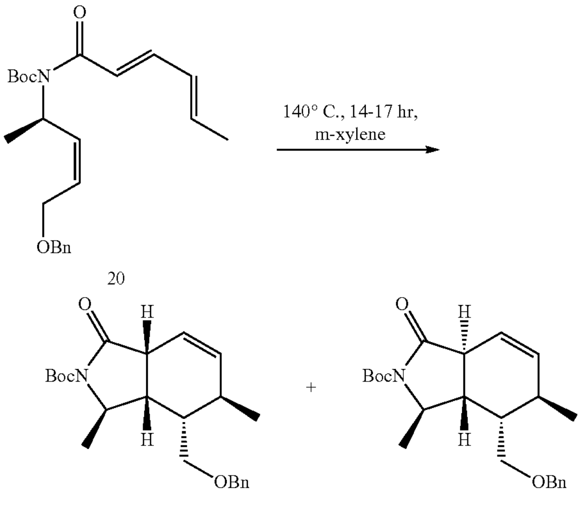

20

21 + 22

A solution of 20 (9 g, 23 mmol) in 575 mL xylene was heated at 150° C. for 6 hrs. Then the reaction mixture was evaporated to dryness and purified using 10% ethyl acetate in hexanes to provide mixture of 21 and 22 as the major product.

Step G: Preparation of Compounds 24 and 25

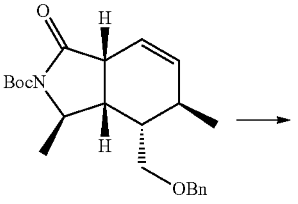

22

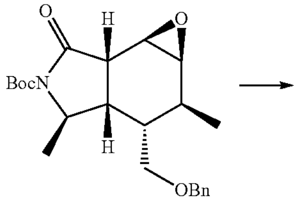

23

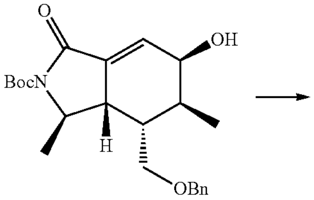

24

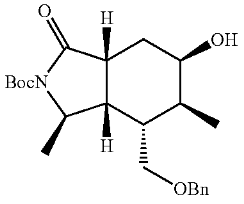

25

Conversion of 22 to 25 was carried out following similar procedures described for Intermediate 1, Steps C to F.

Step H: Preparation of Compound 26

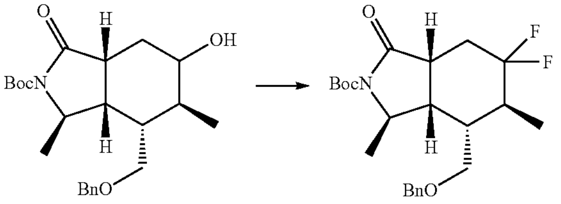

25 26

To a solution of alcohol 25 (135 mg, 0.334 mmol) in 1.5 mL dichloromethane was added Dess Martin periodinane (150 mg, 1.2 equiv., 0.4 mmol) and the resulting mixture was stirred for 1 hr or until the reaction completed. Upon completion of the reaction the crude reaction mixture was evaporated to dryness and purified with 0 to 30% ethyl acetate in hexanes to provide the ketone in 70% yield. NMR ($CDCl_3$) δ 7.2 (m, 5H), 4.5 (d, J=12.5 Hz, 1H), 4.2 (m, 2H), 3.45 (m, 2H), 3.14 (m, 1H), 2.94 (m, 1H), 2.54 (m, 2H), 2.32 (m, 1H), 2.07 (m, 1H), 1.52 (s, 9H), 1.39 (d, J=6.4 Hz, 3H), 1.39 (d, J=7.2 Hz, 3H). To a solution of this ketone (107 mg, 0.266 mmol) in 3 mL dichloromethane was added DAST (0.174 mL, 1.33 mmol, 5 equiv.) at −78° C. and the reaction mixture was slowly warmed to room temperature over night and then was transferred to the sep. funnel, whereupon was added 50 mL of water and was neutralized using saturated $NaHCO_3$ to pH 7.0. The resulting solution was extracted using dichloromethane (3×100 mL), the organic layer was dried over $MgSO_4$, and the solvent was removed under reduced pressure. The crude product was purified using 0 to 100% ethyl acetate in hexanes to provide 26.

Step I: Preparation of Compound 27

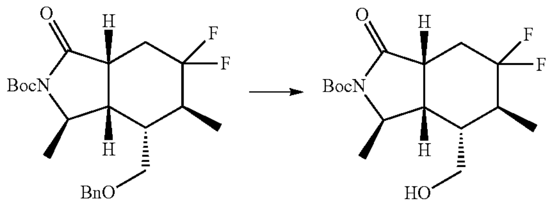

26 27

To the solution of 26 (300 mg, 0.709 mmol) in 4 mL ethyl acetate was added 10% Pd/C (150 mg) and resulting solution was stirred under hydrogen until for 1 hr or until the reaction completed. The reaction mixture was filtered through a pad of CELITE and concentrated to provide the corresponding alcohol 27.

Step J: Preparation of Intermediate 2

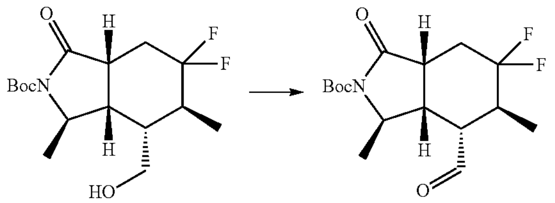

27 Intermediate 2

Compound 27 was used directly to make Intermediate 2 using a similar method described for making Intermediate 1, Step J.

EXAMPLE 1

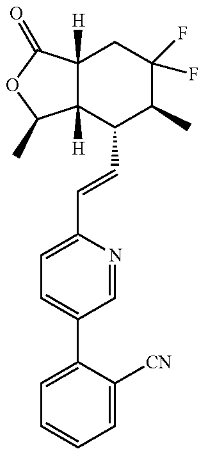 [SMILES: C[C@H]1OC(=O)[C@@H]2CC(F)(F)[C@@H](C)[C@H](/C=C/c3ccc(-c4ccccc4C#N)cn3)[C@H]12]

Step A. Preparation of Compound 1-2

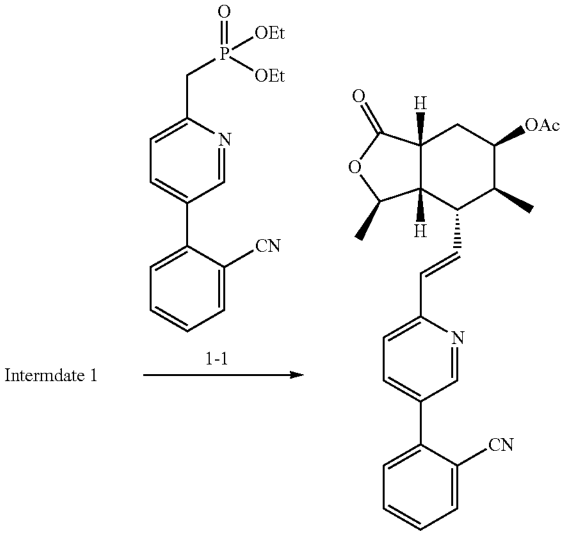

1-1

To a solution of phosphonate 1-1 (11.8 mmol, 3.8 g) in 30 mL THF was added LiHMDS (1 M, 11.8 mL, 11.8 mmol) at 0° C. The reaction mixture was stirred for 20 minutes and $Ti(iOPr)_4$ (3.45 mL, 11.8 mmol) was added and the resulting solution was stirred for 10 minutes before the addition of the solution of the Intermediate 1 (7.87 mmol, 2 g). The resulting mixture was stirred for 2 hrs at 0° C. and then was transferred to the sep. funnel, whereupon was added 50 mL of 20% sodium/potassium tartrate and diluted with 100 mL diethyl ether. The phase was separated and the aqueous layer was extracted three times with diethyl ether (3×100 mL). The organic layer was dried over $MgSO_4$, and the solvent was removed under reduced pressure. The crude product was purified using 0 to 100% ethyl acetate in hexanes to provide 1-2. NMR ($CDCl_3$) δ 8.70 (m, 1H), 7.89 (m, 1H), 7.80 (m, 1H), 7.6 (m, 1H), 7.53 (m, 2H), 7.32 (m, 1H), 6.62 (m, 2H), 5.15 (m, 1H), 4.75 (m, 1H), 2.75 (m, 1H), 2.42 (m, 1H), 2.33 (m, 1H), 2.11 (s, 3H), 1.85 (m, 1H), 1.67 (m, 2H), 1.46 (d, J=6.0 Hz, 3H), 0.94 (d, J=6.4 Hz, 3H).

Step B: Preparation of Compound 1-3

1-3

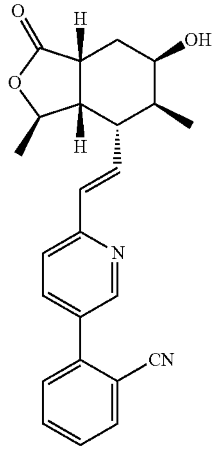

To a solution of acetate 1-2 (4.6 mmol, 2.0 g) in 30 mL dry methanol was added $K_2CO_3$ (6.9 mmol, 0.976 g) at room temperature and the resulting solution was stirred for 2 hrs, then was transferred to the sep. funnel, whereupon was added 50 mL of water and was neutralized using 5N aqueous $H_2SO_4$ to pH 7.0. The resulting solution was extracted using dichloromethane (3×100 mL), the organic layer was dried over $MgSO_4$, and the solvent was removed under reduced pressure. The crude product 1-3 was taken directly to the next step without further purification.

Step C: Preparation of the Compound of Compound 1-4

1-4

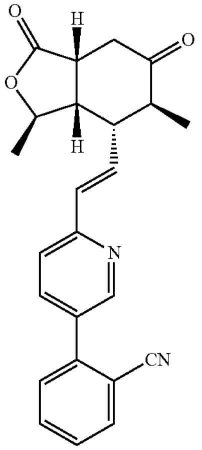

Compound 1-3 was oxidized to the ketone by using Dess Martin periodinane as shown in the method used to convert compound 25 to 26.

Step D. Preparation of Compound of Example 1

To a solution of 1-4 (290 mg, 0.756 mmol) in 7.5 mL dichloromethane was added DAST (3.78 mmol, 0.5 mL) at −78° C. and the reaction mixture was slowly warmed to room temperature over night and then was transferred to the sep. funnel, whereupon was added 50 mL of water and was neutralized using saturated $NaHCO_3$ to pH 7.0. The resulting solution was extracted using dichloromethane (3×100 mL), the organic layer was dried over $MgSO_4$, and the solvent was removed under reduced pressure. The crude product was purified using 0 to 100% ethyl acetate in hexanes to provide Example 1. NMR δ 8.71 (m, 1H), 7.89 (m, 1H), 7.80 (m, 1H), 7.71 (m, 1H), 7.53 (m, 2H), 7.32 (m, 1H), 6.65 (m, 2H), 4.75 (m, 1H), 2.95 (m, 1H), 2.78 (m, 1H), 2.53 (m, 1H), 2.41 (m, 1H), 2.12-1.7 (m, 2H), 1.49 (d, J=5.6 Hz, 3H), 1.10 (d, J=6.4 Hz, 3H).

The compounds in Table 1 were prepared using Intermediate 1 and the chemistry described in Example 1 using the appropriate intermediate.

TABLE 1

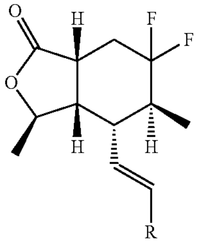

| Example | R | LCMS (M + 1) |
|---|---|---|
| 2 | 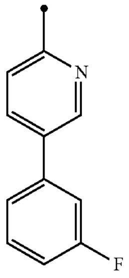 | 402.2 |
| 3 | 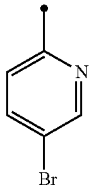 | 387.9 |

The compounds in Table 2 were prepared from product obtained in Example 3 by standard Suzuki coupling reaction with the appropriate boronic acid.

TABLE 2

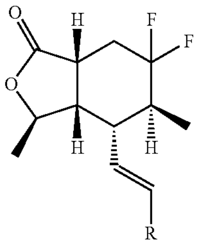

| Example | R | LCMS (M + 1) |
|---|---|---|
| 4 | 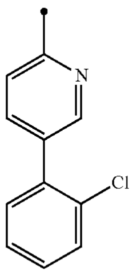 | 418.0 |

TABLE 2-continued

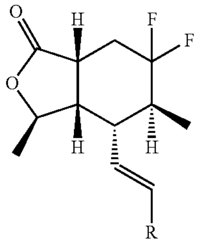

| Example | R | LCMS (M + 1) |
|---|---|---|
| 5 | 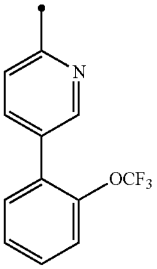 | 468.1 |

EXAMPLE 6

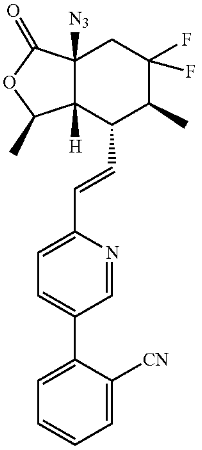 [SMILES: C[C@H]1OC(=O)[C@]2(N=[N+]=[N-])CC(F)(F)[C@@H](C)[C@H](/C=C/c3ccc(-c4ccccc4C#N)cn3)[C@H]12]

To a solution of lactone obtained in Example 1 Step D (0.904 g, 2.2 mmol) in 12 mL THF was added KHMDS (1M, 2.8 mL, 2.8 mmol) at 0° C. The resulting mixture was stirred at 0° C. for 15 minutes before cooling down to −78° C. A cooled solution (cooled at 0° C.) of 2,4,6-triisopropylbenzenesulfonyl azide (1 g, 3.3 mmol) was added and stirred for 3 minutes, then acetic acid was added (0.377 mL, 6.6 mmol). The dry ice bath was replaced with the warm water bath and the reaction mixture was stirred for 1 hr, then was transferred to the sep. funnel, whereupon was added 50 mL of water and was neutralized using saturated $NaHCO_3$ to pH 7.0. The resulting solution was extracted using dichloromethane (3×100 mL), the organic layer was dried over $MgSO_4$, and the solvent was removed under reduced pressure. The crude product was purified using 0 to 100% ethyl acetate in hexanes to provide Example 6.

EXAMPLE 7

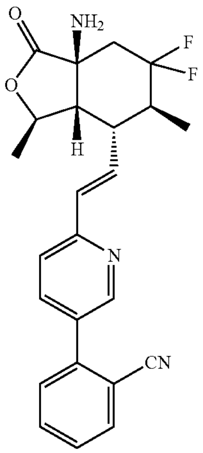 [SMILES: C[C@H]1OC(=O)[C@]2(N)CC(F)(F)[C@@H](C)[C@H](/C=C/c3ccc(-c4ccccc4C#N)cn3)[C@H]12]

To a solution of Example 6 obtained above (600 mg, 1.41 mmol) in the mixture ethyl acetate and water (6.5 mL ethyl acetate and 1 mL water) was added 1M solution of $PMe_3$ (2.1 mmol, 2.1 mL) and the resulting solution was stirred for 2 hrs, then was transferred to the sep. funnel. The resulting solution was extracted using dichloromethane (3×100 mL), the organic layer was dried over $MgSO_4$, and the solvent was removed under reduced pressure. The crude product was purified using 0 to 100% ethyl acetate in hexanes to provide 7. NMR δ 8.71 (m, 1H), 7.89 (m, 1H), 7.80 (m, 1H), 7.71 (m, 1H), 7.53 (m, 2H), 7.32 (m, 1H), 6.65 (m, 2H), 4.63 (m, 1H), 2.88 (m, 1H), 2.2 (m, 2H), 2.21-1.98 (m, 2H), 1.74 (br-s, 2H), 1.81 (d, J=8 Hz, 3H), 1.10 (d, J=10 Hz, 3H). To a solution of Example (500 mg, 1.1 mmol) in 10% acetonitrile in water (2 mL) was added 1.1 mL 1 N aq. HCl and the resulting solution was frozen in dry ice acetone bath and lyophilized to yield the hydrochloride salt of Example 7 as the white solid. m/e 424.2 (M+H).

EXAMPLE 8

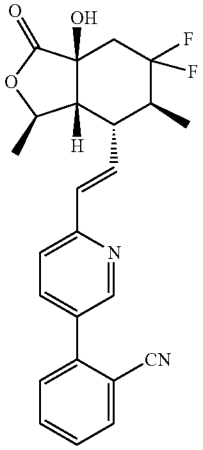 [SMILES: C[C@H]1OC(=O)[C@]2(O)CC(F)(F)[C@@H](C)[C@H](/C=C/c3ccc(-c4ccccc4C#N)cn3)[C@H]12]

To a solution of lactone obtained in Example 1 Step D (180 mg, 0.441 mmol) in 2.2 mL THF was added LiHMDS (1.5 equiv., 0.6 mL, 1M solution in THF) at 0° C. The resulting solution was stirred for 20 minutes at 0° C. before cooling down to −78° C. The argon balloon was replaced by the oxygen balloon and the reaction mixture was degassed and refilled with oxygen (5×). Then the dry ice bath was replaced with ice bath and the reaction mixture was stirred for 2 hrs or until the reaction completed. The reaction mixture was quenched with 20% $Na_2S_2O_3$ (2 mL) and then diluted with water. The resulting solution was extracted using dichloromethane (3×100 mL), the organic layer was dried over $MgSO_4$ and the solvent was removed under reduced pressure. The crude product was purified using 0 to 100% ethyl acetate in hexanes to provide Example 8. m/e 424.2 (M+H).

EXAMPLE 9

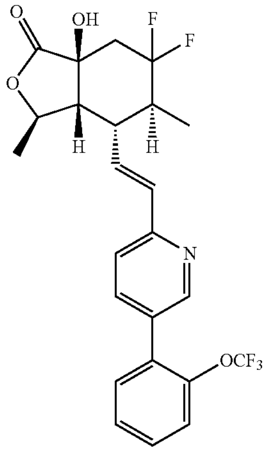 [SMILES: C[C@H]1OC(=O)[C@]2(O)CC(F)(F)[C@@H](C)[C@H](/C=C/c3ccc(-c4ccccc4OC(F)(F)F)cn3)[C@H]12]

To a solution of product obtained in Example 5 (10 mg, 0.02 mmol) in dry, de-oxygenated THF (1000 μL) at 0° C. was added LiHMDS (9.5 mg, 0.06 mmol). The reaction was stirred for 15 minutes before the reaction was warmed to RT and stirred for 1 hour, cooled, washed with saturated sodium bicarbonate solution, dried over $MgSO_4$, filtered and concentrated to yield Example 9. MPLC purification (0-40% EtOAc/Hex) gave rise to the desired product. LC/MS: m/e 484.1 $(M+H)^+$

EXAMPLE 10

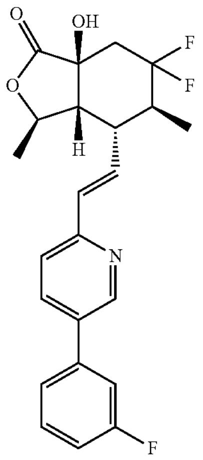 [SMILES: C[C@H]1OC(=O)[C@]2(O)CC(F)(F)[C@@H](C)[C@H](/C=C/c3ccc(-c4cccc(F)c4)cn3)[C@H]12]

Compound 37 was prepared from the product obtained in Example 2 following a similar protocol that was used to make the product obtained in Example 9. LC/MS: m/e 418.2 (M+H).

EXAMPLE 11

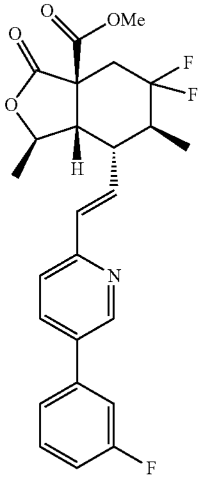 [SMILES: COC(=O)[C@@]12CC(F)(F)[C@@H](C)[C@H](/C=C/c3ccc(-c4cccc(F)c4)cn3)[C@@H]1[C@@H](C)OC2=O]

To a solution of product obtained in Example 2 (400 mg, 1 mmol) in 5 mL THF was added LiHMDS (1.5 equiv., 1.5 mL) at 0° C. and the resulting solution was stirred at this temperature for 30 min, then it was cooled to −78° C. To this reaction mixture was added methyl cyanoformate (1.5 equiv., 0.127 mL) and stirred for 40 minutes, then slowly warmed to room temperature and stirred for 15 minutes. At this time aq. ammonium ferrous sulfate was added, then diluted with water and extracted with ethyl acetate, the organic layer was dried over $MgSO_4$ and the solvent was removed under reduced pressure. The crude product was purified using 0 to 100% ethyl acetate in hexanes to provide Example 11.

EXAMPLE 12

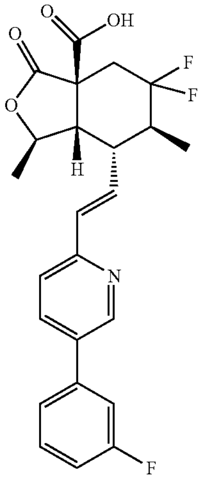 [SMILES: C[C@H]1OC(=O)[C@]2(C(=O)O)CC(F)(F)[C@@H](C)[C@H](/C=C/c3ccc(-c4cccc(F)c4)cn3)[C@H]12]

To a solution of Example 11 (250 mg, 0.455 mmol) in 1.5 mL DCM was added $BBr_3$ at 0° C. and the reaction mixture was slowly warmed to room temperature and stirred for additional 30 minutes, diluted with ethyl acetate, washed with water, the organic layer was separated, dried over $MgSO_4$ and the solvent was removed under reduced pressure. The crude product was purified using 0 to 100% ethyl acetate in hexanes to provide Example 12.

EXAMPLE 13

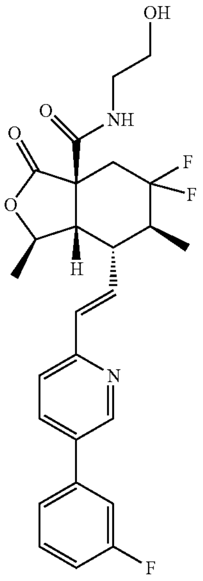 [SMILES: C[C@H]1OC(=O)[C@]2(C(=O)NCCO)CC(F)(F)[C@@H](C)[C@H](/C=C/c3ccc(-c4cccc(F)c4)cn3)[C@H]12]

To a solution of Example 12 in 2 mL DMF were added ethanol amine (1.5 equiv., 0.682 mmol), DIEA (5 equiv., 0.680 mmol) and HATU (1.5 equiv., 0.680 mmol, 250 mg) and the resulting solution was stirred at room temperature until the reaction completed. Then, the reaction mixture was diluted with water and extracted with ethyl acetate, the organic layer was dried over $MgSO_4$ and the solvent was removed under reduced pressure. The crude product was purified using 0 to 100% ethyl acetate in hexanes to provide Example 13. LC/MS: m/e 511.2 (M+Na).

EXAMPLE 14

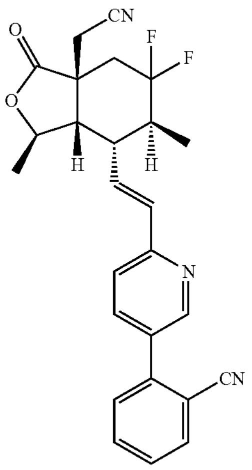 [SMILES: C[C@H]1OC(=O)[C@]2(CC#N)CC(F)(F)[C@@H](C)[C@H](/C=C/c3ccc(-c4ccccc4C#N)cn3)[C@H]12]

To a solution of product obtained in Example 1 (75 mg, 0.184 mmol) in dry, de-oxygenated THF (1020 μL) at 0° C. was added KHMDS (551 μL, 0.275 mmol). The reaction was stirred for 15 minutes and then cooled to −78° C. Bromoacetonitrile (22 mg, 0.18 mmol) was then added and the reaction warmed to 40° C. and stirred for 1 hour, cooled, washed with saturated sodium bicarbonate solution, dried over $MgSO_4$, filtered and concentrated. MPLC purification (5-35% EtOAc/Hex) gave rise to the desired product Example 14. LC/MS: m/e 448.1 $(M+H)^+$.

EXAMPLE 15

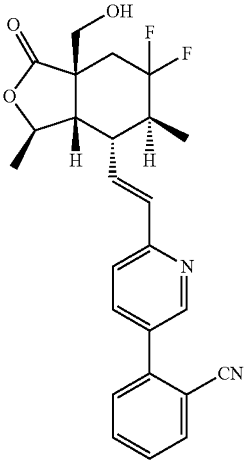 [SMILES: C[C@H]1OC(=O)[C@]2(CO)CC(F)(F)[C@@H](C)[C@H](/C=C/c3ccc(-c4ccccc4C#N)cn3)[C@H]12]

To a solution of product obtained in Example 1 (75 mg, 0.184 mmol) in dry, de-oxygenated THF (1020 μL) at 0° C. was added KHMDS (551 μL, 0.275 mmol). The reaction was stirred for 15 minutes and then cooled to −78° C. At which point, a precooled; de-gassed suspension of paraformaldehyde (5.51 mg, 0.184 mmol) in THF (1020 μL) was added via syringe and stirred for 5 minutes. The reaction warmed to 40° C. and stirred for 1 h, washed with saturated sodium bicarbonate solution, dried over $MgSO_4$, filtered and concentrated. MPLC purification (25-75% EtOAc/Hex) gave rise to the desired product. LC/MS: m/e 439.1 $(M+H)^+$.

EXAMPLE 16

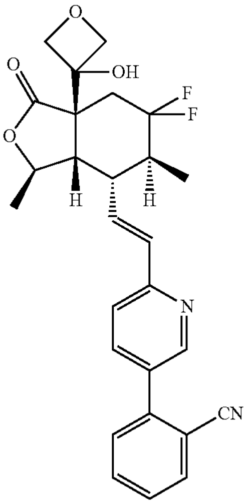 [SMILES: C[C@H]1OC(=O)[C@]2(C3(O)COC3)CC(F)(F)[C@@H](C)[C@H](/C=C/c3ccc(-c4ccccc4C#N)cn3)[C@H]12]

To a solution of product obtained in Example 1 (75 mg, 0.184 mmol) in dry, de-oxygenated THF (1020 μL) at 0° C. was added KHMDS (551 μL, 0.275 mmol). The reaction was stirred for 15 minutes and then cooled to −78 C. At which point, a precooled; de-gassed suspension of oxetan-3-one (5.51 mg, 0.184 mmol) in THF (1020 μL) was added via syringe and stirred for 5 minutes. The solution was quenched with AcOH and allowed to warm to 40° C. The solution was stirred for 1 h, washed with saturated sodium bicarbonate solution, dried over $MgSO_4$, filtered and concentrated. MPLC purification (25-75% EtOAc/hex) gave rise to the desired product, Example 16. LC/MS: m/e 481.2 $(M+H)^+$.

The compounds in Table 3 were all prepared using the chemistry described in Example 16.

TABLE 3

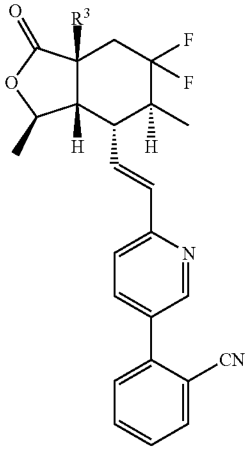

| Example | $R^3$ | LCMS (M + 1) |
|---|---|---|
| 17 | 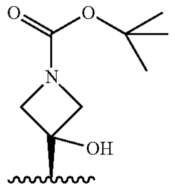 | 508.3 |
| 18 | 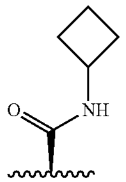 | 506.2 |
| 19 | 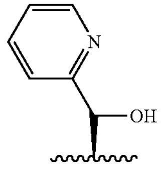 | 516.2 |
| 20a | 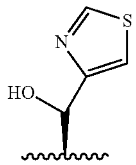 | 522.2 |

TABLE 3-continued
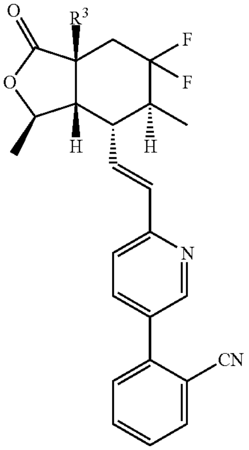
| Example | $R^3$ | LCMS (M + 1) |
|---|---|---|
| 20b | 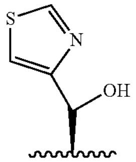 | 522.2 |
| 21a | 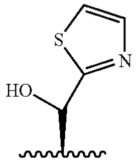 | 522.2 |
| 21b | 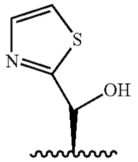 | 522.2 |
| 22a | 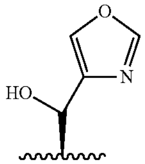 | 506.3 |
| 22b | 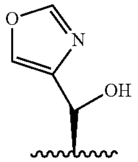 | 506.3 |
| 23a | 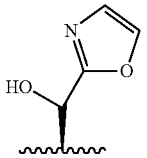 | 506.3 |
TABLE 3-continued
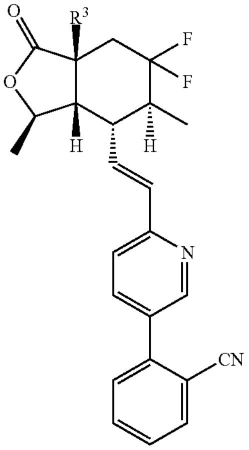
| Example | $R^3$ | LCMS (M + 1) |
|---|---|---|
| 23b | 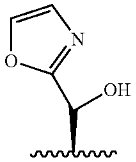 | 506.3 |
EXAMPLE 24
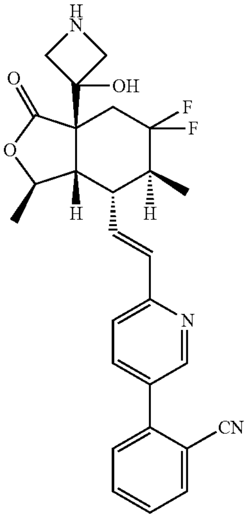 [SMILES: C[C@H]1OC(=O)[C@]2(C3(O)CNC3)CC(F)(F)[C@@H](C)[C@H](/C=C/c3ccc(-c4ccccc4C#N)cn3)[C@H]12]
The product obtained in Example 17 was dissolved in 1.0 mL of 4N HCl in dioxane. The resulting suspension was concentrated to dryness giving rise to the titled compound, Example 24. LC/MS: m/e 480.2 $(M+H)^+$.

EXAMPLE 25

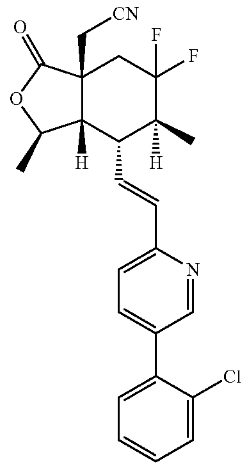 [SMILES: C[C@H]1OC(=O)[C@]2(CC#N)CC(F)(F)[C@@H](C)[C@H](/C=C/c3ccc(-c4ccccc4Cl)cn3)[C@H]12]

The compound of Example 25 was prepared using a method described in Example 14 and using product obtained in Example 4 and appropriate reagents. LC/MS: m/e 457.1 $(M+H)^+$.

EXAMPLE 26

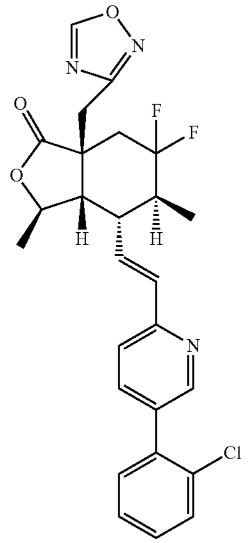 [SMILES: C[C@H]1OC(=O)[C@]2(Cc3ncon3)CC(F)(F)[C@@H](C)[C@H](/C=C/c3ccc(-c4ccccc4Cl)cn3)[C@H]12]

A solution of product obtained in Example 4 (100 mg, 0.219 mmol) in EtOH (1094 μL) was added 0.25 mL of aqueous hydroxylamine (145 mg, 2.2 mmol). The solution heated to 80° C. for 1 h. The reaction was then concentrated and redissolved in triethyl orthoformate (364 μL, 2.189 mmol) and EtOH (1094 μL) with catalytic TFA (2.53 μl, 0.033 mmol). The reaction was heated for an additional hour at 80° C. The reaction was concentrated and purified via MPLC (10-40% EtOAc/Hexane). LC/MS: m/e 457.1 $(M+H)^+$.

EXAMPLE 27

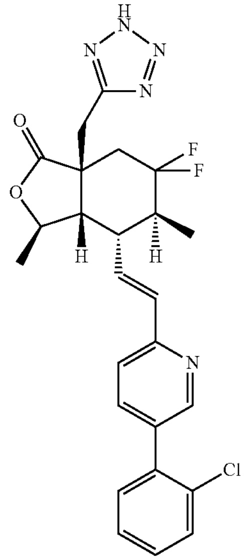 [SMILES: C[C@H]1OC(=O)[C@]2(Cc3nn[nH]n3)CC(F)(F)[C@@H](C)[C@H](/C=C/c3ccc(-c4ccccc4Cl)cn3)[C@H]12]

A solution of product obtained in Example 4 (125 mg, 0.27 mmol) in 2:1 water/IPA (900/450 μL) was added sodium azide (36 mg, 0.5 mmol) and zinc bromide (31 mg, 0.14 mmol). The solution heated to 80° C. for 36 h. The reaction was quenched with 1N HCl and partitioned between EtOAc/water. The organic layer was removed, dried over $MgSO_4$, filtered, concentrated and purified via MPLC (20-60% ETOAc/hexane). LC/MS: m/e 500.1 $(M+H)^+$.

EXAMPLE 28

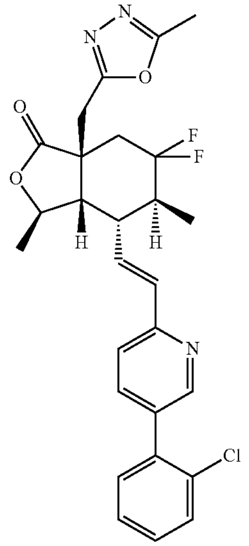 [SMILES: Cc1nnc(C[C@@]23CC(F)(F)[C@@H](C)[C@H](/C=C/c4ccc(-c5ccccc5Cl)cn4)[C@@H]2[C@@H](C)OC3=O)o1]

A solution of product obtained in Example 27 (12 mg, 0.02 mmol) dissolved in acetic anhydride (96 μL) was heated at reflux in a sealed tube. The solution was then cooled to RT, diluted with 3 mL of saturated sodium bicarbonate solution and 5 mL of EtOAc, the biphasic mixture was passed through a solid phase extraction (SPE) column and washed with EtOAc. The collected organic layer was concentrated and purified via MPLC (0-50% EtOAc/hex) to give desired product. LC/MS: m/e 514.2 $(M+H)^+$.

EXAMPLE 29a AND 29b

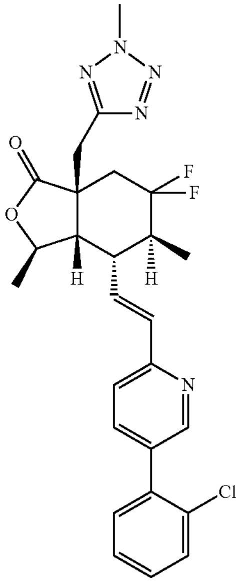

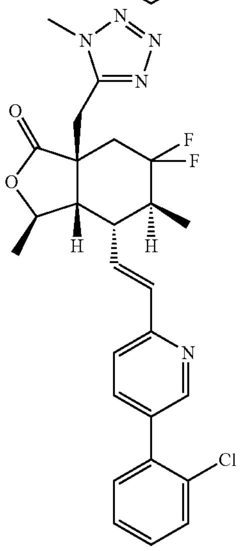

A solution of product obtained in Example 27 (21 mg, 0.04 mmol) dissolved in DMF (140 μL) was treated with $K_2CO_3$ (6 mg, 0.04 mmol) and MeI (6 mg, 0.04 mmol). After 2 h at rt, the solution was diluted with 3 mL of saturated sodium bicarbonate solution and 5 mL of EtOAc, the biphasic mixture was passed through a solid phase extraction (SPE) column and washed with EtOAc. The collected organic layer was concentrated and purified via MPLC (0-40% EtOAc/hex) to give desired products. LC/MS: m/e 514.2 $(M+H)^+$.

EXAMPLE 30

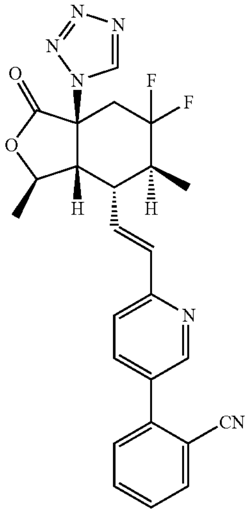 [SMILES: C[C@H]1OC(=O)[C@]2(n3cnnn3)CC(F)(F)[C@@H](C)[C@H](/C=C/c3ccc(-c4ccccc4C#N)cn3)[C@H]12]

A solution of product obtained in Example 7 (31 mg, 0.07 mmol) dissolved in triethyl orthoformate (5 mL) and sodium azide (5 mg, 0.07 mmol) was heated in a sealed tube to 80° C. for 2 h. The solution was cooled then concentrated and purified via MPLC. LC/MS: m/e 477.1 $(M+H)^+$.

EXAMPLE 31

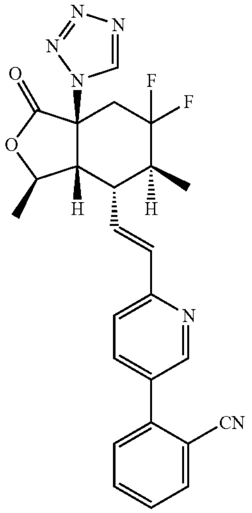 [SMILES: C[C@H]1OC(=O)[C@]2(n3cnnn3)CC(F)(F)[C@@H](C)[C@H](/C=C/c3ccc(-c4ccccc4C#N)cn3)[C@H]12]

A solution of product obtained in Example 6 (31 mg, 0.07 mmol), TMS acetylene (94 μL, 0.07 mmol), $K_2CO_3$ (46 mg, 0.33 mmol), $CuSO_4$ (3 mg, 0.01 mmol), and sodium ascorbate (5 mg, 0.03 mmol) in 1:1 v:v $MeOH:H_2O$ (800 μL) was placed in a sealed tube and stirred at rt for 24 h. The resulting suspension was partitioned between DCM and 10% $NH_4OH$. The organic layer was dried over $MgSO_4$, filtered and concentrated. The oil was purified via MPLC. LC/MS: m/e 476.2 $(M+H)^+$.

The compounds in Table 4 were all prepared using the chemistry described in Example 16.

TABLE 4

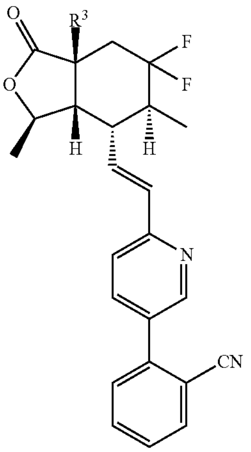

| Example | $R^3$ | LCMS (M + 1) |
|---|---|---|
| 32 | 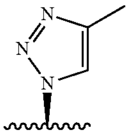 | 490.2 |
| 33 | 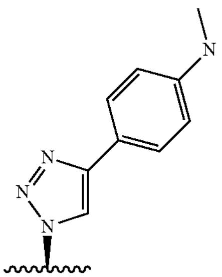 | 595.3 |
| 34 | 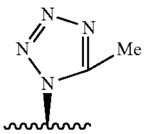 | 491.2 |

EXAMPLE 35

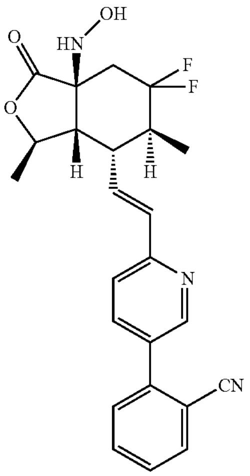 [SMILES: C[C@H]1OC(=O)[C@]2(NO)CC(F)(F)[C@@H](C)[C@H](/C=C/c3ccc(-c4ccccc4C#N)cn3)[C@H]12]

Step A:

To a solution of Example 8 was added MsCl (18 mg, 0.16 mmol) followed by TEA (53 mg, 0.4 mmol) at 0° C. The solution was stirred for 10 minutes, quenched with 3 mL of water and passed through a SPE which was washed with chloroform. The mesylate was concentrated and used in next step.

Step B:

To a solution of mesylate prepared as described in Step A (25 mg, 0.05 mmol) was added imidazole (4 mg, 0.05 mmol) followed by $Cs_2CO_3$ (16 mg, 0.05 mmol) at RT in DMSO (0.5 mL). Upon completion of the reaction, the solution was cooled and partitioned between $DCM/H_2O$. The organic layer was removed, dried, filtered and concentrated giving rise to an oil which was purified by MPLC (25-80% EtOAc/hexanes). LC/MS: m/e 475.2 $(M+H)^+$.

EXAMPLE 36

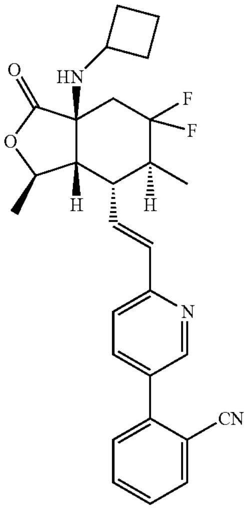 [SMILES: C[C@H]1OC(=O)[C@]2(NC3CCC3)CC(F)(F)[C@@H](C)[C@H](/C=C/c3ccc(-c4ccccc4C#N)cn3)[C@H]12]

To a solution of product obtained in Example 7 (20 mg, 0.05 mmol) was added cyclobutanone (7 mg, 0.10 mmol)

followed by $NaCNBH_3$ (5 mg, 0.07 mmol) and AcOH (8.5 mg, 0.14 mmol) at RT in MeOH (0.5 mL). Upon completion of the reaction as judged by TLC and LC/MS, the solution was quenched with 5% aq. $K_2CO_3$ and partitioned between EtOAc/$H_2O$. The organic layer was removed, dried, filtered and concentrated giving rise to an oil which was purified by MPLC (50% EtOAc/hexanes). LC/MS: m/e 478.2 $(M+H)^+$.

The compounds in Table 5 were prepared using the procedure described for Example 36.

TABLE 5

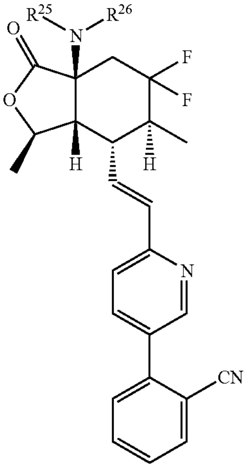

| Example | $R^{25}$ | $R^{26}$ | LCMS (M + 1) |
|---|---|---|---|
| 37 | Me | Me | 452.1 |
| 38 | H | 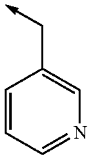 | 515.2 |
| 39 | H | 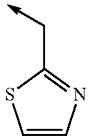 | 521.2 |
| 40 | H | 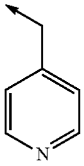 | 515.2 |
| 41 | H | 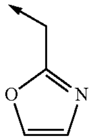 | 505.3 |
| 42 | H | 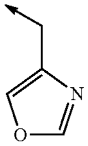 | 505.3 |

TABLE 5-continued

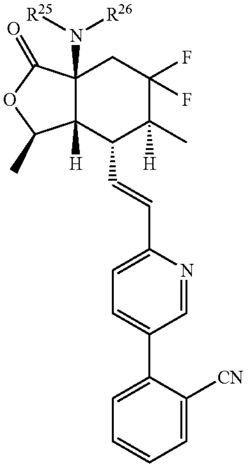

| Example | $R^{25}$ | $R^{26}$ | LCMS (M + 1) |
|---|---|---|---|
| 43 | H | 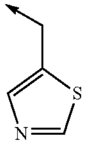 | 521.2 |
| 44 | H | 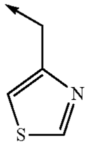 | 521.2 |
| 45 | H | 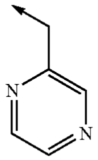 | 516.2 |
| 46 | H | 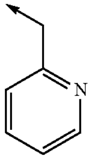 | 515.2 |
| 47 | H | 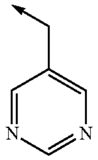 | 516.2 |
| 48 | H | 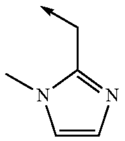 | 518.3 |
| 49 | H | 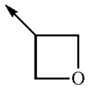 | 480.2 |

TABLE 5-continued

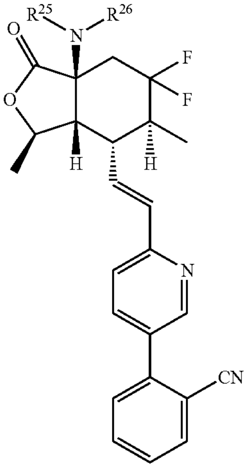

| Example | $R^{25}$ | $R^{26}$ | LCMS (M + 1) |
|---|---|---|---|
| 50 | H | 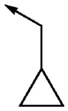 | 478.1 |
| 51 | H | 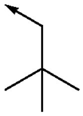 | 494.2 |

EXAMPLE 52

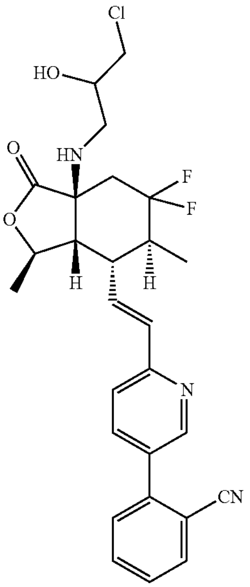 [SMILES: C[C@H]1OC(=O)[C@]2(NCC(O)CCl)CC(F)(F)[C@@H](C)[C@H](/C=C/c3ccc(-c4ccccc4C#N)cn3)[C@H]12]

To a solution of product obtained in Example 7 (40 mg, 0.09 mmol) was added epichlorohydrin (9 mg, 0.10 mmol) RT in MeOH (0.5 mL). Upon completion of the reaction as judged by TLC and LC/MS, the solution was concentrated giving rise to an oil which was purified by MPLC (0-100% EtOAc/hexanes). LC/MS: m/e 516.2 $(M+H)^+$

EXAMPLE 53

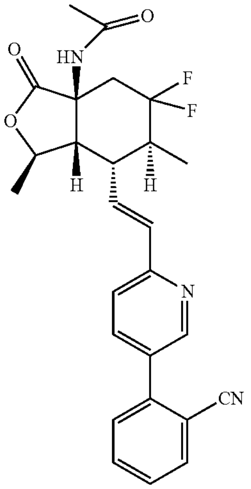 [SMILES: CC(=O)N[C@@]12CC(F)(F)[C@@H](C)[C@H](/C=C/c3ccc(-c4ccccc4C#N)cn3)[C@@H]1[C@@H](C)OC2=O]

To product obtained in Example 7 (20 mg, 0.05 mmol) in DCM at 0° C. was added acetyl chloride (4 mg, 0.05 mmol) and TEA (10 mg, 0.10 mmol). The resulting solution was stirred at 0° C. for 1 h, diluted with $H_2O$, extracted with DCM, washed with brine, dried over $MgSO_4$, filtered, concentrated and purified by flash chromatography (30-80% EtOAc/hexanes). LC/MS: m/e 466.2 $(M+H)^+$.

EXAMPLE 54

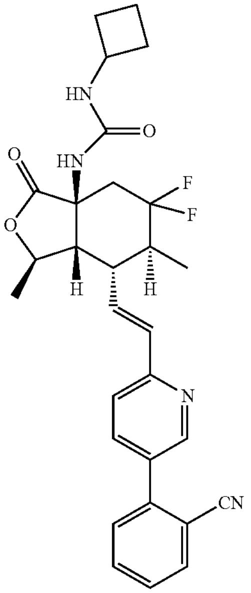 [SMILES: C[C@H]1OC(=O)[C@]2(NC(=O)NC3CCC3)CC(F)(F)[C@@H](C)[C@H](/C=C/c3ccc(-c4ccccc4C#N)cn3)[C@H]12]

To a solution of product obtained in Example 7 (28 mg, 0.07 mmol) in DCM (600 μL) at RT was added cyclobutyl isocyanate (7 mg, 0.07 mmol) followed by Hunig's base (13 mg, 0.10 mmol). The solution was stirred for 1 h, washed with saturated sodium bicarbonate solution, dried over $MgSO_4$, filtered and concentrated. MPLC purification (25-75% EtOAc/hex) gave rise to the desired product. LC/MS: m/e 521.2 $(M+H)^+$.

The compounds in Table 2 were prepared using the method described for Example 54 and the appropriate isocyanate, thioisocyanate or acid chloride.
TABLE 6
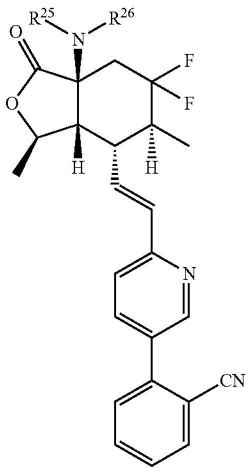
| Example | $R^{25}$ | $R^{26}$ | LCMS (M + 1) |
|---|---|---|---|
| 55 | H | 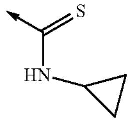 | 523.6 |
| 56 | H | 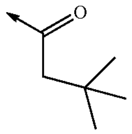 | 524.4 |
| 57 | H | 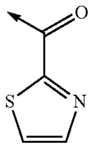 | 535.3 |
| 58 | H | 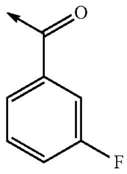 | 546.3 |
| 59 | H | 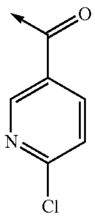 | 563.3 |
TABLE 6-continued
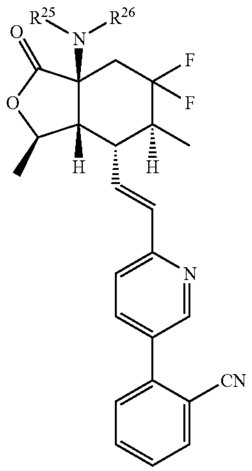
| Example | $R^{25}$ | $R^{26}$ | LCMS (M + 1) |
|---|---|---|---|
| 60 | H | 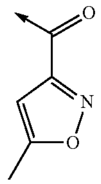 | 533.3 |
| 61 | H | 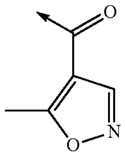 | 533.3 |
| 62 | H | 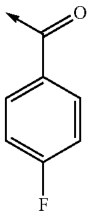 | 546.3 |
| 63 | H | 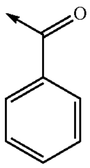 | 528.3 |
| 64 | H | 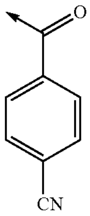 | 553.3 |

TABLE 6-continued

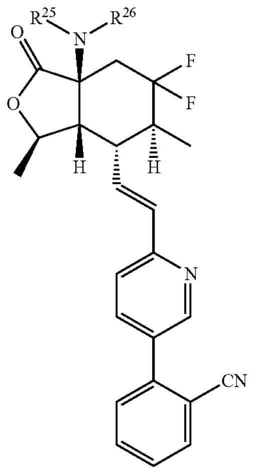

| Example | $R^{25}$ | $R^{26}$ | LCMS (M + 1) |
| --- | --- | --- | --- |
| 66 | H | 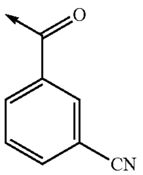 | 553.3 |
| 66 | H | 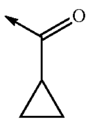 | 492.3 |
| 67 | H | 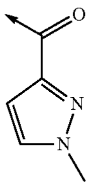 | 532.3 |

EXAMPLE 68

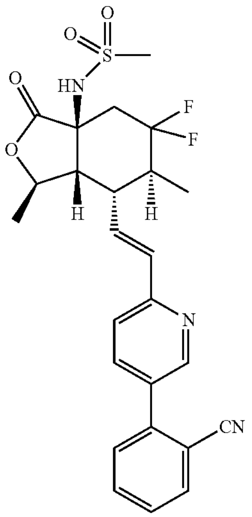 [SMILES: C[C@H]1OC(=O)[C@]2(NS(C)(=O)=O)CC(F)(F)[C@@H](C)[C@H](/C=C/c3ccc(-c4ccccc4C#N)cn3)[C@H]12]

To a solution of product obtained in Example 7 (22 mg, 0.05 mmol) in DCM (600 µl) at rt was added MsCl (7 mg, 0.06 mmol) followed by TEA (11 mg, 0.10 mmol). The solution was stirred for 1 h, washed with saturated sodium bicarbonate solution, dried over $MgSO_4$, filtered and concentrated. MPLC purification (0-30% EtOAc/hex) gave rise to the desired product. LC/MS: m/e 502.2 $(M+H)^+$.

EXAMPLE 69

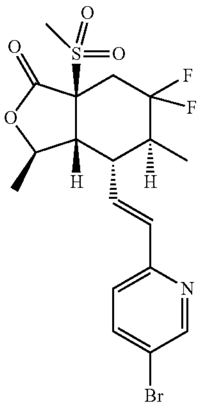 [SMILES: C[C@H]1OC(=O)[C@]2(S(C)(=O)=O)CC(F)(F)[C@@H](C)[C@H](/C=C/c3ccc(Br)cn3)[C@H]12]

To a solution of product obtained in Example 3 (50 mg, 0.13 mmol) in dry, de-oxygenated THF (1020 µL) at 0° C. was added LiHMDS (1.0 M in THF, 200 µl, 0.2 mmol). The reaction was stirred for 15 minutes before methanesulfonyl chloride (30 mg, 0.26 mmol) was then added and the reaction warmed to RT and stirred for 1 hour, cooled, washed with saturated sodium bicarbonate solution, dried over $MgSO_4$, filtered and concentrated. MPLC purification (0-35% EtOAc/hex) gave rise to the desired product. LC/MS: m/e 461.9 $(M+H)^+$.

EXAMPLE 70

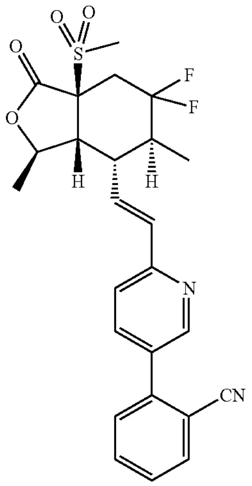 [SMILES: C[C@H]1OC(=O)[C@]2(S(C)(=O)=O)CC(F)(F)[C@@H](C)[C@H](/C=C/c3ccc(-c4ccccc4C#N)cn3)[C@H]12]

To a solution of Example 68 (12 mg, 0.02 mmol) in toluene/EtOH/$H_2O$ (5 mL:1 mL:1.5 mL) was added $Pd(PPh_3)_4$ (6 mg, 0.005 mmol) and 2-(5,5-dimethyl-1,3,2-dioxaborinan-2-yl)benzonitrile (8 mg, 0.04 mmol). The reaction was heated to reflux for 2 h. After which point the solution was cooled, washed with saturated sodium bicarbonate solution, dried over $MgSO_4$, filtered and concentrated. MPLC purification (0-60% EtOAc/Hex) gave rise to the desired product. LC/MS: m/e 487.1 $(M+H)^+$.

EXAMPLE 71

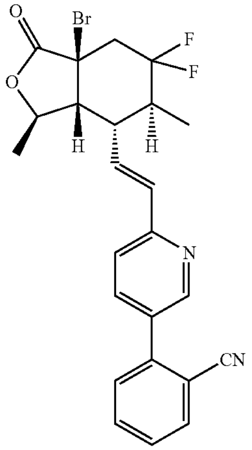 [SMILES: C[C@H]1OC(=O)[C@]2(Br)CC(F)(F)[C@@H](C)[C@H](/C=C/c3ccc(-c4ccccc4C#N)cn3)[C@H]12]

To a solution of product obtained in Example 1 (100 mg, 0.24 mmol) in dry, de-oxygenated THF (1020 μL) at 0° C. was added LiHMDS (1.0 M in THF, 367 μL, 0.4 mmol). The reaction was stirred for 15 minutes before cyanogen bromide (52 mg, 0.5 mmol) was then added and the reaction warmed to rt and stirred for 1 hour, cooled, washed with saturated sodium bicarbonate solution, dried over $MgSO_4$, filtered and concentrated. MPLC purification (0-30% EtOAc/Hex) gave rise to the desired product. LC/MS: m/e 489.1 $(M+H)^+$.

EXAMPLE 72

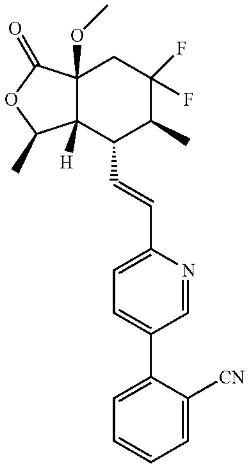 [SMILES: CO[C@@]12CC(F)(F)[C@@H](C)[C@H](/C=C/c3ccc(-c4ccccc4C#N)cn3)[C@@H]1[C@@H](C)OC2=O]

To a solution of product obtained in Example 8 (20 mg, 0.05 mmol) in dry, de-oxygenated THF (2000 μL) at 0° C. was added LiHMDS (9.5 mg, 0.06 mmol). The reaction was stirred for 15 minutes before MeI (14 mg, 0.9 mmol) was then added and the reaction warmed to RT and stirred for 1 hour, cooled, washed with saturated sodium bicarbonate solution, dried over $MgSO_4$, filtered and concentrated. MPLC purification (7-60% EtOAc/Hex) gave rise to the desired product. LC/MS: m/e 439.1 $(M+H)^+$.

EXAMPLE 73

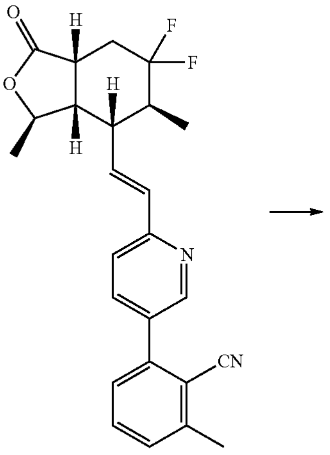

Example 1

-continued

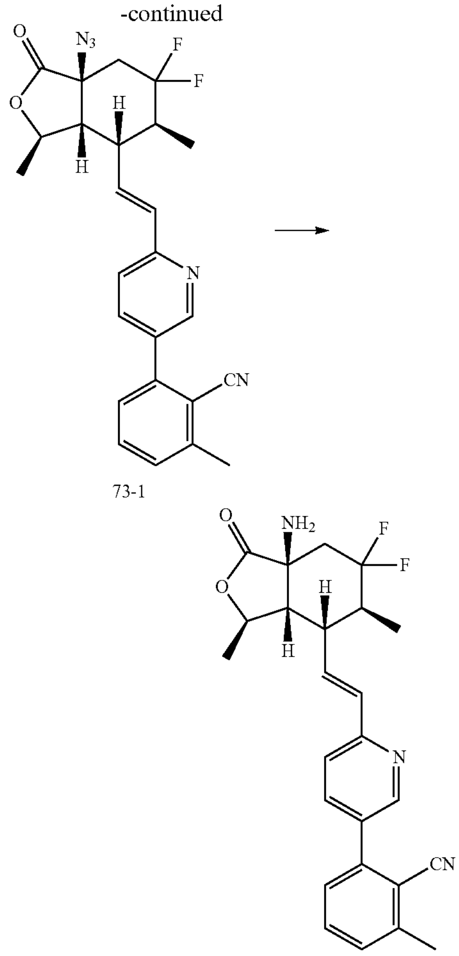

73-1

Example 73

Step A: Preparation of Compound 73-1

To a solution 73-1 prepared as shown in Example 1 (0.0429 g, 0.102 mmol) in dry THF (1.0 mL) was added a 0.5 M solution of potassium hexamethyldisilazide in toluene (0.264 ml, 0.132 mmol) at 0° C. After 10 min., the dark brown reaction mixture was cooled to −78° C. and a cooled solution of 2,4,6-triisopropylbenzenesulfonyl azide (0.0463 g, 0.150 mmol) in dry THF (0.5 mL) was added dropwise. The resulting orange solution was allowed to stir for 2 minutes then quenched by addition of acetic acid (0.017 ml, 0.305 mmol). The reaction mixture became a yellow solution. The reaction mixture was warmed to room temperature by removing the dry ice bath and submerging the reaction flask in an ambient temperature water bath. The reaction was stirred at room temperature for 30 min. The reaction was concentrated in vacuo and the residue was partitioned between EtOAc and sat. aqueous $NaHCO_3$. The organic layer was washed with brine, dried over $MgSO_4$, and concentrated in vacuo to give a yellow oil. The crude product was purified by silica gel chromatography on an Isco CombiFlash® Rf system (12 g silica gel, 30 mL/min, 254 nM, gradient elution 0% to 50% EtOAc/hexane). The fractions containing the desired product (eluted at ~38% EtOAc/hexane) were collected and concentrated in vacuo to afford 73-1 as a pale yellow foam.

Step B: Preparation of Example 73

To a solution of 73-1 obtained in Step A above (35.1 mg, 0.076 mmol) in an ethyl acetate (0.5 ml)/water (0.050 ml) mixture was added a 1M solution of trimethylphosphine in THF (0.114 ml, 0.114 mmol) at room temperature. The reaction was stirred for 2.5 hours then concentrated in vacuo. The residue was purified by silica gel chromatography on an Isco CombiFlash® system (4 g silica gel, 18 mL/min, 254 nM, 0% to 100% EtOAc/hexane). The fractions containing the desired product (eluted at ~70% EtOAc/hexane) were concentrated in vacuo to a colorless foam which was lyophilized from acetonitrile/water over the weekend afforded Example 73 as a white solid. LC/MS: m/e 438.2 $(M+H)^+$

EXAMPLE 74

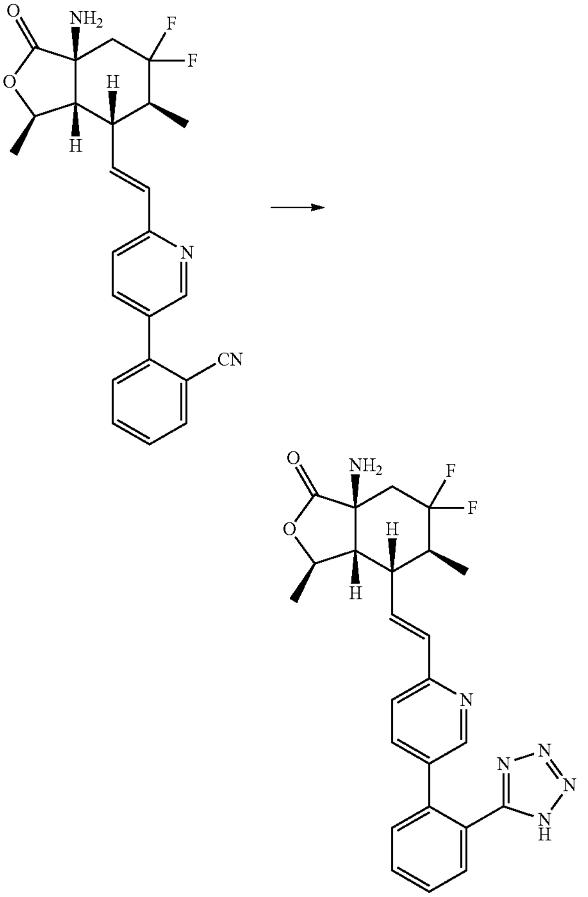

Example 74

The product obtained in Example 8 (0.0333 g, 0.079 mmol), trimethylsilyl azide (0.104 mL, 0.786 mmol), and dibutyltin oxide (6.1 mg, 0.025 mmol) were combined in a microwave vial, sealed, and heated in a microwave at 150° C. for 1 hour. LC/MS analysis showed incomplete reaction so the reaction mixture was heated conventionally at 115° C. overnight. After 16 hours at 150° C., the reaction was concentrated in vacuo and the residue was purified by HPLC (30×100 mm Waters SunFire™ column; 5 micron; 35 mL/min.; 210 nM; 0% to 50% $CH_3CN$+0.05% TFA/water+0.05% TFA over 15 minutes). The fractions containing the title compound (eluted at ~27% $CH_3CN$+0.05% TFA/water+0.05% TFA), were combined and lyophilized overnight to afford the compound of Example 74 as a white solid. LC/MS: m/e 467.0 $(M+H)^+$

EXAMPLE 75

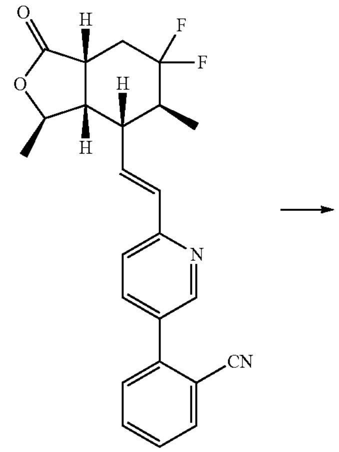

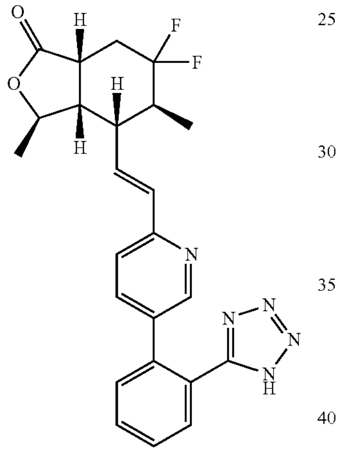

Example 75

The product obtained in Example 1 (0.018 g, 0.044 mmol), trimethylsilyl azide (0.012 mL, 0.088 mmol), and dibutyltin oxide (2.6 mg, 0.010 mmol) were combined in a microwave vial, sealed, and heated in a microwave at 150° C. for 30 minutes. LC/MS analysis showed incomplete reaction so additional trimethylsilyl azide (0.012 mL, 0.088 mmol) was added and the reaction mixture was heated in a microwave at 150° C. for 1 hour. Although reaction was still incomplete by TLC, the reaction mixture was concentrated in vacuo and the residue was purified by HPLC (30×100 mm Waters SunFire™ column; 5 micron; 35 mL/min.; 210 nM; 10% to 60% CH3CN+0.05% TFA/water+0.05% TFA over 14 minutes). The fractions containing the title compound (eluted at ~53% $CH_3CN$+0.05% TFA/water+0.05% TFA), were combined and lyophilized overnight to afford the compound of Example 75 as a white solid. LC/MS: m/e 452.7 $(M+H)^+$.

EXAMPLE 76

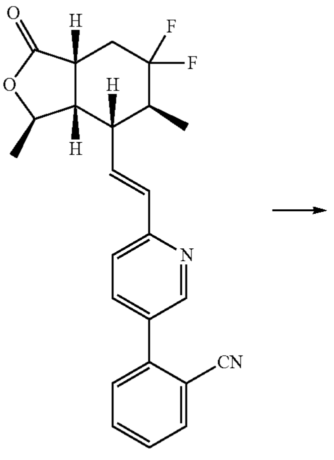

Example 1

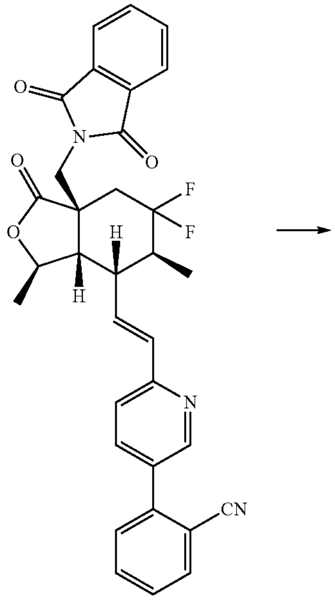

76-1

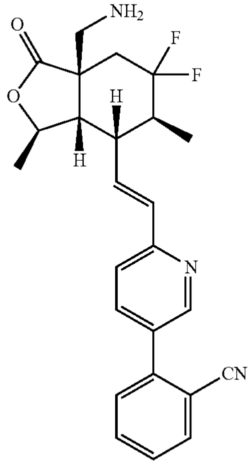

Example 76

Step A: Preparation of Compound 76-1

To a solution of the product obtained in Example 1 (22.7 mg, 0.056 mmol) in dry THF (0.5 ml) which had been purged with nitrogen gas was added a 1M solution of lithium hexamethyldisilazide in THF (0.067 mL, 0.067 mmol) at −5° C. (ice/sat. NaCl bath). The resulting yellow solution was stirred for 20 minutes then a solution of N-(bromomethyl)phthalimide (25.4 mg, 0.106 mmol) in dry THF (0.5 mL) was added. The reaction mixture was stirred for 35 minutes then quenched with saturated aqueous ammonium chloride and the mixture was extracted with ethyl acetate. The organic layer was washed with brine, dried over $MgSO_4$, and concentrated in vacuo. The residue by preparative TLC on silica gel (500 micron silica gel plate eluted with 1:1 EtOAc/hexane) to afford impure 76-1 as a yellow oil which was used without further purification in the next step.

Step B: Preparation of Example 76

To a solution of the product obtained in Step A above (27.0 mg, 0.048 mmol) in dry toluene (0.5 ml) was added methylhydrazine (0.025 mL, 0.476 mmol) at room temperature. The reaction was stirred for 2.5 hours then additional methylhydrazine (0.025 mL) was added. The reaction was stirred for an additional 40 minutes then quenched with 2 N HCl and the mixture was concentrated in vacuo. The aqueous residue was dissolved in 2:1:1 acetonitrile/DMSO/water and purified by HPLC (30×100 mm Waters SunFire™ column; 5 micron; 35 mL/min.; 210 nM; 10% to 60% $CH_3CN$+0.05% TFA/water+0.05% TFA over 15 minutes. The fractions containing the title compound (eluted at 40% $CH_3CN$+0.05% TFA/water+0.05% TFA) were combined and lyophilized over the weekend to afford Example 76 as a white solid. LC/MS: m/e 438.1 $(M+H)^+$.

EXAMPLE 77

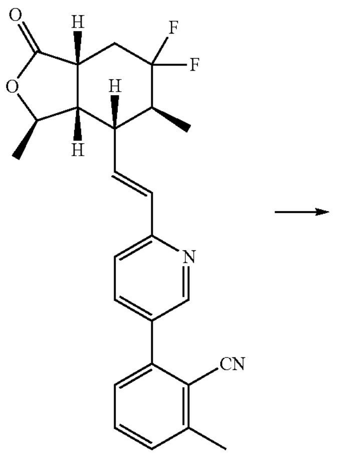

Example 1

-continued

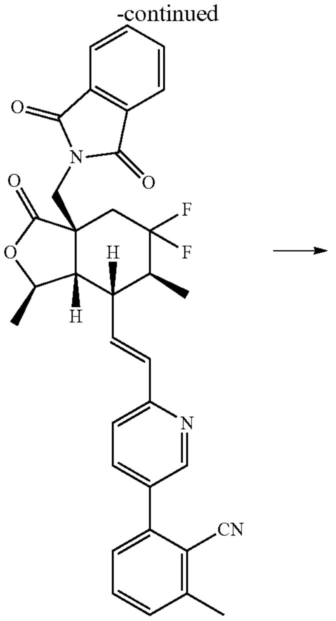

77-1

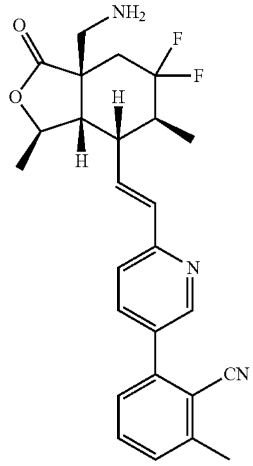

Example 77

Step A: Preparation of Compound 77-1

Compound of Example 1 (80.0 mg, 0.189 mmol) in dry THF (0.7 mL), which had been purged with nitrogen gas, was added a 0.5 M solution of potassium hexamethyldisilazide in toluene (0.606 mL, 0.303 mmol) at −5° C. (ice/NaCl bath). The reaction vessel was purged with nitrogen. The resulting brown solution was stirred for 5 minutes then a solution of N-(bromomethyl)phthalimide (62.0 mg, 0.258 mmol) in dry THF (0.4 mL) was added dropwise. After addition, the reaction vessel evacuated and purged with nitrogen. The resulting pale orange solution was stirred under nitrogen for 15 minutes then quenched with saturated aqueous $NH_4Cl$. Ethyl acetate was added and the mixture was stirred for 30 minutes then the layers were separated. The organic layer was washed with brine, dried over $MgSO_4$, and concentrated in vacuo. The residue was purified by silica gel chromatography on an Isco CombiFlash® Rf system (12 g silica gel, 30 mL/min, 254 nM, 0% to 50% EtOAc/hexane). The fractions containing the title compound (eluted at ~48% EtOAc/hexane) were combined and evaporated to give the 77-1 as a white foam.

Step B: Preparation of Example 77

To a solution of 77-1 (71.6 mg, 0.123 mmol) in dry toluene (1 mL) was added methylhydrazine (0.066 mL, 1.231 mmol)

at room temperature. After 45 minutes, additional methylhydrazine (0.020 mL) was added. The reaction was stirred for 75 minutes then quenched with 2 N HCl and the mixture was stirred for 1 hour before concentrating in vacuo. The residue was dissolved in 2:1:1 acetonitrile/DMSO/water and purified by HPLC (30×100 mm Waters SunFire™ column; 5 micron; 35 mL/min.; 210 nM; 10% to 60% $CH_3CN$+0.05% TFA/water+0.05% TFA over 15 minutes). Fractions containing the title compound (eluted at ~40% $CH_3CN$+0.05% TFA/water+0.05% TFA) were combined and lyophilized overnight to afford the compound of Example 77 as a white solid. LC/MS: m/e 452.1 $(M+H)^+$

EXAMPLE 78

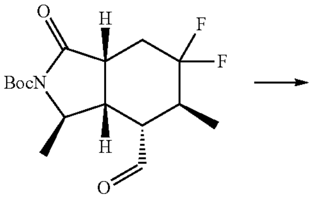

Intermediate 2

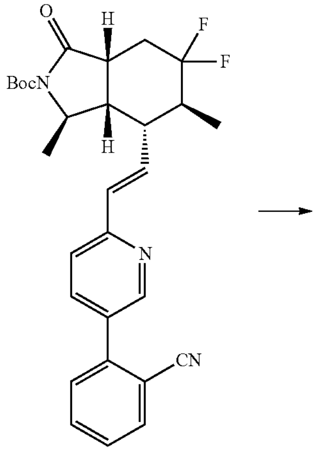

78-1

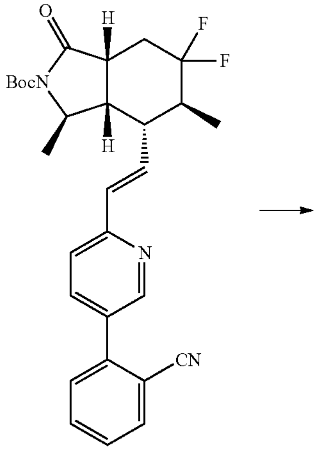

78-2

-continued

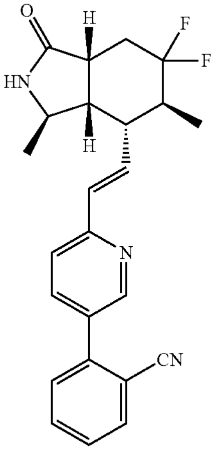

Example 78

Step A: Preparation of Compound 78-1

Intermediate 2 was converted to compound 78-1 following the protocols described in Experiment 1.

Step B: Preparation of Example 78

To a solution of Compound 78-2 (61 mg, 0.122 mmol) in 2 mL DCM was added 2 mL TFA and the resulting solution was stirred for 30 minutes. Upon completion of the reaction, the reaction mixture was evaporated to dryness, and diluted with ethyl acetate, washed with saturated $NaHCO_3$, then with brine, the organic layer was dried over $MgSO_4$, and the solvent was removed under reduced pressure. The crude product was purified using 0 to 100% ethyl acetate in hexanes to provide the compound of Example 78. NMR: ($CDCl_3$) δ 8.71 (m, 1H), 7.92 (m, 1H), 7.80 (m, 1H), 7.69 (m, 2H), 7.32 (d, J=6.8 Hz, 1H), 6.66 (m, 2H), 5.80 (br-s, 1H), 3.90 (m, 1H), 2.73 (m, 2H), 2.51 (m, 1H), 2.28 (m, 1H), 2.03 (m, 1H), 1.77 (m, 1H), 1.31 (d, J=5.6 Hz, 3H), 1.07 (d, J=6.8 Hz, 3H). m/e 430.2 (M+Na).

EXAMPLE 79

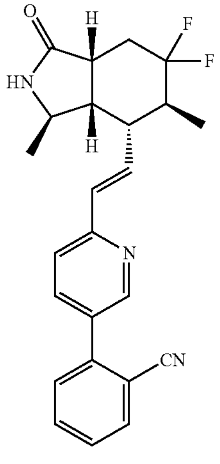

79-1

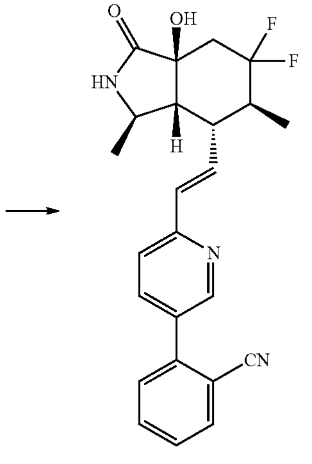

Example 79

The compound obtained in Example 78 upon treatment with LHMDS and exposure of the generated anion to an atmosphere of oxygen as described in the method used to make the product shown in Example 8, gives the title product. m/e 424.2 (M+H).

The activity of the compounds of Formula I can be determined by the following procedures.

In Vitro Testing Procedure for Thrombin Receptor Antagonists:

The following binding assays were used to determine the ability of the inventive compounds to inhibit the PAR-1 receptor.

Preparation of [$^3$H]haTRAP

A(pF-F)R(ChA)(hR)($I_2$—Y)—$NH_2$ (1.03 mg) and 10% Pd/C (5.07 mg) were suspended in DMF (250 μl) and diisopropylethylamine (10 μL). The vessel was attached to the tritium line, frozen in liquid nitrogen and evacuated. Tritium gas (342 mCi) was then added to the flask, which was stirred at room temperature for 2 hours. At the completion of the reaction, the excess tritium was removed and the reacted peptide solution was diluted with DMF (0.5 ml) and filtered to remove the catalyst. The collected DMF solution of the crude peptide was diluted with water and freeze dried to remove the labile tritium. The solid peptide was redissolved in water and the freeze drying process repeated. The tritiated peptide ([$^3$H]haTRAP) was dissolved in 0.5 ml of 0.1% aqueous TFA and purified by HPLC using the following conditions: column, Vydac™ C18, 25 cm×9.4 mm I.D.; mobile phase, (A) 0.1% TFA in water, (B) 0.1% TFA in $CH_3CN$; gradient, (A/B) from 100/0 to 40/60 over 30 min; flow rate, 5 ml/min; detection, UV at 215 nm. The radiochemical purity of [$^3$H]haTRAP was 99% as analyzed by HPLC. A batch of 14.9 mCi at a specific activity of 18.4 Ci/mmol was obtained.

Preparation of Platelet Membranes

Platelet membranes were prepared using a modification of the method of Natarajan et al. (Natarajan et al, *Int. J. Peptide Protein Res.* 45:145-151 (1995)) from 20 units of platelet concentrates obtained from the North Jersey Blood Center (East Orange, N.J.) within 48 hours of collection. All steps were carried out at 4° C. under approved biohazard safety conditions. Platelets were centrifuged at 100×g for 20 minutes at 4° C. to remove red cells. The supernatants were decanted and centrifuged at 3000×g for 15 minutes to pellet platelets. Platelets were re-suspended in 10 mM Tris-HCl, pH 7.5, 150 mM NaCl, 5 mM EDTA, to a total volume of 200 ml and centrifuged at 4400×G for 10 minutes. This step was repeated two additional times. Platelets were re-suspended in 5 mM Tris-HCl, pH 7.5, 5 mM EDTA to a final volume of approximately 30 mL and were homogenized with 20 strokes in a Dounce™ homogenizer. Membranes were pelleted at 41,000×G, re-suspended in 40-50 mL 20 mM Tris-HCl, pH 7.5, 1 mM EDTA, 0.1 mM dithiothreitol, and 10 mL aliquots were frozen in liquid $N_2$ and stored at −80° C. To complete membrane preparation, aliquots were thawed, pooled, and homogenized with 5 strokes of a Dounce homogenizer. Membranes were pelleted and washed 3 times in 10 mM triethanolamine-HCl, pH 7.4, 5 mM EDTA, and re-suspended in 20-25 mL 50 mM Tris-HCl, pH 7.5, 10 mM $MgCl_2$, 1 mM EGTA, and 1% DMSO. Aliquots of membranes were frozen in liquid $N_2$ and stored at −80° C. Membranes were stable for at least 3 months. 20 units of platelet concentrates typically yielded 250 mg of membrane protein. Protein concentration was determined by a Lowry assay (Lowry et al., *J. Biol. Chem.,* 193:265-275 (1951)).

High Throughput Thrombin Receptor Radioligand Binding Assay

Thrombin receptor antagonists were screened using a modification of the thrombin receptor radioligand binding assay of Ahn et al. (Ahn et al., *Mol. Pharmacol.,* 51:350-356 (1997)). The assay was performed in 96 well Nunc plates (Cat. No. 269620) at a final assay volume of 200 μl. Platelet membranes and [$^3$H]haTRAP were diluted to 0.4 mg/ml and 22.2 nM, respectively, in binding buffer (50 mM Tris-HCl, pH 7.5, 10 mM $MgCl_2$, 1 mM EGTA, 0.1% BSA). Stock solutions (10 mM in 100% DMSO) of test compounds were further diluted in 100% DMSO. Unless otherwise indicated, 10 μl of diluted compound solutions and 90 μL of radioligand (a final concentration of 10 nM in 5% DMSO) were added to each well, and the reaction was started by the addition of 100 μl of membranes (40 μg protein/well). The binding was not significantly inhibited by 5% DMSO. Compounds were tested at three concentrations (0.1, 1 and 10 μM). The plates were covered and vortex-mixed gently on a Lab-Line™ Titer Plate Shaker for 1 hour at room temperature. Packard UniFilter™ GF/C filter plates were soaked for at least 1 hour in 0.1% polyethyleneimine. The incubated membranes were harvested using a Packard FilterMate™ Universal Harvester and were rapidly washed four times with 300 μl ice cold 50 mM Tris-HCl, pH 7.5, 10 mM $MgCl_2$, 1 mM EGTA. MicroScint™ 20 scintillation cocktail (25 μl) was added to each well, and the plates were counted in a Packard TopCount™ Microplate Scintillation Counter. The specific binding was defined as the total binding minus the nonspecific binding observed in the presence of excess (50 μM) unlabeled haTRAP. The % inhibition by a compound of [$^3$H]haTRAP binding to thrombin receptors was calculated from the following relationship:

$$\%\ \text{Inhibition} = \frac{\text{Total binding} - \text{Binding in the presence of a test compound}}{\text{Total binding} - \text{Nonspecific binding}} \times 100$$

Materials

A(pF-F)R(ChA)(hR)Y—$NH_2$ and A(pF-F)R(ChA)(hR)($I_2$—Y)—$NH_2$, were custom synthesized by AnaSpec Inc. (San Jose, Calif.). The purity of these peptides was >95%. Tritium gas (97%) was purchased from EG&G Mound, Miamisburg, Ohio. The gas was subsequently loaded and stored on an IN/US Systems Inc. Trisorber. MicroScint™ 20 scintillation cocktail was obtained from Packard Instrument Co.

The compounds of Example 2, 10 and 13 were tested in the assay described above and the data collected for these compounds is provided in Table 7 below.

TABLE 7

| Example | Thrombin receptor radioligand binding assay Ki (nM) |
|---|---|
| 2 | 3 |
| 10 | 3 |
| 13 | 3 |

Par-1 FLIPR Assay

HEK 293 Cells were grown in media containing DMEM, 10% FBS pen/strep/L-Glutamine and non-essential amino acids. The cells were plated in 384-well PDL coated plates at 12000 cells/well and incubated overnight at 37° C./5% $CO_2$. Media was then removed from the cells, which were then incubated with buffer (Hank's containing HEPES and Chaps) containing FLIPR calcium-5 dye, made with buffer containing probenecid, for 60 minutes at 37° C. Varying concentrations of compound in a final concentration of 5% DMSO were then added to the cells and incubated at 25° C. for 30 minutes. The plates were then added to the FLIPR Tetra and the device added a concentration of a PAR1 selective receptor-activating peptide with the sequence Ala-parafluoroPhe-Arg-Cha-Cit-Try-Nh2 (prepared in water) at a concentration equal to the effective concentration that achieves 80% activation of signaling on the day of the experiment. The range was from 1.4-2.0 μM peptide. The FLIPR reads at an excitation wavelength of 480 nm and an emission wavelength of 535 nm, and performs 60 scans over a 1-2 min reading time. The data were analyzed by taking the peak signal over a portion of the range of the 60 scans and dividing this signal by the minimum signal for that same range. The data were expressed as percent inhibition of the maximum divided by the minimum signal achieved at 80% activation produced by the PAR1 activating peptide on the test day.

The following compounds were tested in the assay described above and the data collected for these compounds is provided in Table 8 below.

TABLE 8

| Example | Par-1 FLIPR IC50 (nM) |
|---|---|
| 1 | 1.6 |
| 2 | 5.01 |
| 4 | 2.7 |
| 5 | 4.7 |
| 7 | 7.2 |
| 8 | 2 |
| 9 | 4.5 |
| 10 | 8.1 |
| 11 | 3.4 |
| 12 | 10.9 |
| 13 | 17 |
| 14 | 5.1 |
| 15 | 2.7 |
| 16 | 8 |
| 17 | 38.6 |
| 18 | 3.3 |
| 19 | 3 |
| 20a | 0.9 |
| 20b | 1.2 |
| 21a | 2.5 |
| 21b | 1.2 |
| 22a | 1.9 |
| 22b | 2.2 |
| 23a | 3.1 |
| 23b | 1.2 |
| 24 | 40.7 |
| 25 | 3.3 |
| 26 | 1.2 |
| 27 | 7.5 |
| 28 | 0.9 |
| 29a | 2.1 |
| 29b | 1 |
| 30 | 6.4 |
| 31 | 3.1 |
| 32 | 1.4 |
| 33 | 9.7 |
| 34 | 6.4 |
| 35 | 4.3 |
| 36 | 4.1 |
| 37 | 5.3 |
| 38 | 4.7 |
| 39 | 2.2 |
| 40 | 3.9 |
| 41 | 6.5 |
| 42 | 2.4 |
| 43 | 1.3 |
| 44 | 1.6 |
| 45 | 4.4 |
| 46 | 3.1 |
| 47 | 5.7 |
| 48 | 3 |
| 49 | 10.4 |
| 50 | 2.7 |
| 51 | 10.2 |
| 52 | 4.3 |

TABLE 8-continued

| Example | Par-1 FLIPR IC50 (nM) |
|---|---|
| 53 | 26 |
| 54 | 7.1 |
| 55 | 6.3 |
| 56 | 6.1 |
| 57 | 2.8 |
| 58 | 3 |
| 59 | 3 |
| 60 | 3.4 |
| 61 | 33.3 |
| 62 | 1.7 |
| 63 | 2.3 |
| 64 | 2.9 |
| 65 | 2.7 |
| 66 | 3.5 |
| 67 | 3.7 |
| 68 | 7 |
| 70 | 15.6 |
| 71 | 4.8 |
| 72 | 2.5 |
| 73 | 3.3 |
| 74 | 872 |
| 75 | 345.6 |
| 76 | 2.3 |
| 77 | 1.2 |
| 78 | 1.5 |
| 79 | 5.8 |

In Vitro Testing Procedure from $CB_2$ Receptor Antagonists:

The following binding assay could be used to determine the ability of the inventive compounds to inhibit the $CB_2$ receptor.

Cannabinoid $CB_2$ Receptor Binding Assay

Binding to the human cannabinoid $CB_2$ receptor is carried out using the procedure of Showalter, et al. (1996, *J. Pharmacol Exp Ther.* 278(3), 989-99), with minor modifications. All assays are carried out in a final volume of 100 ul. Test compounds are re-suspended to 10 mM in DMSO, then serially diluted in 50 mM Tris, pH 7.1, 3 mM $MgCl_2$, 1 mM EDTA, 50% DMSO. Aliquots (10 ul) of each diluted sample are then transferred into individual wells of a 96-well microtiter plate. Membranes from human $CB_2$ transfected CHO/Ki cells (Receptor Biology, Inc) are re-suspended in binding buffer (50 mM Tris, pH 7.1, 3 mM $MgCl_2$, 1 mM EDTA, 0.1% fatty acid free bovine serum albumin), then added to the binding reaction (~15 ug in 50 ul per assay). The reactions are initiated with the addition of [$^3$H] CP-55, 940 diluted in binding buffer (specific activity=180 Ci/mmol; New England Nuclear, Boston, Mass.). The final ligand concentration in the binding reaction is 0.48 nM. Following incubation at room temperature for 2 hours, membranes are harvested by filtration through pretreated (0.5% polyethylenimine; Sigma P-3143) GF-C filter plates (Unifilter-96, Packard) using a TomTec™ Mach 3U 96-well cell harvester (Hamden, Conn.). Plates are washed 10 times in 100 ul binding buffer, and the membranes are allowed to air dry. Radioactivity on membranes is quantitated following addition of Packard Omniscint™ 20 scintillation fluid using a TopCount™ NXT Microplate Scintillation and Luminescence Counter (Packard, Meriden, Conn.). Non-linear regression analysis is performed using Prism™ 20b. (GraphPad Software, San Diego, Calif.).

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

We claim:

1. A compound of the formula:

Formula I

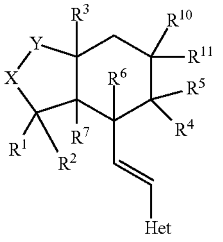

or a pharmaceutically acceptable salt thereof, wherein:

X is —O—, —N(R), —C($R^8$)($R^9$) or —C(O)—;

Y is —O—, —N(R), —C($R^8$)($R^9$) or —C(O)—;

R is H, alkyl or —$S(O)_2$—$R^9$ $R^1$ is H, alkyl or haloalkyl;

$R^2$ is H, alkyl or haloalkyl;

$R^3$ is —$N_3$, —CN; halogen, —$OR^{12}$, —N($R^{25}$)($R^{26}$), —C(O)$OR^{12}$, —C(O)N($R^{25}$)($R^{26}$), —$SO_2$($R^{12}$), $R^{17}$-alkyl, $R^{17}$-cycloalkyl, $R^{17}$-aryl, $R^{17}$-heterocycloalkyl or $R^{17}$-heteroaryl;

$R^4$ is H, alkyl or haloalkyl;

$R^5$ is H, alkyl or haloalkyl;

$R^6$ is H or alkyl;

$R^7$ is H or alkyl;

$R^8$ independently is H or alkyl;

$R^9$ independently is H or alkyl;

$R^{10}$ is fluoro;

$R^{11}$ is fluoro;

$R^{12}$ independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{13}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{14}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, —C(O)$R^{12}$, —$S(O)_2$—$R^{12}$, $R^{17}$-heteroaryl, $R^{17}$-heteroarylalkyl or $R^{17}$-heteroarylalkenyl;

or $R^{13}$ and $R^{14}$ taken together with the nitrogen atom to which they are attached are —$(CH_2)_4$—, —$(CH_2)_5$— or —$(CH_2)_2$—N($R^8$)—$(CH_2)_2$—;

Het is a 5- or 6-membered heterocycloalkyl, heterocyclenyl or a heteroaryl ring containing 3 to 5 carbon atoms and 1 or 2 heteroatoms selected from the group consisting of N, O or S, with the proviso that there are no adjacent oxygen or sulfur atoms present in said groups, and when Het is a N-containing heteraromatic group with one heteroatom present, then the ring nitrogen can form an N-oxide or a quaternary group with an alkyl group; wherein: 1) Het is attached to the double bond by a carbon atom ring member of Het; and 2) Het is substituted by 1 to 4 moieties, W, where each W is independently hydrogen, alkyl, haloalkyl, $R^{17}$-cycloalkyl, $R^{17}$-heterocycloalkyl, $R^{16}$-alkenyl, $R^{17}$-aryl, $R^{17}$-heteroaryl, $R^{17}$-arylalkyl, $R^{17}$-arylalkenyl, $R^{17}$-heteroarylalkyl, $R^{17}$-heteroarylalkenyl, hydroxyalkyl, dihydroxyalkyl, aminoalkyl, alkylaminoalkyl, di-(alkyl)-aminoalkyl, alkoxy, -alkyl-SH, —S-alkyl, alkenyloxy, halogen, —$NR^{13}R^{14}$, —CN, —OH, —C(O)$OR^{12}$, —$COR^{12}$, —$OS(O_2)CF_3$, —$CH_2OCH_2CF_3$, —C(O)$NR^{13}NR^{14}$, —$OCHR^{15}$-phenyl, phenoxyalkyl, —$NR^8COR^{12}$, —$NR^8SO_2R^{12}$, —C(O)$NR^{13}R^{14}$, —OC$(R^{15})_2$ $COOR^{12}$, —OC$(R^{15})_2$C(O)$NR^{13}R^{14}$, alkoxy optionally substituted by alkyl, amino or —$NR^8$C(O)$OR^{12}$, or alkyl optionally substituted with —$NR^{13}R^{14}$, —$NR^{13}COR^{12}$, —$NR^8CONR^{13}R^{14}$, —$NR^8$C(O) $OR^{12}$, —$NR^8S(O)_2NR^{13}R^{14}$, —C(O)$OR^{12}$, —$CONR^{13}R^{14}$ or —OH;

$R^{15}$ independently is H, alkyl, cycloalkyl, alkoxyalkyl, hydroxyalkyl, aminoalkyl or phenyl;

$R^{16}$ is 1 to 3 moieties and each $R^{16}$ is independently hydrogen, halogen, —OH, alkoxy, -alkyl-SH, —S-alkyl, $R^{24}$-aryl, $R^{24}$-heteroaryl, $R^{24}$-heterocycloalkyl, $R^{24}$-cycloalkyl, $R^{24}$-cycloalkenyl, $R^{24}$-heterocyclenyl, —OC(O)$R^{20}$, —C(O)$OR^{20}$, —C(O)$R^{20}$, —C(O)$NR^{21}R^{22}$, —$NR^{21}R^{22}$, —$NR^8$C(O)$R^{20}$, —$NR^8$C(O)$NR^{21}R^{22}$, —$NR^8SO_2R^{20}$, —OC(O)$NR^{21}R^{22}$, $R^{23}$-alkenyloxy, $R^{23}$-alkynyloxy, $R^{23}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —$NR^8SO_2NHR^{21}$ or —C(=$NOR^{18}$)$R^{19}$;

$R^{17}$ is 1 to 3 moieties and each $R^{17}$ independently hydrogen, $R^{23}$-alkyl, halogen, —CN, —$NO_2$, —OH, $R^{23}$-alkoxy, —OC(O)$R^{20}$, —C(O)$OR^{20}$, —C(O)$R^{20}$, —C(O)$NR^{21}R^{22}$, —$NR^{21}R^{22}$, —$NR^8$C(O)$R^{20}$, —$NR^8$C(O)$NR^{21}R^{22}$, —$NR^8SO_2R^{20}$, —OC(O) $NR^{21}R^{22}$, —S(O)$R^{20}$, —$S(O)_2R^{20}$, —$SR^{20}$, —$SO_2NR^{21}R^{22}$, —$NHCOR^{20}$, —C(NH)—$NH_2$, —C(O)$NR^{21}R^{22}$, $R^{23}$-alkenyloxy, $R^{23}$-alkynyloxy, $R^{24}$-cycloalkyl, $R^{24}$-cycloalkenyl, $R^{24}$-heterocycloalkyl, $R^{24}$-aryl, $R^{24}$-heteroaryl, $R^{24}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —$NR^8SO_2NHR^{21}$ or —C(=$NOR^{18}$)$R^{19}$;

$R^{18}$ is H, alkyl, phenyl or benzyl;

$R^{19}$ is H, alkyl, phenyl or benzyl;

$R^{20}$, $R^{21}$ and $R^{22}$ are independently hydrogen, alkyl, haloalkyl, alkenyl, alkynyl, aryl, aralkyl, cycloalkyl, halocycloalkyl or alkoxyalkyl;

$R^{23}$ is 1 to 3 moieties and each $R^{23}$ is independently hydrogen, halogen, —OH, alkyl, haloalkyl, alkoxy, —CN, amino, alkylamino, dialkylamino, di(alkyl)amino, haloalkoxy, hydroxyalkyl, —CHO, —C(O)alkylamino, —C(O)alkylamino, —NHC(O)alkyl or —N(alkyl)C(O) alkyl;

$R^{24}$ is 1 to 3 moieties and each $R^{24}$ is independently hydrogen, halogen, —OH, alkyl, haloalkyl, alkoxy, —CN, amino, alkylamino, dialkylamino, di(alkyl)amino, haloalkoxy, hydroxyalkyl, —CHO, —C(O)alkylamino, C(O)alkylamino, NHC(O)alkyl or —N(alkyl)C(O) alkyl;

$R^{25}$ is H, $R^{17}$-alkyl, $R^{17}$-cycloalkyl, $R^{17}$-aryl, $R^{17}$-heterocycloalkyl, $R^{17}$-aryl or $R^{17}$-heteroaryl; and $R^{26}$ is H, OH, —C(O)N($R^{21}$)($R^{22}$), —C(S)N($R^{21}$)($R^{22}$), —C(O)$R^{12}$, —$S(O)_2R^{12}$; $R^{17}$-alkyl, $R^{17}$-cycloalkyl, $R^{17}$-aryl, $R^{17}$-heterocycloalkyl, or $R^{17}$-heteroaryl.

2. The compound as defined in claim 1 or a pharmaceutically acceptable salt thereof, which has the structural formula

II

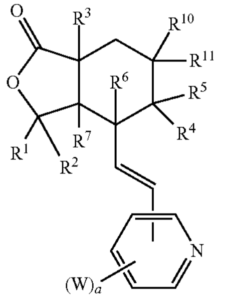

wherein:

$R^1$ is H, alkyl or haloalkyl;

$R^2$ is H, alkyl or haloalkyl;

$R^3$ is —$N_3$, —CN; halogen, —$OR^{12}$, —$N(R^{25})(R^{26})$, —$C(O)OR^{12}$, —$C(O)N(R^{25})(R^{26})$, —$SO_2(R^{12})$, $R^{17}$-alkyl, $R^{17}$-cycloalkyl, $R^{17}$-aryl, $R^{17}$-heterocycloalkyl or $R^{17}$-heteroaryl;

$R^4$ is H, alkyl or haloalkyl;

$R^5$ is H, alkyl or haloalkyl;

$R^6$ is H or alkyl;

$R^7$ is H or alkyl;

$R^8$ independently is H or alkyl;

$R^{10}$ is fluoro;

$R^{11}$ is fluoro;

$R^{12}$ independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{13}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{14}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, —$C(O)R^{12}$, —$S(O)_2$—$R^{12}$, $R^{17}$-heteroaryl, $R^{17}$-heteroarylalkyl or $R^{17}$-heteroarylalkenyl;

or $R^{13}$ and $R^{14}$ taken together with the nitrogen atom to which they are attached are —$(CH_2)_4$—, —$(CH_2)_5$— or —$(CH_2)_2$—$N(R^8)$—$(CH_2)_2$—;

W is independently hydrogen, alkyl, haloalkyl, $R^{17}$-cycloalkyl, $R^{17}$-heterocycloalkyl, $R^{16}$-alkenyl, $R^{17}$-aryl, $R^{17}$-heteroaryl, $R^{17}$-arylalkyl, $R^{17}$-arylalkenyl, $R^{17}$-heteroarylalkyl, $R^{17}$-heteroarylalkenyl, hydroxyalkyl, dihydroxyalkyl, aminoalkyl, alkylaminoalkyl, di-(alkyl)-aminoalkyl, alkoxy, -alkyl-SH, —S-alkyl, alkenyloxy, halogen, —$NR^{13}R^{14}$, —CN, —OH, —$C(O)OR^{12}$, —$COR^{12}$, —$OS(O_2)CF_3$, —$CH_2OCH_2CF_3$, —$C(O)NR^{13}NR^{14}$, —$OCHR^{15}$-phenyl, phenoxyalkyl, —$NR^8COR^{12}$, —$NR^8SO_2R^{12}$, —$C(O)NR^{13}R^{14}$, —$OC(R^{15})_2COOR^{12}$, —$OC(R^{15})_2C(O)NR^{13}R^{14}$, alkoxy optionally substituted by alkyl, amino or —$NR^8C(O)OR^{12}$, or alkyl optionally substituted with —$NR^{13}R^{14}$, —$NR^{13}COR^{12}$, —$NR^8CONR^{13}R^{14}$, —$NR^8C(O)OR^{12}$, —$NR^8S(O)_2NR^{13}R^{14}$, —$C(O)OR^{12}$, —$CONR^{13}R^{14}$or —OH;

$R^{15}$ independently is H, alkyl, cycloalkyl, alkoxyalkyl, hydroxyalkyl, aminoalkyl or phenyl;

$R^{16}$ is 1 to 3 moieties and each $R^{16}$ is independently hydrogen, halogen, —OH, alkoxy, -alkyl-SH, —S-alkyl, $R^{24}$-aryl, $R^{24}$-heteroaryl, $R^{24}$-heterocycloalkyl, $R^{24}$-cycloalkyl, $R^{24}$-cycloalkenyl, $R^{24}$-heterocyclenyl, —$OC(O)R^{20}$, —$C(O)OR^{20}$, —$C(O)R^{20}$, —$C(O)NR^{21}R^{22}$, —$NR^{21}R^{22}$, —$NR^8C(O)R^{20}$, —$NR^8C(O)NR^{21}R^{22}$, —$NR^8SO_2R^{20}$, —$OC(O)NR^{21}R^{22}$, $R^{23}$-alkenyloxy, $R^{23}$-alkynyloxy, $R^{23}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —$NR^8SO_2NHR^{21}$ or —$C(=NOR^{18})R^{19}$;

$R^{17}$ is 1 to 3 moieties and each $R^{17}$ independently hydrogen, $R^{23}$-alkyl, halogen, —CN, —$NO_2$, —OH, $R^{23}$-alkoxy, —$OC(O)R^{20}$, —$C(O)OR^{20}$, —$C(O)R^{20}$, —$C(O)NR^{21}R^{22}$, —$NR^{21}R^{22}$, —$NR^8C(O)R^{20}$, —$NR^8C(O)NR^{21}R^{22}$, —$NR^8SO_2R^{20}$, —$OC(O)NR^{21}R^{22}$, —$S(O)R^{20}$, —$S(O)_2R^{20}$, —$SR^{20}$, —$SO_2NR^{21}R^{22}$, —$NHCOR^{20}$, —C(NH)—$NH_2$, —$C(O)NR^{21}R^{22}$, $R^{23}$-alkenyloxy, $R^{23}$-alkynyloxy, $R^{24}$-cycloalkyl, $R^{24}$-cycloalkenyl, $R^{24}$-heterocycloalkyl, $R^{24}$-aryl, $R^{24}$-heteroaryl, $R^{24}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —$NR^8SO_2NHR^{21}$ or —$C(=NOR^{18})R^{19}$;

$R^{18}$ is H, alkyl, phenyl or benzyl;

$R^{19}$ is H, alkyl, phenyl or benzyl;

$R^{20}$, $R^{21}$ and $R^{22}$ are independently hydrogen, alkyl, haloalkyl, alkenyl, alkynyl, aryl, aralkyl, cycloalkyl, halocycloalkyl or alkoxyalkyl;

$R^{23}$ is 1 to 3 moieties and each $R^{23}$ is independently hydrogen, halogen, —OH, alkyl, haloalkyl, alkoxy, —CN, amino, alkylamino, dialkylamino, di(alkyl)amino, haloalkoxy, hydroxyalkyl, —CHO, —C(O)alkylamino, —C(O)alkylamino, —NHC(O)alkyl or —N(alkyl)C(O)alkyl;

$R^{24}$ is 1 to 3 moieties and each $R^{24}$ is independently hydrogen, halogen, —OH, alkyl, haloalkyl, alkoxy, —CN, amino, alkylamino, dialkylamino, di(alkyl)amino, haloalkoxy, hydroxyalkyl, —CHO, —C(O)alkylamino, C(O)alkylamino, NHC(O)alkyl or —N(alkyl)C(O)alkyl;

$R^{25}$ is H, $R^{17}$-alkyl, $R^{17}$-cycloalkyl, $R^{17}$-aryl, $R^{17}$-heterocycloalkyl, $R^{17}$-aryl or $R^{17}$-heteroaryl;

$R^{26}$ is H, OH, —$C(O)N(R^{21})(R^{22})$, —$C(S)N(R^{21})(R^{22})$, —$C(O)R^{12}$, —$S(O)_2R^{12}$; $R^{17}$-alkyl, $R^{17}$-cycloalkyl, $R^{17}$-aryl, $R^{17}$-heterocycloalkyl, or $R^{17}$-heteroaryl; and a is 1 or 2.

3. The compound as defined in claim 2 which has the structural formula

VI

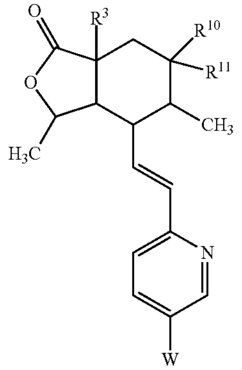

or a pharmaceutically acceptable salt thereof wherein

W is optionally substituted phenyl, optionally substituted heterocycloalkyl or optionally substituted heteroaryl, wherein the optionally substitutents are halo, alkyl, haloalkyl, cyano, —OH, alkoxy, —C(O)$NH_2$, —C(O)N(H)(alkyl), —C(O)N(alkyl)(alkyl), haloalkoxy or heteroaryl, which is optionally substituted by alkyl or halogen, and wherein the heterocycloalkyl group is piperidyl, pyrrolidinyl, piperazinyl, morpholinyl, thiomorpholinyl, thiazolidinyl, oxetanyl, azetindinyl, 1,3-dioxanyl, 1,4-dioxanyl, tetrahydrofuranyl, tetrahydrothiopyranyl or tetrahydrothiophenyl; and the heteroaryl group is independently pyridyl, pyrazinyl, furanyl, thienyl, pyrimidinyl, pyridone, isoxazolyl, isothiazolyl, diazolyl, oxazolyl, oxadiazolyl, thiazolyl, pyrazolyl, oxadiazolyl, tetrazolyl, pyrimidyl, furazanyl, pyrrolyl, pyrazolyl, triazolyl, tetrazolyl, 1,2,4-thiadiazolyl, pyrazinyl, pyridazinyl, quinoxalinyl, phthalazinyl, oxindolyl and indolyl.

4. The compound as defined in claim 1 or a pharmaceutically acceptable salt thereof wherein:

W is an optionally mono- or di substituted phenyl wherein the optional substituents are halogen, —CN, alkyl, haloalkoxy or $R^{17}$-heteroaryl;

$R^{10}$ and $R^{11}$ are both fluoro;

$R^3$ is $N^3$ halogen; —OH, alkoxy, —C(O)$OR^{12}$, —C(O)N(H)($R^{26}$), —N($R^{25}$)($R^{26}$), —$SO_2R^{12}$, $R^{17}$-alkyl, $R^{17}$-cycloalkyl, $R^{17}$-phenyl, $R^{17}$-heterocycloalkyl, or $R^{17}$-heteroaryl;

$R^{12}$ is H, alkyl cycloalkyl, optionally substituted phenyl or optionally substituted heteroaryl and the optional substituents are halogen, alkyl, —CN, —$NH_2$, —N(H)(alkyl) or —N(alkyl)(alkyl);

$R^{17}$ is 1 to 3 substituents and is independently H; halogen; —CN; —OH, alkoxy; —C(O)$OR^{20}$; —$NH_2$; —N(H)(alkyl); —N(alkyl)(alkyl); optionally substituted phenyl; optionally substituted heteroaryl, wherein the optional substituents are halogen, alkyl, $NH_2$; —N(H)(alkyl); —N(alkyl)(alkyl) or phenyl;

$R^{25}$ is H or alkyl;

$R^{22}$ is H, alkyl, hydroxyalkyl or cycloalkyl; and $R^{26}$ is H, —OH; alkyl; $R^{17}$-alkyl; cycloalkyl; —C(O)$R^{12}$; cycloalkyl; phenyl, heterocycloalkyl or heteroaryl; —C(S)N(H)(alkyl); —C(S)N(H)(cycloalkyl); —$S(O)_2$ alkyl or —C(O)N(H)($R^{22}$).

5. The compound as defined in claim 1 or a pharmaceutically acceptable salt thereof, which has the structural formula

III

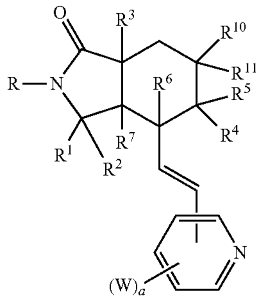

wherein:

$R^1$ is H, alkyl or haloalkyl;

$R^2$ is H, alkyl or haloalkyl;

$R^3$ is —$N_3$, —CN, halogen, —$OR^{12}$, —N($R^{25}$)($R^{26}$), —C(O)$OR^{12}$, —C(O)N($R^{25}$)($R^{26}$), —$SO_2$($R^{12}$), $R^{17}$-alkyl, $R^{17}$-cycloalkyl, $R^{17}$-aryl, $R^{17}$-heterocycloalkyl or $R^{17}$-heteroaryl;

$R^4$ is H, alkyl, or haloalkyl;

$R^5$ is H, alkyl or haloalkyl;

$R^6$ is H or alkyl;

$R^7$ is H or alkyl;

$R^8$ independently is H or alkyl;

$R^{10}$ is fluoro;

$R^{11}$ is fluoro;

$R^{12}$ independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{13}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{14}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, —C(O)$R^{12}$, —$S(O)_2$—$R^{12}$, $R^{17}$-heteroaryl, $R^{17}$-heteroarylalkyl or $R^{17}$-heteroarylalkenyl;

or $R^{13}$ and $R^{14}$ taken together with the nitrogen atom to which they are attached are —$(CH_2)_4$—, —$(CH_2)_5$— or —$(CH_2)_2$—N($R^8$)—$(CH_2)_2$—;

W is independently hydrogen, alkyl, haloalkyl, $R^{17}$-cycloalkyl, $R^{17}$-heterocycloalkyl, $R^{16}$-alkenyl, $R^{17}$-aryl, $R^{17}$-heteroaryl, $R^{17}$-arylalkyl, $R^{17}$-arylalkenyl, $R^{17}$-heteroarylalkyl, $R^{17}$-heteroarylalkenyl, hydroxyalkyl, dihydroxyalkyl, aminoalkyl, alkylaminoalkyl, di-(alkyl)-aminoalkyl, alkoxy, -alkyl-SH, —S-alkyl, alkenyloxy, halogen, —$NR^{13}R^{14}$, —CN, —OH, —C(O)$OR^{12}$, —$COR^{12}$, —OS($O_2$)$CF_3$, —$CH_2OCH_2CF_3$, —C(O)$NR^{13}NR^{14}$, —$OCHR^{15}$-phenyl, phenoxyalkyl, —$NR^8COR^{12}$, —$NR^8SO_2R^{12}$, —C(O)$NR^{13}R^{14}$, —OC($R^{15}$)$_2COOR^{12}$, —OC($R^{15}$)$_2$C(O)$NR^{13}R^{14}$, alkoxy optionally substituted by alkyl, amino or —$NR^8$C(O)$OR^{12}$, or alkyl optionally substituted with —$NR^{13}R^{14}$, —$NR^{13}COR^{12}$, —$NR^8CONR^{13}R^{14}$, —$NR^8$C(O)$OR^{12}$, —$NR^8S(O)_2R^{12}$, —$NR^8S(O)_2NR^{13}R^{14}$, —C(O)$OR^{12}$, —$CONR^{13}R^{14}$ or —OH;

$R^{15}$ independently is H, alkyl, cycloalkyl, alkoxyalkyl, hydroxyalkyl, aminoalkyl or phenyl;

$R^{16}$ is 1 to 3 moieties and each $R^{16}$ is independently hydrogen, halogen, —OH, alkoxy, -alkyl-SH, —S-alkyl, $R^{24}$-aryl, $R^{24}$-heteroaryl, $R^{24}$-heterocycloalkyl, $R^{24}$-cycloalkyl, $R^{24}$-cycloalkenyl, $R^{24}$-heterocyclenyl, —OC(O)$R^{20}$, —C(O)$OR^{20}$, —C(O)$R^{20}$, —C(O)$NR^{21}R^{22}$, —$NR^{21}R^{22}$, —$NR^8$C(O)$R^{20}$, —$NR^8$C(O)$NR^{21}R^{22}$, —$NR^8SO_2R^{20}$, —OC(O)$NR^{21}R^{22}$, $R^{23}$-alkenyloxy, $R^{23}$-alkynyloxy, $R^{23}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —$NR^8SO_2NHR^{21}$ or —C(=$NOR^{18}$)$R^{19}$;

$R^{17}$ is 1 to 3 moieties and each $R^{17}$ independently hydrogen, $R^{23}$-alkyl, halogen, —CN, —$NO_2$, —OH, $R^{23}$-alkoxy, —OC(O)$R^{20}$, —C(O)$OR^{20}$, —C(O)$R^{20}$, —C(O)$NR^{21}R^{22}$, —$NR^{21}R^{22}$, —$NR^8$C(O)$R^{20}$, —$NR^8$C(O)$NR^{21}R^{22}$, —$NR^8SO_2R^{20}$, —OC(O)$NR^{21}R^{22}$, —S(O)$R^{20}$, —$S(O)_2R^{20}$, —$SR^{20}$, —$SO_2NR^{21}R^{22}$, —$NHCOR^{20}$, —C(NH)—$NH_2$, —C(O)$NR^{21}R^{22}$, $R^{23}$-alkenyloxy, $R^{23}$-alkynyloxy, $R^{24}$-cycloalkyl, $R^{24}$-cycloalkenyl, $R^{24}$-heterocycloalkyl, $R^{24}$-aryl, $R^{24}$-heteroaryl, $R^{24}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —$NR^8SO_2NHR^{21}$ or —C(=$NOR^{18}$)$R^{19}$;

$R^{18}$ is H, alkyl, phenyl or benzyl;

$R^{19}$ is H, alkyl, phenyl or benzyl;

$R^{20}$, $R^{21}$ and $R^{22}$ are independently hydrogen, alkyl, haloalkyl, alkenyl, alkynyl, aryl, aralkyl, cycloalkyl, halocycloalkyl or alkoxyalkyl;

$R^{23}$ is 1 to 3 moieties and each $R^{23}$ is independently hydrogen, halogen, —OH, alkyl, haloalkyl, alkoxy, —CN, amino, alkylamino, dialkylamino, di(alkyl)amino, haloalkoxy, hydroxyalkyl, —CHO, —C(O)alkylamino, —C(O)alkylamino, —NHC(O)alkyl or —N(alkyl)C(O)alkyl;

$R^{24}$ is 1 to 3 moieties and each $R^{24}$ is independently hydrogen, halogen, —OH, alkyl, haloalkyl, alkoxy, —CN, amino, alkylamino, dialkylamino, di(alkyl)amino, haloalkoxy, hydroxyalkyl, —CHO, —C(O)alkylamino, C(O)alkylamino, NHC(O)alkyl or —N(alkyl)C(O)alkyl;

$R^{25}$ is H; $R^{17}$-alkyl, $R^{17}$-cycloalkyl, $R^{17}$-aryl, $R^{17}$-heterocycloalkyl; $R^{17}$-aryl, or $R^{17}$-heteroaryl;

$R^{26}$ is H, OH, —C(O)N($R^{21}$)($R^{22}$), —C(S)N($R^{21}$)($R^{22}$), —C(O)$R^{12}$, —$S(O)_2R^{12}$, $R^{17}$-alkyl, $R^{17}$-cycloalkyl; $R^{17}$-aryl; $R^{17}$-heterocycloalkyl; $R^{17}$-aryl or $R^{17}$-heteroaryl; and a is 1 or 2.

6. The compound as defined in claim 5 or a pharmaceutically acceptable salt thereof, wherein $R^{10}$ is fluoro;

$R^{11}$ is fluoro;

W is $R^{17}$-phenyl; and $R^{17}$ is 1 to 2 moieties and each $R^{17}$ is independently halogen, —CN, alkyl, haloalkoxy or $R^{24}$-heteroaryl.

7. The compound as defined in claim 1 or a pharmaceutically acceptable salt thereof, which has the structural formula

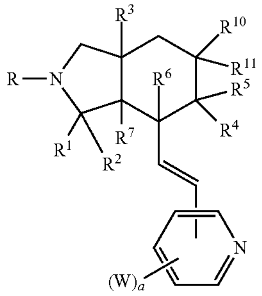

IV wherein:

$R^1$ is H, alkyl or haloalkyl;

$R^2$ is H, alkyl or haloalkyl;

$R^3$ is —$N_3$, —CN; halogen, —O$R^{12}$, —N($R^{25}$)($R^{26}$), —C(O)O$R^{12}$, —C(O)N($R^{25}$)($R^{26}$), —$SO_2$($R^{12}$), $R^{17}$-alkyl, $R^{17}$-cycloalkyl; $R^{17}$-aryl, $R^{17}$-heterocycloalkyl, $R^{17}$-aryl, or $R^{17}$-heteroaryl;

$R^4$ is H, alkyl, or haloalkyl;

$R^5$ is H, alkyl or haloalkyl;

$R^6$ is H or alkyl;

$R^7$ is H or alkyl;

$R^8$ independently is H or alkyl;

$R^{10}$ is fluoro;

$R^{11}$ is fluoro;

$R^{12}$ independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{13}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{14}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, —C(O)$R^{12}$, —$S(O)_2$—$R^{12}$, $R^{17}$-heteroaryl, $R^{17}$-heteroarylalkyl or $R^{17}$-heteroarylalkenyl;

or $R^{13}$ and $R^{14}$ taken together with the nitrogen atom to which they are attached are —$(CH_2)_4$—, —$(CH_2)_5$— or —$(CH_2)_2$—N($R^8$)—$(CH_2)_2$—;

W is independently hydrogen, alkyl, haloalkyl, $R^{17}$-cycloalkyl, $R^{17}$-heterocycloalkyl, $R^{16}$-alkenyl, $R^{17}$-aryl, $R^{17}$-heteroaryl, $R^{17}$-arylalkyl, $R^{17}$-arylalkenyl, $R^{17}$-heteroarylalkyl, $R^{17}$-heteroarylalkenyl; hydroxyalkyl; dihydroxyalkyl; aminoalkyl, alkylaminoalkyl, di-(alkyl)-aminoalkyl, alkoxy, -alkyl-SH, —S-alkyl, alkenyloxy, halogen, —N$R^{13}R^{14}$, —CN, —OH, —C(O)O$R^{12}$, —CO$R^{12}$, —OS($O_2$)$CF_3$, —$CH_2OCH_2CF_3$, —C(O)N$R^{13}$N$R^{14}$, —OCH$R^{15}$-phenyl, phenoxyalkyl, —N$R^8$CO$R^{12}$, —N$R^8SO_2R^{12}$, —C(O)N$R^{13}R^{14}$, —OC($R^{15}$)$_2$COO$R^{12}$, —OC($R^{15}$)$_2$C(O)N$R^{13}R^{14}$, alkoxy optionally substituted by alkyl, amino or —N$R^8$C(O)O$R^{12}$, or alkyl optionally substituted with —N$R^{13}R^{14}$, —N$R^{13}$CO$R^{12}$, —N$R^8$CON$R^{13}R^{14}$, —N$R^8$C(O)O$R^{12}$, —N$R^8S(O)_2R^{12}$, —N$R^8S(O)_2$N$R^{13}R^{14}$, —C(O)O$R^{12}$, —CON$R^{13}R^{14}$ or —OH;

$R^{15}$ independently is H, alkyl, cycloalkyl, alkoxyalkyl, hydroxyalkyl, aminoalkyl or phenyl;

$R^{16}$ is 1 to 3 moieties and each $R^{16}$ is independently hydrogen, halogen, —OH, alkoxy, -alkyl-SH, —S-alkyl, $R^{24}$-aryl, $R^{24}$-heteroaryl, $R^{24}$-heterocycloalkyl, $R^{24}$-cycloalkyl, $R^{24}$-cycloalkenyl, $R^{24}$-heterocyclenyl, —OC(O)$R^{20}$, —C(O)O$R^{20}$, —C(O)$R^{20}$, —C(O)N$R^{21}R^{22}$, —N$R^{21}R^{22}$, —N$R^8$C(O)$R^{20}$, —N$R^8$C(O)N$R^{21}R^{22}$, —N$R^8SO_2R^{20}$, —OC(O)N$R^{21}R^{22}$, $R^{23}$-alkenyloxy, $R^{23}$-alkynyloxy, $R^{23}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —N$R^8SO_2$NH$R^{21}$ or —C(═NO$R^{18}$)$R^{19}$;

$R^{17}$ is 1 to 3 moieties and each $R^{17}$ independently hydrogen, $R^{23}$-alkyl, halogen, —CN, —$NO_2$, —OH, $R^{23}$-alkoxy, —OC(O)$R^{20}$, —C(O)O$R^{20}$, —C(O)$R^{20}$, —C(O)N$R^{21}R^{22}$, —N$R^{21}R^{22}$, —N$R^8$C(O)$R^{20}$, —N$R^8$C(O)N$R^{21}R^{22}$, —N$R^8SO_2R^{20}$, —OC(O)N$R^{21}R^{22}$, —S(O)$R^{20}$, —$S(O)_2R^{20}$, —S$R^{20}$, —$SO_2$N$R^{21}R^{22}$, —NHCO$R^{20}$, —C(NH)—$NH_2$, —C(O)N$R^{21}R^{22}$, $R^{23}$-alkenyloxy, $R^{23}$-alkynyloxy, $R^{24}$-cycloalkyl, $R^{24}$-cycloalkenyl, $R^{24}$-heterocycloalkyl, $R^{24}$-aryl, $R^{24}$-heteroaryl, $R^{24}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —N$R^8SO_2$NH$R^{21}$ or —C(═NO$R^{18}$)$R^{19}$;

$R^{18}$ is H, alkyl, phenyl or benzyl;

$R^{19}$ is H, alkyl, phenyl or benzyl $R^{20}$, $R^{21}$ and $R^{22}$ are independently hydrogen, alkyl, haloalkyl, alkenyl, alkynyl, aryl, aralkyl, cycloalkyl, halocycloalkyl or alkoxyalkyl;

$R^{23}$ is 1 to 3 moieties and each $R^{23}$ is independently hydrogen, halogen, —OH, alkyl, haloalkyl, alkoxy, —CN, amino, alkylamino, dialkylamino, di(alkyl)amino, haloalkoxy, hydroxyalkyl, —CHO, —C(O)alkylamino, —C(O)alkylamino, —NHC(O)alkyl or —N(alkyl)C(O)alkyl;

$R^{24}$ is 1 to 3 moieties and each $R^{24}$ is independently hydrogen, halogen, —OH, alkyl, haloalkyl, alkoxy, —CN, amino, alkylamino, dialkylamino, di(alkyl)amino, haloalkoxy, hydroxyalkyl, —CHO, —C(O)alkylamino, C(O)alkylamino, NHC(O)alkyl or —N(alkyl)C(O)alkyl;

$R^{25}$ is H, $R^{17}$-alkyl, $R^{17}$-cycloalkyl, $R^{17}$-aryl, $R^{17}$-heterocycloalkyl, $R^{17}$-aryl or $R^{17}$-heteroaryl;

$R^{26}$ is H, OH, —C(O)N($R^{21}$)($R^{22}$), —C(S)N($R^{21}$)($R^{22}$), —C(O)$R^{12}$, —$S(O)_2R^{12}$, $R^{17}$-alkyl, $R^{17}$-cycloalkyl, $R^{17}$-aryl, $R^{17}$-heterocycloalkyl or $R^{17}$-heteroaryl; and a is 1 or 2.

8. The compound as defined in claim 7 or a pharmaceutically acceptable salt thereof, wherein $R^{19}$ is fluoro;

$R^{11}$ is fluoro;

W is $R^{17}$-phenyl; and $R^{17}$ is 1 to 2 moieties and each $R^{17}$ is independently halogen, —CN, alkyl, haloalkoxy or $R^{24}$-heteroaryl.

9. The compound as defined in claim 1 or a pharmaceutically acceptable salt thereof, which has the structural formula

V

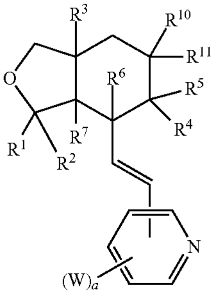

wherein:

$R^1$ is H, alkyl or haloalkyl;

$R^2$ is H, alkyl or haloalkyl;

$R^3$ is —$N_3$, —CN, halogen, —$OR^{12}$, —N($R^{25}$)($R^{26}$), —C(O)$OR^{12}$, —C(O)N($R^{25}$)($R^{26}$), —$SO_2$($R^{12}$), $R^{17}$-alkyl, $R^{17}$-cycloalkyl, $R^{17}$-aryl, $R^{17}$-heterocycloalkyl, $R^{17}$-aryl, or $R^{17}$-heteroaryl;

$R^4$ is H, alkyl or haloalkyl;

$R^5$ is H, alkyl or haloalkyl;

$R^6$ is H or alkyl;

$R^7$ is H or alkyl;

$R^8$ independently is H or alkyl;

$R^9$ independently is H or alkyl;

$R^{10}$ is fluoro;

$R^{11}$ is fluoro;

$R^{12}$ independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{13}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, $R^{17}$-heteroaryl, $R^{17}$-heteroarylalkyl or $R^{17}$-heteroarylalkenyl;

$R^{14}$ is independently is H, $R^{16}$-alkyl, $R^{16}$-alkenyl, $R^{17}$-cycloalkyl, $R^{17}$-arylalkyl, $R^{17}$-arylalkenyl, $R^{17}$-aryl, —C(O)$R^{12}$, —$S(O)_2$—$R^{12}$, $R^{17}$-heteroaryl, $R^{17}$-heteroarylalkyl or $R^{17}$-heteroarylalkenyl;

or $R^{13}$ and $R^{14}$ taken together with the nitrogen atom to which they are attached are —$(CH_2)_4$—, —$(CH_2)_5$— or —$(CH_2)_2$—N($R^8$)—$(CH_2)_2$—;

W is independently hydrogen, alkyl, haloalkyl, $R^{17}$-cycloalkyl, $R^{17}$-heterocycloalkyl, $R^{16}$-alkenyl, $R^{17}$-aryl, $R^{17}$-heteroaryl, $R^{17}$-arylalkyl, $R^{17}$-arylalkenyl, $R^{17}$-heteroarylalkyl, $R^{17}$-heteroarylalkenyl, hydroxyalkyl, dihydroxyalkyl, aminoalkyl, alkylaminoalkyl, di-(alkyl)-aminoalkyl, alkoxy, -alkyl-SH, —S-alkyl, alkenyloxy, halogen, —$NR^{13}R^{14}$, —CN, —OH, —C(O)$OR^{12}$, —$COR^{12}$, —$OS(O_2)CF_3$, —$CH_2OCH_2CF_3$, —C(O)$NR^{13}NR^{14}$, —$OCHR^{15}$-phenyl, phenoxyalkyl, —$NR^8COR^{12}$, —$NR^8SO_2R^{12}$, —C(O)$NR^{13}R^{14}$, —OC$(R^{15})_2COOR^{12}$, —OC$(R^{15})_2$C(O)$NR^{13}R^{14}$, alkoxy optionally substituted by alkyl, amino or —$NR^8$C(O)$OR^{12}$, or alkyl optionally substituted with —$NR^{13}R^{14}$, —$NR^{13}COR^{12}$, —$NR^8CONR^{13}R^{14}$, —$NR^8$C(O)$OR^{12}$, —$NR^8S(O)_2R^{12}$, —$NR^8S(O)_2NR^{13}R^{14}$—C(O)$OR^{12}$, —$CONR^{13}R^{14}$ or —OH;

$R^{15}$ independently is H, alkyl, cycloalkyl, alkoxyalkyl, hydroxyalkyl, aminoalkyl or phenyl;

$R^{16}$ is 1 to 3 moieties and each $R^{16}$ is independently hydrogen, halogen, —OH, alkoxy, -alkyl-SH, —S-alkyl, $R^{24}$-aryl, $R^{24}$-heteroaryl, $R^{24}$-heterocycloalkyl, $R^{24}$-cycloalkyl, $R^{24}$-cycloalkenyl, $R^{24}$-heterocyclenyl, —OC(O)$R^{20}$, —C(O)$OR^{20}$, —C(O)$R^{20}$, —C(O)$NR^{21}R^{22}$, —$NR^{21}R^{22}$, —$NR^8$C(O)$R^{20}$, —$NR^8$C(O)$NR^{21}R^{22}$, —$NR^8SO_2R^{20}$, —OC(O)$NR^{21}R^{22}$, $R^{23}$-alkenyloxy, $R^{23}$-alkynyloxy, $R^{23}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —$NR^8SO_2NHR^{21}$ or —C(=$NOR^{18}$)$R^{19}$;

$R^{17}$ is 1 to 3 moieties and each $R^{17}$ independently hydrogen, $R^{23}$-alkyl, halogen, —CN, —$NO_2$, —OH, $R^{23}$-alkoxy, —OC(O)$R^{20}$, —C(O)$OR^{20}$, —C(O)$R^{20}$, —C(O)$NR^{21}R^{22}$, —$NR^{21}R^{22}$, —$NR^8$C(O)$R^{20}$, —$NR^8$C(O)$NR^{21}R^{22}$, —$NR^8SO_2R^{20}$, —OC(O)$NR^{21}R^{22}$, —S(O)$R^{20}$, —$S(O)_2R^{20}$, —$SR^{20}$, —$SO_2NR^{21}R^{22}$, —$NHCOR^{20}$, —C(NH)—$NH_2$, —C(O)$NR^{21}R^{22}$, $R^{23}$-alkenyloxy, $R^{23}$-alkynyloxy, $R^{24}$-cycloalkyl, $R^{24}$-cycloalkenyl, $R^{24}$-heterocycloalkyl, $R^{24}$-aryl, $R^{24}$-heteroaryl, $R^{24}$-heterocycloalkyloxy, $R^{24}$-cycloalkyloxy, $R^{24}$-cycloalkenyloxy, $R^{24}$-aryloxy, $R^{24}$-heteroaryloxy, $R^{24}$-cycloalkyl-NH—, —$NR^8SO_2NHR^{21}$ or —C(=$NOR^{18}$)$R^{19}$;

$R^{18}$ is H, alkyl, phenyl or benzyl;

$R^{19}$ is H, alkyl, phenyl or benzyl $R^{20}$, $R^{21}$ and $R^{22}$ are independently hydrogen, alkyl, haloalkyl, alkenyl, alkynyl, aryl, aralkyl, cycloalkyl, halocycloalkyl or alkoxyalkyl;

$R^{23}$ is 1 to 3 moieties and each $R^{23}$ is independently hydrogen, halogen, —OH, alkyl, haloalkyl, alkoxy, —CN, amino, alkylamino, dialkylamino, di(alkyl)amino, haloalkoxy, hydroxyalkyl, —CHO, —C(O)alkylamino, —C(O)alkylamino, —NHC(O)alkyl or —N(alkyl)C(O)alkyl;

$R^{24}$ is 1 to 3 moieties and each $R^{24}$ is independently hydrogen, halogen, —OH, alkyl, haloalkyl, alkoxy, —CN, amino, alkylamino, dialkylamino, di(alkyl)amino, haloalkoxy, hydroxyalkyl, —CHO, —C(O)alkylamino, C(O)alkylamino, NHC(O)alkyl or —N(alkyl)C(O)alkyl;

$R^{25}$ is H; $R^{17}$-alkyl, $R^{17}$-cycloalkyl, $R^{17}$-aryl, $R^{17}$-heterocycloalkyl or $R^{17}$-heteroaryl;

$R^{26}$ is H, OH, —C(O)N($R^{21}$)($R^{22}$), —C(S)N($R^{21}$)($R^{22}$), —C(O)$R^{12}$, —$S(O)_2R^{12}$, $R^{17}$-alkyl, $R^{17}$-cycloalkyl, $R^{17}$-aryl, $R^{17}$-heterocycloalkyl or $R^{17}$-heteroaryl; and a is 1 or 2.

10. The compound as defined in claim 9 or a pharmaceutically acceptable salt thereof, wherein $R^{10}$ is fluoro;

$R^{11}$ is fluoro;

W is $R^{17}$-phenyl; and $R^{17}$ is 1 to 2 moieties and each $R^{17}$ is independently are halogen, —CN, alkyl, haloalkoxy or $R^{24}$-heteroaryl.

11. A pharmaceutical composition comprising an effective amount of a compound as defined in claim 1 or a pharmaceutically acceptable salt thereof and a pharmaceutically acceptable carrier.

12. The pharmaceutical composition as defined in claim 11, which further comprises a therapeutically effective amount of at least one additional cardiovascular agent.

13. The pharmaceutical composition as defined in claim 12, wherein the at least one additional cardiovascular agent is aspirin or clopidogrel, wherein clopidogrel is its free base or pharmaceutically acceptable salt.

14. The compound of claim 1 selected from:

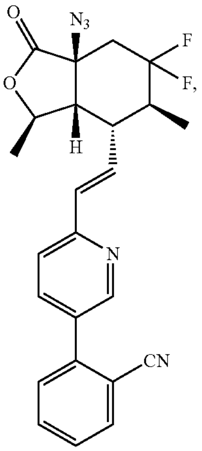

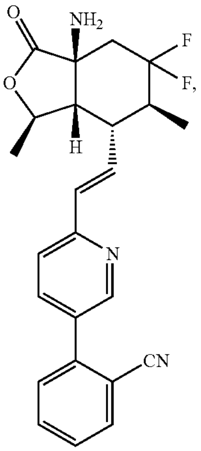

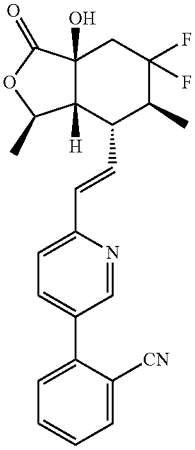

,

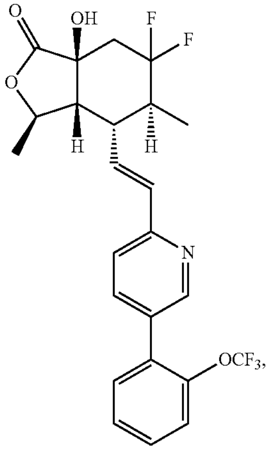

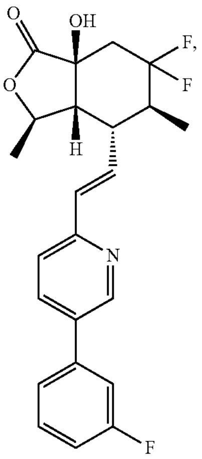

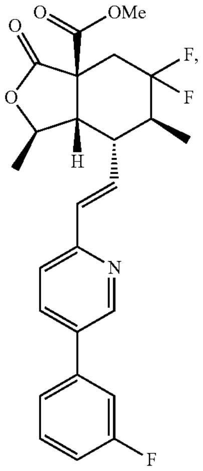

-continued

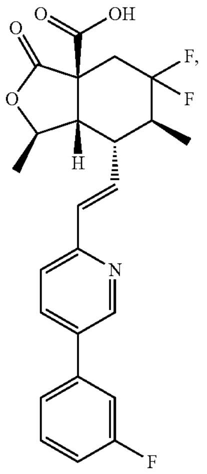

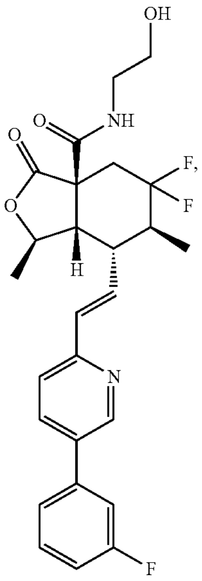

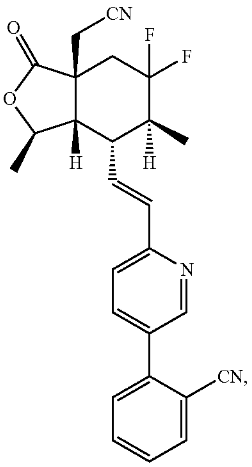

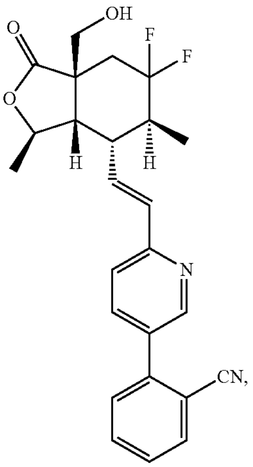

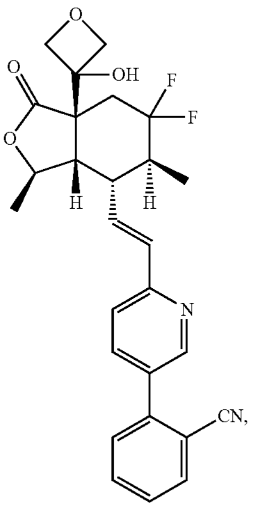

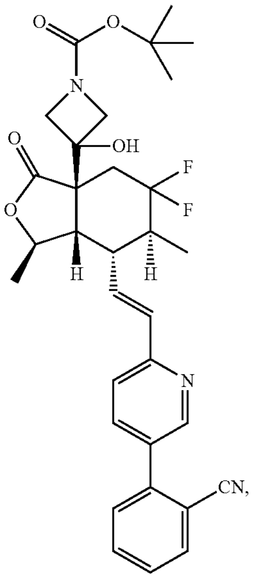

-continued
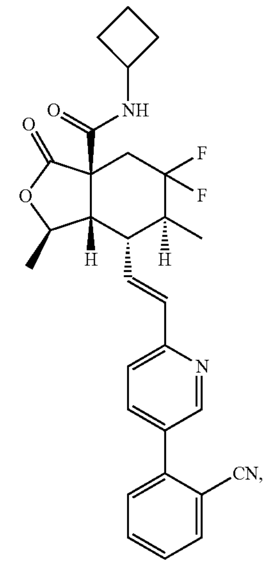
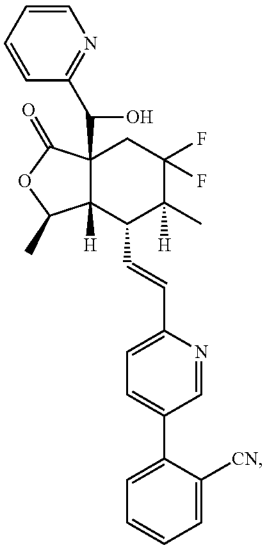
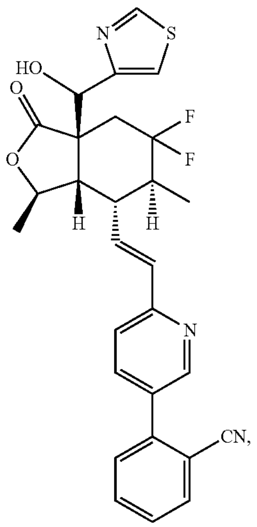
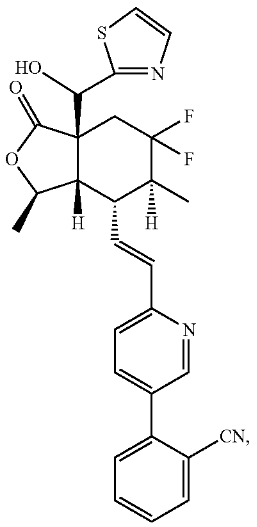
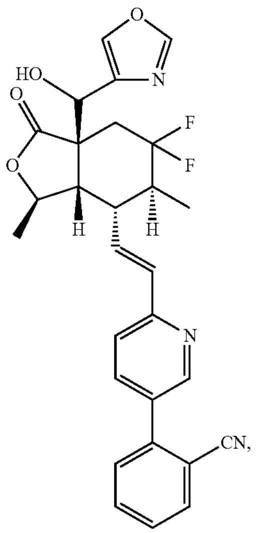
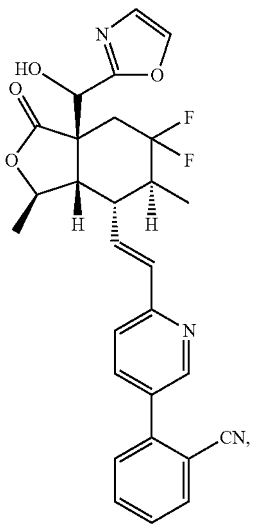
-continued
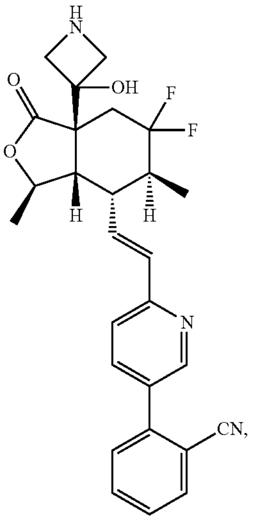
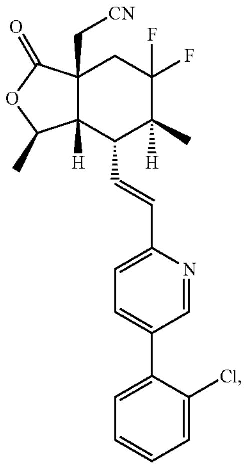
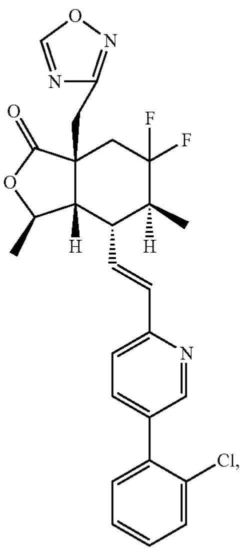
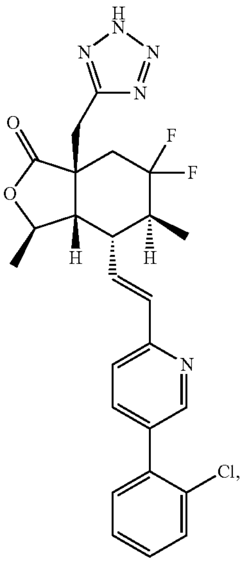
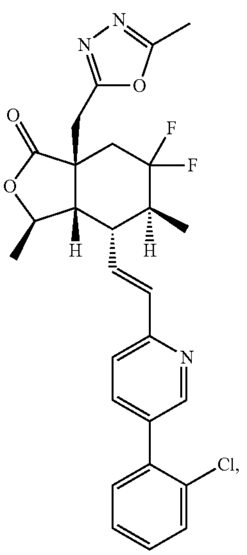
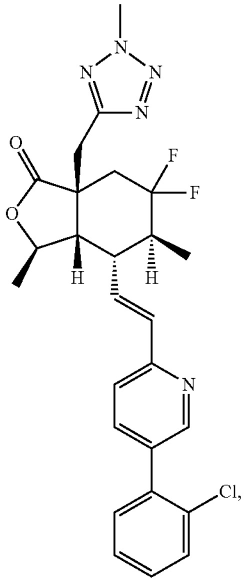

-continued
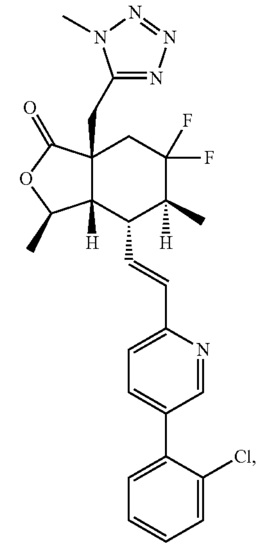
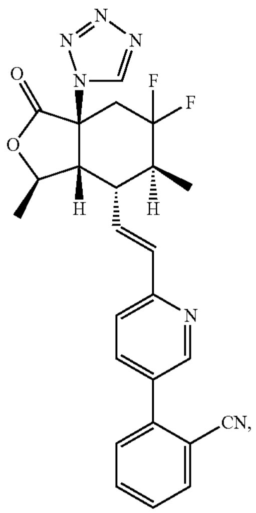
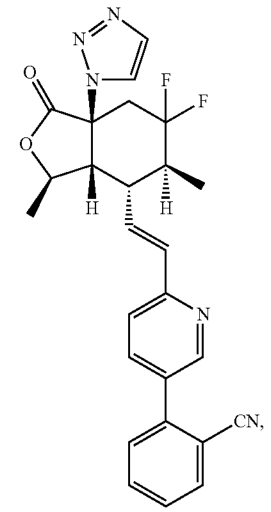
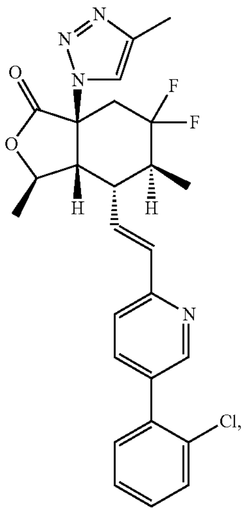
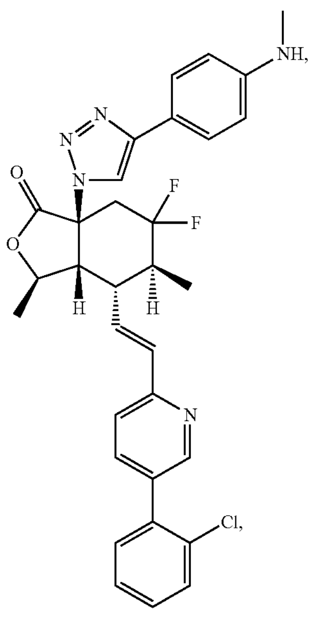
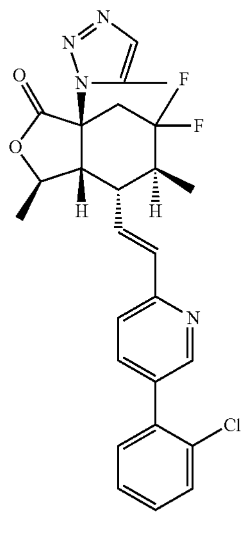
,
-continued
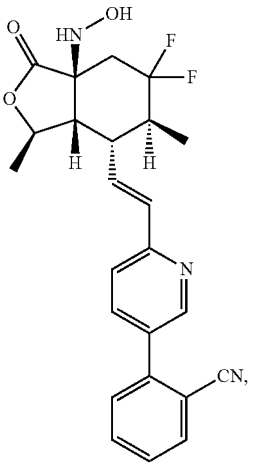
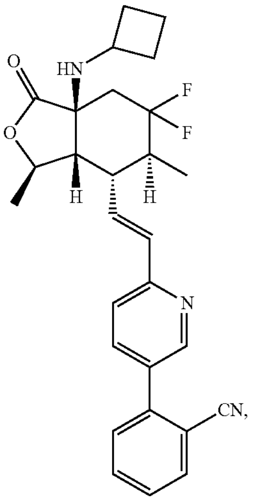
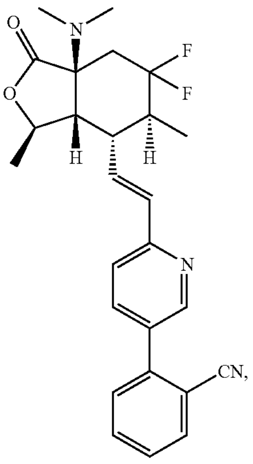
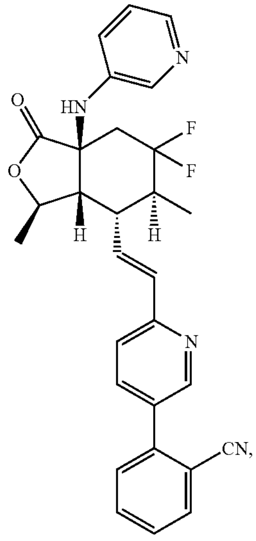
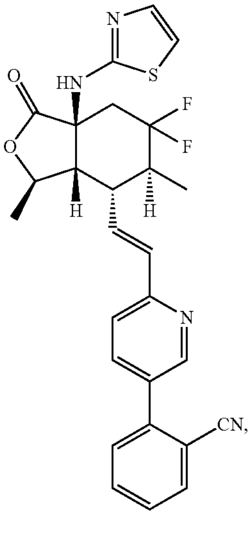
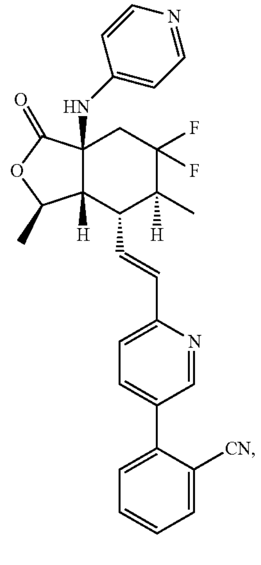

-continued
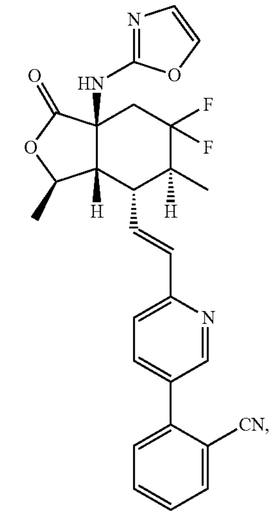
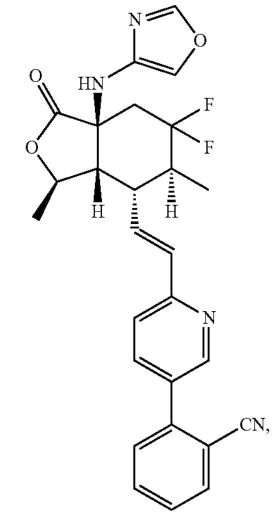
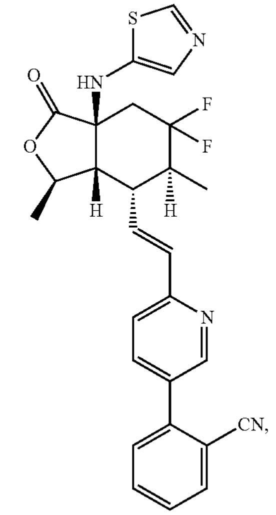
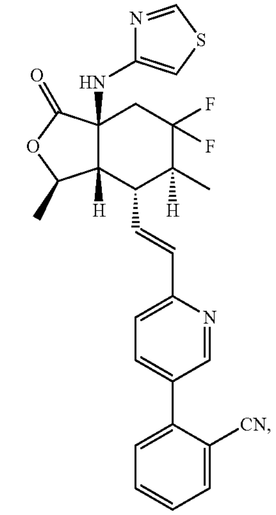
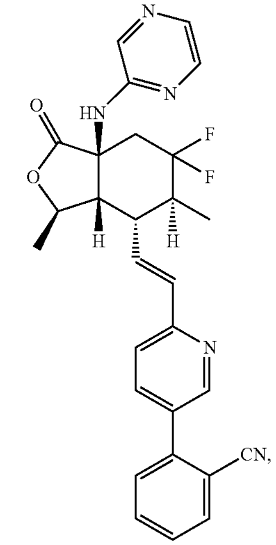
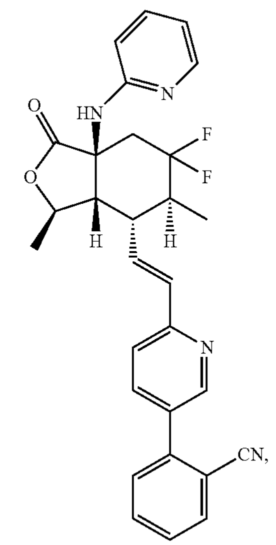
-continued
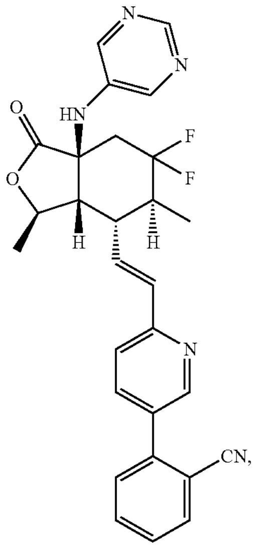
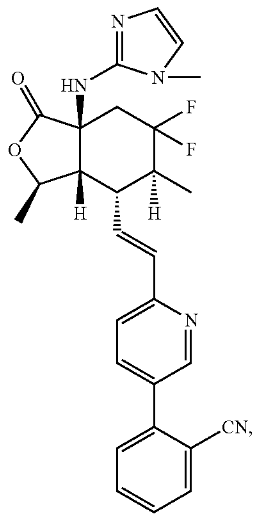
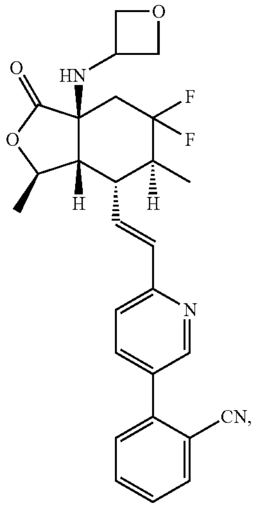
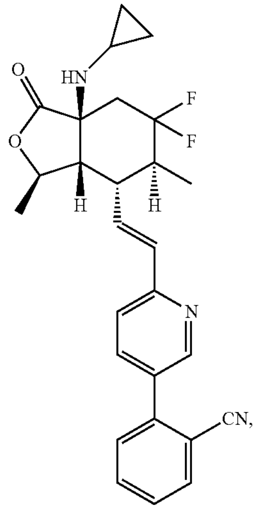
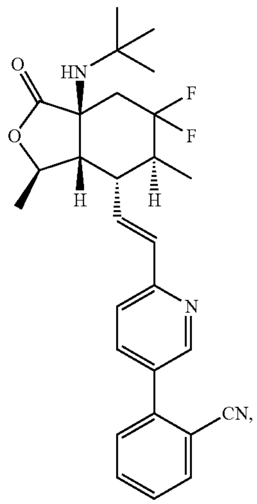
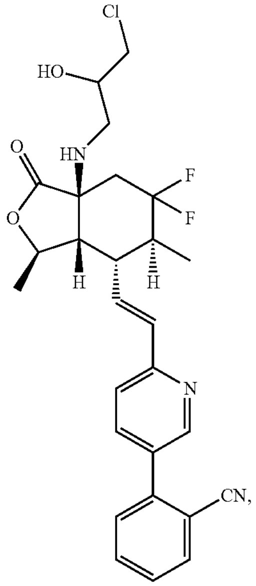

-continued
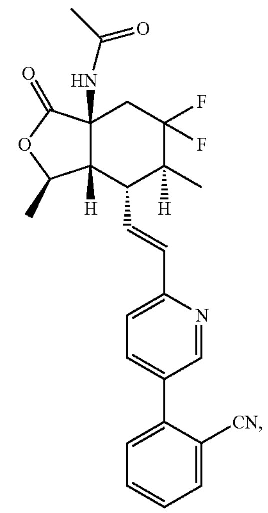
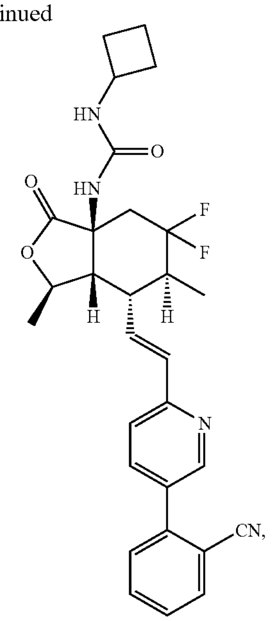
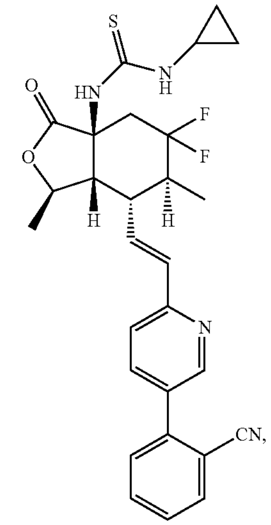
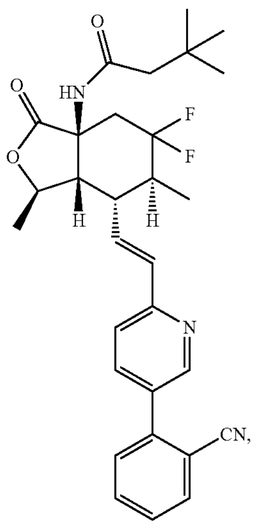
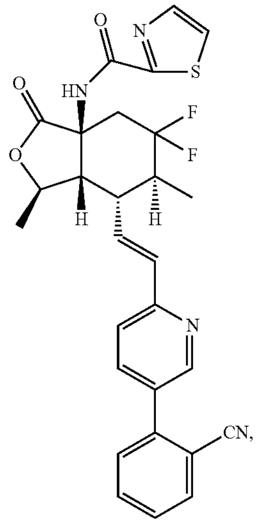
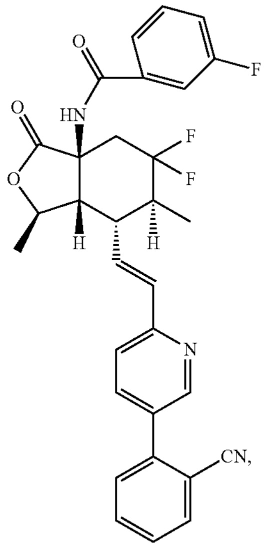
-continued
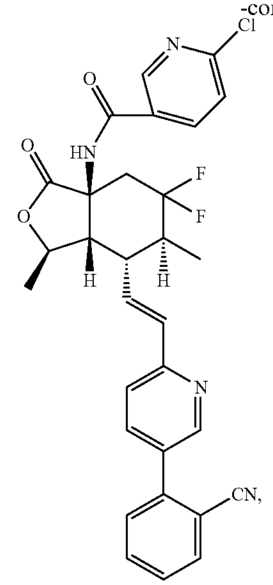
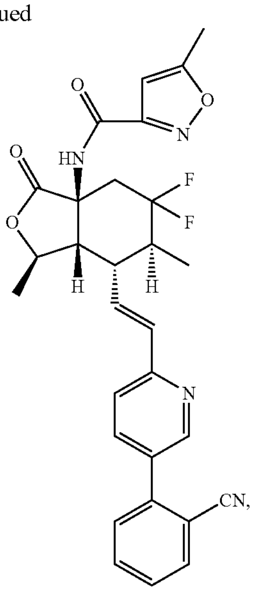
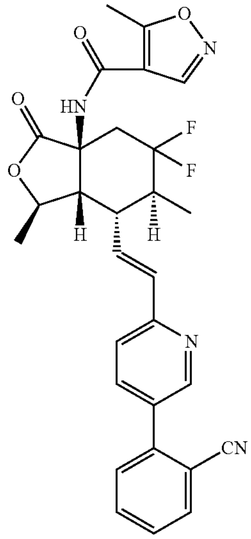
,
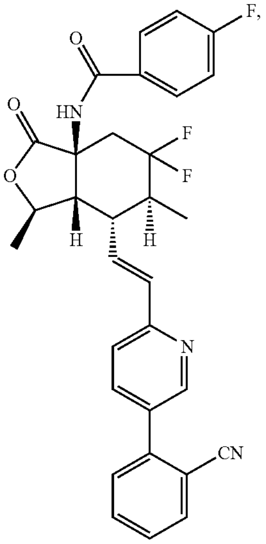
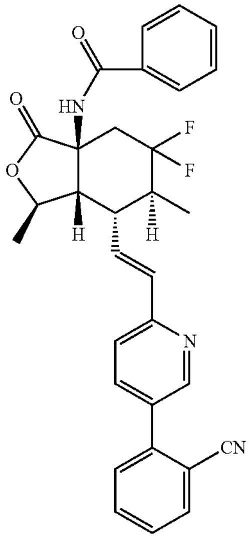
,
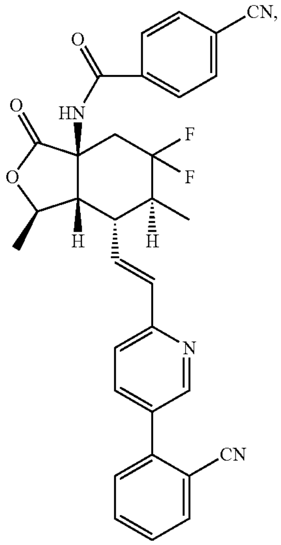

-continued
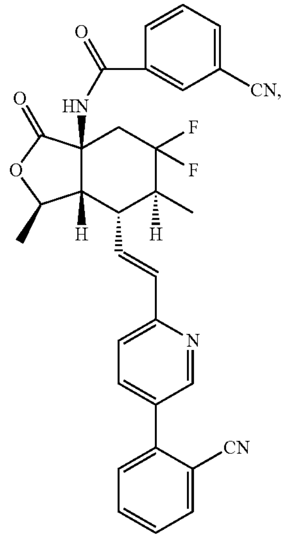
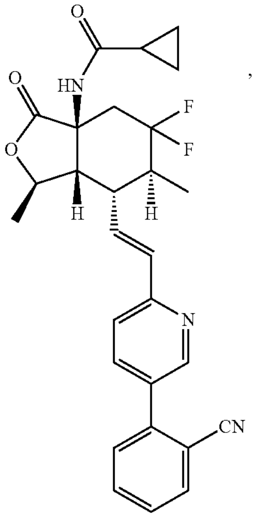
,
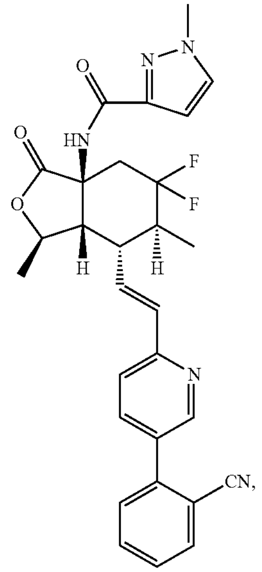
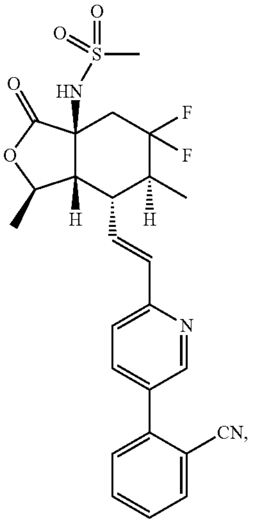
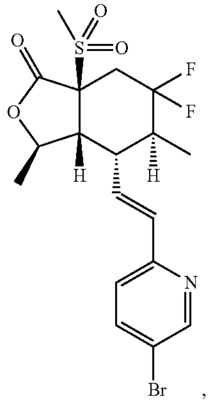
,
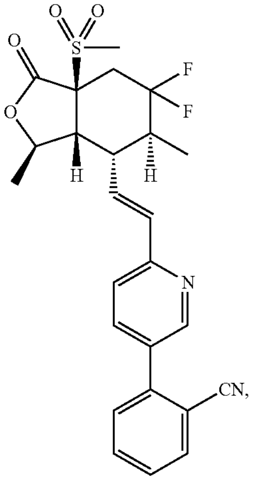
-continued
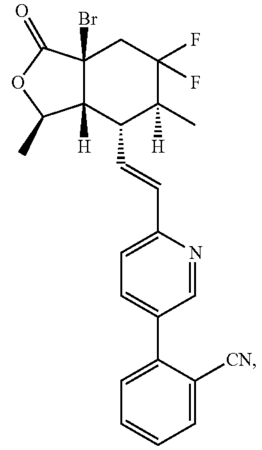
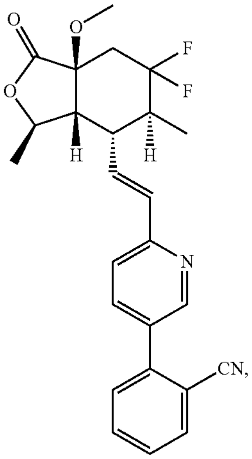
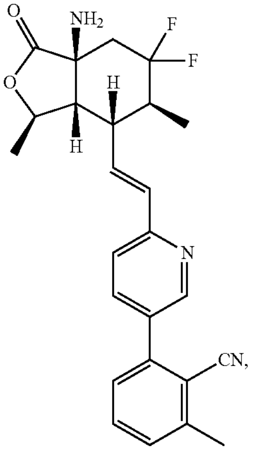
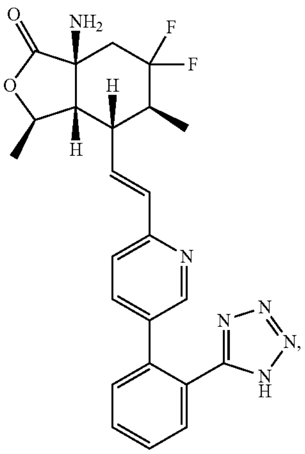
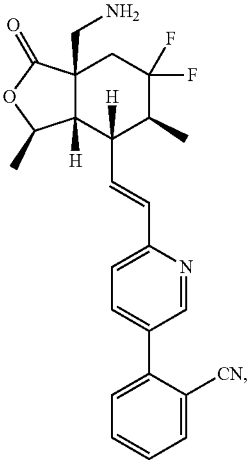
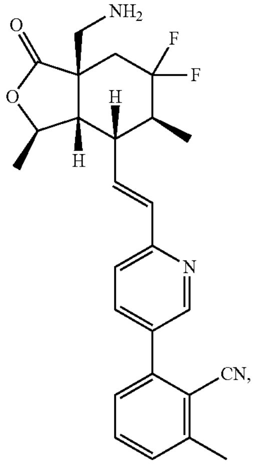

-continued
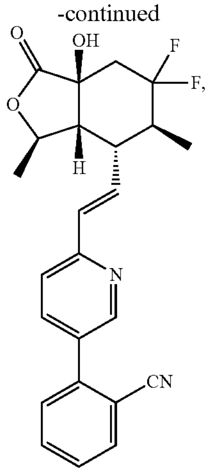
or a pharmaceutically acceptable salt thereof.
* * * * *